US012144796B2

(12) United States Patent
Odumosu et al.

(10) Patent No.: US 12,144,796 B2
(45) Date of Patent: Nov. 19, 2024

(54) FORMULATIONS FOR TREATING CLUSTER SYMPTOMS ASSOCIATED WITH AUTISM SPECTRUM DISORDER

(71) Applicant: Ilera Therapeutics LLC, Newtown Square, PA (US)

(72) Inventors: Oludare Odumosu, Newtown Square, PA (US); Erica Daniels, Newtown Square, PA (US); Zachary Swope, Newtown Square, PA (US); Megan Watkins, Newtown Square, PA (US)

(73) Assignee: Hera Therapeutics LLC, Newtown Square, PA (US)

( * ) Notice: Subject to any disclaimer, the term of this patent is extended or adjusted under 35 U.S.C. 154(b) by 0 days.

(21) Appl. No.: 18/127,612

(22) Filed: Mar. 28, 2023

(65) Prior Publication Data
US 2024/0066005 A1 Feb. 29, 2024

Related U.S. Application Data

(63) Continuation of application No. 17/468,023, filed on Sep. 7, 2021, now Pat. No. 11,622,957, which is a continuation of application No. PCT/US2020/021767, filed on Mar. 9, 2020.

(60) Provisional application No. 62/852,513, filed on May 24, 2019, provisional application No. 62/815,236, filed on Mar. 7, 2019.

(51) Int. Cl.
| | |
|---|---|
| *A61K 31/352* | (2006.01) |
| *A61K 31/015* | (2006.01) |
| *A61K 31/045* | (2006.01) |
| *A61K 31/05* | (2006.01) |
| *A61P 25/22* | (2006.01) |

(52) U.S. Cl.
CPC .......... *A61K 31/352* (2013.01); *A61K 31/015* (2013.01); *A61K 31/045* (2013.01); *A61K 31/05* (2013.01); *A61P 25/22* (2018.01)

(58) Field of Classification Search
CPC .................................................. A61K 31/485
See application file for complete search history.

(56) References Cited

U.S. PATENT DOCUMENTS

| 11,622,957 B2 | 4/2023 | Odumosu et al. |
| 2018/0169035 A1 | 6/2018 | Eyal |
| 2018/0344786 A1 | 12/2018 | Thacker, Jr. et al. |
| 2019/0046499 A1* | 2/2019 | Segreti .................. A61K 31/05 |

FOREIGN PATENT DOCUMENTS

| AU | 2018101357 A4 * | 10/2018 | .............. A61K 31/05 |
| WO | WO-2017151980 A1 | 9/2017 | |
| WO | WO-2017158539 A1 | 9/2017 | |
| WO | WO-2018175992 A1 * | 9/2018 | .......... A23L 33/105 |
| WO | WO-2019089583 A1 * | 5/2019 | .......... A61K 31/015 |
| WO | WO-2020181295 A1 | 9/2020 | |

OTHER PUBLICATIONS

Bang et al., "Herbal medicine treatment for children with autism spectrum disorder: a systematic review," Evid Based Complement Alternat Med., vol. 2017, May 16, 2017, Article ID 8614680, 12 pages.
Braga et al., "Antioxidant Activity of Bisabolol: Inhibitory Effects on Chemiluminescence of Human Neutrophil Bursts and Cell-Free Systems," Pharmacology. 2009;83(2):110-115.
Consroe, P, et al., "Open label evaluation of cannabidiol in dystonic movement disorders". International Journal of Neuroscience. (Jan. 1, 1986); 30(4): 277-282.
D'Agati et al., "Treatment of severe self-injurious behavior in autism spectrum disorder by neuromodulation," The Journal of ECT, Mar. 2017, vol. 33, Issue 1, pp. 7-11.
Eapen et al., "Current status of biological treatment options in autism spectrum disorder," Asian Journal of Psychiatry, vol. 30, Dec. 2017, pp. 1-10.
El-Alfy, A. T., et al., "Antidepressant-like effect of A9-tetrahydro-cannabinol and other cannabinoids isolated from *Cannabis sativa* L". Pharmacology Biochemistry and Behavior (Jun. 1, 2010); 95(4): 434-442.
Eisohly, "Marijuana and the Cannabinoids," Humana Press, 2007, 331 pages; https://saltonverde.com/wp-content/uploads/2017/09/18-Marijuana_and_the_Cannabinoids.pdf.
Ertas et al., "Essential oil compositions and anticholinesterase activities of two edible plants *Tragopogon latifolius* var. *angustifolius* and Lycopsis orientalis," Nat Prod Res. 2014;28(17): pp. 1405-1408.
Eubanks, L. M., et al., "A molecular link between the active component of marijuana and Alzheimer's disease pathology". Molecular Pharmaceutics (Dec. 4, 2006); 3(6): 773-777.
Extended European Search Report dated Nov. 21, 2022, issued in European Application. No. 20765574. 7, 7 pages.
Fischedick, J. et al., "Metabolic fingerprinting of *Cannabis sativa* L., cannabinoids and terpenoids for chemotaxonomic and drug standardization purposes" Phytochemistry 2010, vol. 71., pp. 2058-2073.
Fitzpatrick et al., "Aggression in autism spectrum disorder: presentation and treatment options," Neuropsychiatr Dis Treat., Jun. 23, 2016, 12: pp. 1525-1538.
Fung et al., "Pharmacologic treatment of severe irritability and problem behaviors in autism: a systematic review and meta-analysis," Pediatrics, Feb. 1, 2016, 137(Suppl 2S):pp. 124-135.
Hirota et al., "Antiepileptic medications in autism spectrum disorder: a systematic review and meta-analysis," Journal of Autism Development Disorders, Apr. 2014, 44:948-957.

(Continued)

*Primary Examiner* — Svetlana M Ivanova
(74) *Attorney, Agent, or Firm* — COOLEY LLP

(57) ABSTRACT

The present disclosure provides for pharmaceutical compositions useful for treating autism spectrum disorder. The pharmaceutical compositions comprise particular THC:CBD ratios and terpene profiles, which have been demonstrated effective at treating cluster symptoms associated with autism spectrum disorder.

19 Claims, No Drawings

(56) References Cited

OTHER PUBLICATIONS

Hoaken, P. N., et al., "Drugs of abuse and the elicitation of human aggressive behavior". Addictive Behaviors (Dec. 1, 2003); 28(9):1533-1554.

International Search Report and Written Opinion mailed on Jun. 17, 2020, in International Application No. PCT/US2020/021767, 11 pages.

Khalil et al., "Social decision making in autism: on the impact of mirror neurons, motor control, and imitative behaviors," CNS Neurosci Ther., Jun. 7, 2018, 24: pp. 669-676.

Khan et al., "1,8-cineole (eucalyptol) mitigates inflammation in amyloid Beta toxicated PC12 cells: relevance to Alzheimer's disease," Neurochem Res. 2014. 39(2): pp. 344-352.

Leite et al., "(−)-α-Bisabolol attenuates visceral nociception and inflammation in mice," Fioterapia. 2011, 82(2):208-211.

Masi et al., "A comprehensive systematic review and meta-analysis of pharmacological and dietary supplement interventions in paediatric autism: moderators of treatment response and recommendations for future research," Psychol Med., Jan. 16, 2017, vol. 47, Issue 7, pp. 1323-1334.

McAllister, S.D., et al., "Cannabidiol as a novel inhibitor of Id-1 gene expression in aggressive breast cancer cells". Molecular Cancer Therapeutics (Nov. 1, 2007); 6(11): 2921-2927.

McPartland and Russo 2001 "Cannabis and Cannabis Extracts: Greater Than the Sum of Their Parts", Journal of Cannabis Therapeutics vol. 1, No. 3/4,2001, pp. 103-132.

Mechoulam, R., et al., "Cannabidiol-recent advances". Chemistry & Biodiversity (Aug. 2007); 4(8): 1678-1692.

Miraj et al., "A systematic review study of therapeutic effects of *Matricaria recuitta chamomile* (chamomile)," Electron Physician, Sep. 2016. 20;8(9): pp. 3024-3031.

Morgan, C.J., et al., "Impact of cannabidiol on the acute memory and psychotomimetic effects of smoked cannabis: naturalistic study". The British Journal of Psychiatry (Oct. 2010); 197(4): 285-290.

Nicholson, A.N., et al., "Effect of A-9-tetrahydrocannabinol and cannabidiol on nocturnal sleep and early-morning behavior in young adults". Journal of Clinical Psychopharmacology (Jun. 1, 2004); 24(3): 305-313.

Pertwee, R. G., "The pharmacology of cannabinoid receptors and their ligands: an overview". International Journal of Obesity (Apr. 2006); 30(1): S13-S18.

Pickens, J.T., "Sedative activity of cannabis in relation to its Δ'-trans-tetrahydrocannabinol and cannabidiol content". British Journal of Pharmacology (Apr. 1981); 72(4): 649-656.

Russo, E.B., "Taming THC: potential cannabis synergy and phytocannabinoid-terpenoid entourage effects" The British Journal of Pharmacology (2011); 163 (7): 1344-1364.

Sahoo et al., "Effectiveness of clozapine for the treatment of psychosis and disruptive behaviour in a child with atypical autism: a case report and a brief review of the evidence," Asian Journal of Psychiatry, vol. 29, Oct. 2017, pp. 194-195.

Schopler et al, "Toward objective classification of childhood autism: Childhood Autism Rating Scale (CARS)," Journal of Autism and Developmental Disorders, 1980; 19:91-103.

Soel et al., "Eucalyptol and Its Role in Chronic Diseases," Adv Exp Med Biol. 2016;929:389-398.

Tsoyi et al., "(+)-Nootkatone and (+)-valencene from rhizomes of Cyperus rotundus increase survival rates in septic mice due to heme oxygenase-1 induction," J Enthnopharmacol. 2011, 11;137(3):1311-1317.

Zuardi, A.W., et al., "Cannabidiol, a *Cannabis sativa* constituent, as an antipsychotic drug". Brazilian Journal of Medical and Biological Research (2006); 39: 421-429.

Broken Big Toe and Weed, Discussion in 'Medical Marijuana usage and Applications' started by tom1981, May 21, 2011, 9 pages, https://forum.grasscity.com/threads/broken-big-toe-and-weed.819778/.

Medical College of Georgia at Augusta University. "CBD reduces glioblastoma's size, supportive environment in experimental model." ScienceDaily. ScienceDaily, Dec. 23, 2021, 5 pages. www.sciencedaily.com/releases/2021/12/211223141935.htm.

Nuutinen T., "Medicinal properties of terpenes found in *Cannabis sativa* and Humulus lupulus," European Journal of Medicinal Chemistry. Sep. 5, 2018;157:198-228.

Paland et al., "The Immunopathology of COVID-19 and the Cannabis Paradigm" Frontiers in Immunology, Feb. 2021, vol. 12, Article 631233, 13 pages.

* cited by examiner

FORMULATIONS FOR TREATING CLUSTER SYMPTOMS ASSOCIATED WITH AUTISM SPECTRUM DISORDER

CROSS-REFERENCE TO RELATED APPLICATIONS

This application is a continuation of U.S. Non-Provisional application Ser. No. 17/468,023, filed Sep. 7, 2021, now U.S. Pat. No. 11,622,957, which is a continuation of International Application No. PCT/US2020/021767, filed Mar. 9, 2020. This application claims priority to U.S. Provisional Application No. 62/852,513 filed May 24, 2019 and U.S. Provisional Application No. 62/815,236 filed Mar. 7, 2019. Each of the aforementioned applications is incorporated by reference herein in its entirety for all purposes.

FIELD

The present disclosure generally relates to compositions and formulations thereof comprising unique combinations of cannabinoids and terpenes, methods of making the compositions, and methods for using the compositions for the treatment of autism.

BACKGROUND

Autism spectrum disorder (ASD) is a serious neurodevelopmental disorder characterized by stereotypic behaviors and deficits in language and social interaction, repetitive behaviors, abnormal movements, and sensory dysfunction. Autism is defined behaviorally because there are no definitive biological markers of the disorder. It classically appears during the first three years of life and is said to be the result of a neurological disorder which affects the functioning of the brain. The reported incidence of autism has rapidly increased to 1 in 88 births in the United States as of 2008 (CDC, 2012), representing a significant medical and social burden in the coming decades.

Medical marijuana is largely an unstudied entity and has over 80 active constituents. Each constituent has its own potential pharmacologic actions and different blends of these constituents have the potential to reap significant therapeutic benefits. Medical marijuana is more commonly being used in Pennsylvania for 21 approved serious conditions, including autism, since legalization in 2016. Yet, there is a gap in knowledge regarding the utilization of medical marijuana in the treatment of autism and related disorders.

SUMMARY

There is an unmet need for improved methods of treatment of ASD with various combinations of therapeutic agents that can reduce symptoms associated with autism. The present invention and methods provide these and/or other advantages to existing treatments.

In some embodiments, the present disclosure provides a pharmaceutical composition for the treatment of autism, comprising: (a) a Cannabinoid Profile comprising two or more cannabinoids, wherein the two or more cannabinoids comprise Tetrahydrocannabinol (THC) and Cannabidiol (CBD); and (b) a Terpene Profile comprising two or more terpenes selected from α-Pinene, Valencene, Eucalyptol, β-Caryophyllene (BCP), Myrcene, α-Bisabolol, and Pulegone.

In some embodiments, the ratio of THC:CBD is 1:1. In some embodiments, the ratio of THC:CBD is 5:1.

In some embodiments, the Terpene Profile comprises α-Pinene, Valencene, and Eucalyptol. In some embodiments, the Terpene Profile comprises, in order of relative abundance (from low to high): (a) α-Pinene, Valencene, and Eucalyptol; (b) α-Pinene, Eucalyptol, and Valencene; (c) Valencene, α-Pinene, and Eucalyptol; (d) Valencene, Eucalyptol, and α-Pinene; (e) Eucalyptol, α-Pinene, and Valencene; or (f) Eucalyptol, Valencene, and α-Pinene.

In some embodiments, the Terpene Profile comprises 15%-35% α-Pinene, 15%-35% Valencene, and 40%-60% Eucalyptol, wherein the total of % α-Pinene+% Valencene+% Eucalyptol=100%. In some embodiments, the Terpene Profile comprises 20%-40% α-Pinene, 20%-40% Valencene, and 20%-40% Eucalyptol, wherein the total of % α-Pinene+% Valencene+% Eucalyptol=100%. In some embodiments, the Terpene Profile comprises 20%-40% α-Pinene, 20%-40% Valencene, and 30%-50% Eucalyptol, wherein the total of % α-Pinene+% Valencene+% Eucalyptol=100%. In some embodiments, the Terpene Profile comprises 25%-35% α-Pinene, 25%-35% Valencene, and 30%-40% Eucalyptol, wherein the total of % α-Pinene+% Valencene+% Eucalyptol=100%.

In some embodiments, the Terpene Profile comprises BCP, Myrcene, α-Bisabolol, and Pulegone. In some embodiments, the Terpene Profile comprises, in order of relative abundance (from low to high): (a) BCP, myrcene, α-bisabolol, and pulegone; (b) BCP, myrcene, pulegone, and α-bisabolol; (c) BCP, pulegone, myrcene, and α-bisabolol; (d) BCP, pulegone, α-bisabolol, and myrcene; (e) BCP, α-bisabolol, pulegone, and myrcene; (f) BCP, α-bisabolol, myrcene, and pulegone; (g) α-bisabolol, BCP, myrcene, and pulegone; (h) α-bisabolol, BCP, pulegone, and myrcene; (i) α-bisabolol, myrcene, BCP, and pulegone; (j) α-bisabolol, myrcene, pulegone, and BCP; (k) α-bisabolol, pulegone, myrcene, and BCP; (l) α-bisabolol, pulegone, BCP, and myrcene; (m) myrcene, α-bisabolol, BCP, and pulegone; (n) myrcene, α-bisabolol, pulegone, and BCP; (o) myrcene, BCP, α-bisabolol, and pulegone; (p) myrcene, BCP, pulegone, and α-bisabolol; (q) myrcene, pulegone, BCP, and α-bisabolol; (r) myrcene, pulegone, α-bisabolol, and BCP; (s) pulegone, myrcene, α-bisabolol, and BCP; (t) pulegone, myrcene, BCP, and α-bisabolol; (u) pulegone, α-bisabolol, myrcene, and BCP; (v) pulegone, α-bisabolol, BCP, and myrcene; (w) pulegone, BCP, α-bisabolol, and myrcene; or (x) pulegone, BCP, myrcene, and α-bisabolol.

In some embodiments, the Terpene Profile comprises 35%-55% BCP, 10%-30% Myrcene, 10%-30% α-Bisabolol, and 5%-20% Pulegone, wherein the total of % BCP+% Myrcene+% α-Bisabolol+% Pulegone=100%. In some embodiments, the Terpene Profile comprises 15%-35% BCP, 15%-35% Myrcene, 15%-35% α-Bisabolol, and 10%-30% Pulegone, wherein the total of % BCP+% Myrcene+% α-Bisabolol+% Pulegone=100%.

In some embodiments, the Terpene Profile comprises BCP, Myrcene, and α-Bisabolol. In some embodiments, the Terpene Profile comprises, in order of relative abundance: (a) β-caryophyllene, myrcene, α-bisabolol; (b) β-caryophyllene, α-bisabolol, myrcene; (c) myrcene, β-caryophyllene, α-bisabolol; (d) myrcene, α-bisabolol, β-caryophyllene; (e) α-bisabolol, β-caryophyllene, myrcene; or (f) α-bisabolol, myrcene, β-caryophyllene In some embodiments, the Terpene Profile comprises 20%-40% BCP, 20%-40% Myrcene, and 20%-40% α-Bisabolol, wherein the total of % BCP+% Myrcene+% α-Bisabolol=100%. In some embodiments, the Terpene Profile comprises 30%-40% BCP, 30%-40% Myrcene, and 30%-

40% α-Bisabolo, wherein the total of % BCP+% Myrcene+% α-Bisabolol=100%.

In some embodiments, the present disclosure provides a pharmaceutical composition for the treatment of autism, comprising: (a) a Cannabinoid Profile comprising Tetrahydrocannabinol (THC) and Cannabidiol (CBD) present at a 1:1 ratio; and (b) a Terpene Profile comprising α-Pinene, Valencene, and Eucalyptol.

In some embodiments, the Terpene Profile comprises 15%-35% α-Pinene, 15%-35% Valencene, and 40%-60% Eucalyptol, wherein the total of % α-Pinene+% Valencene+% Eucalyptol=100%. In some embodiments, the Terpene Profile comprises 20%-40% α-Pinene, 20%-40% Valencene, and 20%-40% Eucalyptol, wherein the total of % α-Pinene+% Valencene+% Eucalyptol=100%. In some embodiments, the Terpene Profile comprises 20%-40% α-Pinene, 20%-40% Valencene, and 30%-50% Eucalyptol, wherein the total of % α-Pinene+% Valencene+% Eucalyptol=100%. In some embodiments, the Terpene Profile comprises 25%-35% α-Pinene, 25%-35% Valencene, and 30%-40% Eucalyptol, wherein the total of % α-Pinene+% Valencene+% Eucalyptol=100%.

In some embodiments, the ratio of total cannabinoids to total terpenes is between 10:1 and 5:1.

In some embodiments, the present disclosure provides a pharmaceutical composition for the treatment of autism, comprising: (a) a Cannabinoid Profile comprising Tetrahydrocannabinol (THC) and Cannabidiol (CBD) present at a 5:1 ratio; and (b) a Terpene Profile comprising β-Caryophyllene (BCP), Myrcene, α-Bisabolol, and Pulegone. In some embodiments, the Terpene Profile comprises 35%-55% BCP, 10%-30% Myrcene, 10%-30% α-Bisabolol, and 5%-20% Pulegone, wherein the total of % BCP+% Myrcene+% α-Bisabolol+% Pulegone=100%. In some embodiments, the Terpene Profile comprises 15%-35% BCP, 15%-35% Myrcene, 15%-35% α-Bisabolol, and 10%-30% Pulegone, wherein the total of % BCP+% Myrcene+% α-Bisabolol+% Pulegone=100%.

In some embodiments, the present disclosure provides a pharmaceutical composition for the treatment of autism, comprising: (a) a Cannabinoid Profile comprising Tetrahydrocannabinol (THC) and Cannabidiol (CBD) present at a 5:1 ratio; and (b) a Terpene Profile comprising β-Caryophyllene (BCP), Myrcene, and α-Bisabolol. In some embodiments, the Terpene Profile comprises 20%-40% BCP, 20%-40% Myrcene, and 20%-40% α-Bisabolol, wherein the total of % BCP+% Myrcene+% α-Bisabolol=100%. In some embodiments, the Terpene Profile comprises 30%-40% BCP, 30%-40% Myrcene, and 30%-40% α-Bisabolo, wherein the total of % BCP+% Myrcene+% α-Bisabolol=100%.

In some embodiments, the present disclosure provides a pharmaceutical composition comprising: (a) a Cannabinoid Profile comprising Tetrahydrocannabinol (THC) and Cannabidiol (CBD) present at a 1:1 ratio; and (b) a Terpene Profile comprising α-Pinene, Valencene, and Eucalyptol, wherein the Terpene Profile comprises about 25% by weight α-Pinene, about 25% by weight Valencene, and about 50% by weight Eucalyptol.

In some embodiments, the present disclosure provides a pharmaceutical composition comprising: (a) a Cannabinoid Profile comprising Tetrahydrocannabinol (THC) and Cannabidiol (CBD) present at a 1:1 ratio; and (b) a Terpene Profile comprising α-Pinene, Valencene, and Eucalyptol, wherein the Terpene Profile comprises about 31% by weight α-Pinene, about 31% by weight Valencene, and about 37.5% by weight Eucalyptol.

In some embodiments, the present disclosure provides a pharmaceutical composition comprising: (a) a Cannabinoid Profile comprising about 5 mg/mL Tetrahydrocannabinol (THC) and about 5 mg/mL Cannabidiol (CBD); and (b) a Terpene Profile comprising α-Pinene, Valencene, and Eucalyptol, wherein the Terpene Profile comprises about 0.43 mg/mL α-Pinene, about 0.43 mg/mL Valencene, and about 0.5 mg/mL Eucalyptol.

In some embodiments, the present disclosure provides a pharmaceutical composition comprising: (a) a Cannabinoid Profile comprising Tetrahydrocannabinol (THC) and Cannabidiol (CBD) present at a 5:1 ratio; and (b) a Terpene Profile comprising β-Caryophyllene (BCP), Myrcene, α-Bisabolol, and Pulegone, wherein the Terpene Profile comprises about 45% by weight BCP, about 21% by weight Myrcene, about 21% by weight α-Bisabolol, and about 12% by weight Pulegone.

In some embodiments, the present disclosure provides a pharmaceutical composition comprising: (a) a Cannabinoid Profile comprising Tetrahydrocannabinol (THC) and Cannabidiol (CBD) present at a 5:1 ratio; and (b) a Terpene Profile comprising β-Caryophyllene (BCP), Myrcene, and α-Bisabolol, wherein the Terpene Profile comprises about 33% by weight BCP, about 34% by weight Myrcene, and about 33% by weight α-Bisabolol.

In some embodiments, the present disclosure provides a pharmaceutical composition comprising: (a) a Cannabinoid Profile comprising 8.33 mg/mL Tetrahydrocannabinol (THC) and 1.67 mg/mL Cannabidiol (CBD); and (b) a Terpene Profile comprising β-Caryophyllene (BCP), Myrcene, and α-Bisabolol, wherein the Terpene Profile comprises about 1.8 mg/mL BCP, about 1.8 mg/mL Myrcene, and about 1.8 mg/mL α-Bisabolo In some embodiments, the ratio of total cannabinoids to total terpenes is between 1:1 and 3:1. In some embodiments, the terpenes in the Terpene Profile are present at a non-naturally occurring ratio.

In some embodiments, pharmaceutical composition further comprises one or more non-*Cannabis* plant extracts.

In some embodiments, at least one of the active ingredients is an enriched active ingredient. In some embodiments, each of the active ingredients is an enriched active ingredient. In some embodiments, at least one of the active ingredients is a substantially pure active ingredient. In some embodiments, each of the active ingredients is a substantially pure active ingredient.

In some embodiments, the pharmaceutical composition further comprises one or more flavors. In some embodiments, the one or more flavors are selected from orange, ginger, vanilla, raspberry, blackberry, grapefruit, and mint chocolate.

In some embodiments, the composition is formulated for oral administration. In some embodiments, the composition is formulated as a liquid dose. In some embodiments, the composition is formulated as a tincture. In some embodiments, the composition is formulated for parenteral administration. In some embodiments, the composition is formulated for buccal administration, as an oral mucosal absorption spray, as a transdermal patch, cream or ointment, or for intravenous administration.

In some embodiments, the present disclosure provides a method of treating autism, comprising: administering an effective amount of a pharmaceutical composition described herein to a subject in need thereof.

In some embodiments, the present disclosure provides a method of improving self-stimulatory behavior in patients with autism spectrum disorder (ASD), said method comprising the steps of administering a pharmaceutical composition comprising (a) a Cannabinoid Profile comprising Tetrahydrocannabinol (THC) and Cannabidiol (CBD) present at a 5:1 ratio; and (b) a Terpene Profile comprising β-Caryophyllene (BCP), Myrcene, α-Bisabolol, and Pulegone, wherein the Terpene Profile comprises about 45% by weight BCP, about 21% by weight Myrcene, about 21% by weight α-Bisabolol, and about 12% by weight Pulegone.

In some embodiments, the present disclosure provides a method of improving self-stimulatory behavior in patients with autism spectrum disorder (ASD), said method comprising the steps of administering a pharmaceutical composition described herein.

In some embodiments, the present disclosure provides a method of improving communication behavior in patients with autism spectrum disorder (ASD), said method comprising the steps of administering a pharmaceutical composition described herein.

In some embodiments, the present disclosure provides a method of improving communication behavior in patients with autism spectrum disorder (ASD), said method comprising the steps of administering a pharmaceutical composition described herein.

In some embodiments, the pharmaceutical composition is administered as a 2 mL, 2.5 mL, 3 mL, 3.5 mL, 4 mL, 4.5 mL, or 5 mL dose.

DETAILED DESCRIPTION

I. Overview

Although there has been a significant increase in ASD diagnoses worldwide, and among the most severe chronic childhood disorders in terms of prevalence, and impact to the society, no specific effective treatments for ASD are currently available (Lundström et al., *Autism phenotype versus registered diagnosis in Swedish children: prevalence trends over 10 years in general population samples*. bmj 350, h1961 (2015); Masi et al., *A comprehensive systematic review and meta-analysis of pharmacological and dietary supplement interventions in paediatric autism: moderators of treatment response and recommendations for future research*. Psychol Med. (2017) 47:1323-34). Autism Spectrum Disorder (ASD) comprises a broad group of diseases and syndromes that impact behavior, motor skills, cognitive development, motor skills, social interaction, communication, and behavior (Cawthorpe D. *Comprehensive description of comorbidity for autism spectrum disorder in a general population*. Perm J. (2017) 21:16-088). A 2018 report suggests that distress and lack of independence are a direct result of these functional impediments (Khalil et al., *Social decision making in autism: on the impact of mirror neurons, motor control, and imitative behaviors*. CNS Neurosci Ther. (2018) 24:669-76).

Although there are a few approved drugs for the mitigation of ASD symptoms with a narrow range of effectiveness, to date, families and patient with ASD have limited to no effective therapeutic options with measurable result on improved quality of life and social interaction (D'Agati et al. *Treatment of severe self-injurious behavior in autism spectrum disorder by neuromodulation*. J ECT. (2017) 33:7-11; Bang et al. *Herbal medicine treatment for children with autism spectrum disorder: a systematic review*. Evid Based Complement Alternat Med. (2017) 2017:8614680; Eapen et al., *Current status of biological treatment options in autism spectrum disorder*. Asian J Psychiatr. (2017) 30:1-10). Moreover, the available options present with notable and serious side effects (Fung et al. *Pharmacologic treatment of severe irritability and problem behaviors in autism: a systematic review and meta-analysis*. Pediatrics. (2016) 137 (Suppl 2S):124-35). There is some published evidence for use of antipsychotic, antidepressant, or anxiolytic drugs for self-aggressive behavior associated with ASD (Fitzpatrick et al. *Aggression in autism spectrum disorder: presentation and treatment options*. Neuropsychiatr Dis Treat. (2016) 12:1525-38; Sahoo et al. *Effectiveness of clozapine for the treatment of psychosis and disruptive behaviour in a child with atypical autism: a case report and a brief review of the evidence*. Asian J Psychiatr. (2017) 29:194-5). In addition, a recent study suggest that antiepileptic drugs used for seizure control in ASD management may also improve sleep quality and modulate behavior (Hirota et al. *Antiepileptic medications in autism spectrum disorder: a systematic review and meta-analysis*. J Autism Dev Disord. (2014) 44:948-57). Nevertheless, none of these drugs has been reported to have significant impact on the quality of life of the patients and their families.

Thus, there is an unmet need for improved methods of treatment of ASD with various combinations of therapeutic agents that can reduce symptoms associated with autism and/or improve quality of life for treated individuals and their families. The present invention and methods provide these and/or other advantages to existing treatments. Results from a 2019 case study showed an improved behavior in 61% of the patients with ASD and severe behavioral problems based on caregivers' rankings. However, some of the patients also reported notable side effects such as loss of appetite, sleep disorders, and increased irritability in some cases. It is important to note that patients in this study used CBD rich medicines (Lundström et al., Autism phenotype versus registered diagnosis in Swedish children: prevalence trends over 10 years in general population samples. bmj 350, h1961 (2015)). A similar observational study investigated the effect of CBD-rich *Cannabis* oil with a small amount of THC on children with ASD and followed for six months. Over 80% of the observed patients reported improvement in restlessness, rage attacks, and agitation. Good quality of life was reported by 67% at the six-month assessment (Masi et al. A comprehensive systematic review and meta-analysis of pharmacological and dietary supplement interventions in pediatric autism: moderators of treatment response and recommendations for future research. Psychol Med. (2017) 47:1323-34).

II. Definitions

The term "a" or "an" refers to one or more of that entity, i.e., can refer to a plural referent. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

Throughout this application, the term "about" is used to indicate that a value includes the inherent variation of error for the device or the method being employed to determine the value, or the variation that exists among the samples being measured. Unless otherwise stated or otherwise evident from the context, the term "about" means within 10% (i.e., within 10%, 9%, 8%, 7%, 6%, 5%, 4%, 3%, 2%, 1%, or less) above or below the reported numerical value (except where such number would exceed 100% of a possible value). When used in conjunction with a range or series of values, the term "about" applies to the endpoints of the range or each of the values enumerated in the series, unless otherwise indicated. As used in this application, the terms "about" and "approximately" are used as equivalents.

Herein, the terms "comprise", or variations such as "comprises" or "comprising", will be understood to imply the inclusion of a stated element or integer or group of elements or integers but not the exclusion of any other element or integer or group of elements or integers.

The term "active ingredient" as used herein refers to a botanical drug substance derived from a *Cannabis* plant or a synthetic variant thereof that produces a desired biological effect. For example, active ingredients of the pharmaceutical compositions described herein include, but are not limited to, cannabinoids, phytocannabinoids (including THC and CBD), cannabinoic acids, terpenes, terpenoids, and cannabinoid receptor agnonists (including CB1 and CB2 agonists).

The term "active ingredient portion" as used herein refers to the portion of a composition that accounts for all active ingredients. In some embodiments, the active ingredient portion of the pharmaceutical compositions described herein comprises one or more active ingredients. For example, the active ingredient portion may include one or more substantially pure active ingredients, one or more enriched active ingredients, or mixtures thereof. In some embodiments, the active ingredient portion comprises one or more active ingredients and one or more additional active ingredients that are not derived from a *Cannabis* plant, such as one or more other drugs.

The terms "administer," "administering" or "administration" as used herein refer to either directly administering a compound or pharmaceutically acceptable salt or ester of the compound or a composition comprising the compound or pharmaceutically acceptable salt or ester of the compound to a subject.

The term "adverse event" (AE) as used herein is defined as any untoward medical occurrence in a clinical investigation patient reported on or after the first screening date. An AE does not necessarily have to have a causal relationship with the treatment. An AE can therefore be any unfavorable and unintended sign (including an abnormal laboratory finding), symptom whether or not related to the medicinal (investigational) product, or disease temporally associated with the use of a medicinal (investigational) product. Typical adverse events include nausea, vomiting, somnolence, dizziness, and hallucination.

The term "botanical drug substance" as used herein refers to the definition provided in the Guidance for Industry Botanical Drug Products Draft Guidance, August 2000, US Department of Health and Human Services, Food and Drug Administration Centre for Drug Evaluation and Research of: "A drug substance derived from one or more plants, algae, or macroscopic fungi. It is prepared from botanical raw materials by one or more of the following processes: pulverization, decoction, expression, aqueous extraction, ethanolic extraction, or other similar processes."

The term "*Cannabis* plant(s)" encompasses wild type *Cannabis sativa* and also variants thereof, including *Cannabis* chemovars which naturally contain different amounts of the individual cannabinoids, *Cannabis sativa* subspecies *indica* including the variants var. *indica* and var. *kafiristanica*, *Cannabis indica* and also plants which are the result of genetic crosses, self-crosses or hybrids thereof. The term "*Cannabis* plant material" is to be interpreted accordingly as encompassing plant material derived from one or more *Cannabis* plants. For the avoidance of doubt it is hereby stated that "*Cannabis* plant material" includes dried *Cannabis* biomass.

The term "carrier" as used herein encompasses carriers, excipients, and diluents, meaning a material, composition or vehicle, such as a liquid or solid filler, diluent, excipient, solvent or encapsulating material involved in carrying or transporting a pharmaceutical agent from one organ, or portion of the body, to another organ or portion of the body.

As used herein, the term "cultivar" means a group of similar plants that by structural features and performance (i.e., morphological and physiological characteristics) can be identified from other varieties within the same species. Furthermore, the term "cultivar" variously refers to a variety, strain, or race of plant that has been produced by horticultural or agronomic techniques and is not normally found in wild populations. The terms cultivar, variety, strain and race are often used interchangeably by plant breeders, agronomists and farmers.

As used herein, the term "chemovar" means plants distinguished by the chemical compounds produced, rather than the morphological characteristics of the plant.

The term "effective amount" refers to the minimum amount of an agent or composition required to result in a particular physiological effect. The effective amount of a particular agent may be represented in a variety of ways based on the nature of the agent, such as mass/volume, # of cells/volume, particles/volume, (mass of the agent)/(mass of the subject), # of cells/(mass of subject), or particles/(mass of subject). The effective amount of a particular agent may also be expressed as the half-maximal effective concentration ($EC_{50}$), which refers to the concentration of an agent that results in a magnitude of a particular physiological response that is half-way between a reference level and a maximum response level.

The term "enriched" or "enriched active ingredient(s)" means preparations of any one of the active ingredients having a chromatographic purity (of the active ingredient) of greater than about 80%. In some embodiments, the chromatographic purity is greater than 85%. In some embodiments, the chromatographic purity is greater than about 90%. An enriched preparation of an active ingredient(s) will generally contain a greater proportion of impurities and/or other cannabinoids than a substantially pure preparation of the same active ingredient(s), as described below.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Plant material" is defined as a plant or plant part (e.g. bark, wood, leaves, stems, roots, flowers, fruits, seeds, berries or parts thereof) as well as exudates.

"Population" of cells refers to any number of cells greater than 1, but is preferably at least $1\times10^3$ cells, at least $1\times10^4$ cells, at least at least $1\times10^5$ cells, at least $1\times10^6$ cells, at least $1\times10^7$ cells, at least $1\times10^8$ cells, at least $1\times10^9$ cells, at least $1\times10^{10}$ cells, or more cells. A population of cells may refer to an in vitro population (e.g., a population of cells in culture) or an in vivo population (e.g., a population of cells residing in a particular tissue).

As used within the context of this application, the term "purified" means extracted, isolated, and/or separated from other compounds, formulations, compositions, matter, and/or mass.

The term "reference value" or "control value" refers to a value or measurement obtained from an experimental control group (e.g., vehicle treated or untreated control values) or to a baseline value obtained from a sample or subject before treatment that is then compared to a value obtained from the sample or subject after treatment.

The term "subject" includes animals, such as e.g. mammals. In some embodiments, the mammal is a primate. In some embodiments, the mammal is a human. In some embodiments, subjects are livestock such as cattle, sheep, goats, cows, swine, and the like; or domesticated animals such as dogs and cats. In some embodiments (e.g., particularly in research contexts) subjects are rodents (e.g., mice, rats, hamsters), rabbits, primates, or swine such as inbred pigs and the like. The terms "subject" and "patient" are used interchangeably herein.

The term "substantially pure" or "substantially pure active ingredient(s)" means preparations of any one of the active ingredients having a chromatographic purity (of the active ingredient) of greater than about 95%. In some embodiments, the chromatographic purity is greater than 96%. In some embodiments, the chromatographic purity is greater than about 97%. In some embodiments, the chromatographic purity is greater than about 98%. In some embodiments, the chromatographic purity is greater than about 99%. In some embodiments, the chromatographic purity is greater than about 99.5%.

"Treating" as used herein refers to delivering an agent or composition to a subject to affect a physiologic outcome.

As used herein, the term "winterizing" or "winterization" refers to the process by which plant lipids and waxes are removed from a Cannabis extract. Persons have skill in the art will immediately recognize how to winterize an extract. Briefly, winterization is the dissolving the Cannabis extract into a polar solvent (most commonly ethanol) at sub-zero temperatures. Doing so separates the waxes and lipids from the oil, forcing them to collect at the top of the mixture for easy filtration/collection. Typically, winterization is conducted by mixing ethanol and hash oil into a container and placing it into a sub-zero freezer.

III. Cannabis

Cannabis is a genus of flowering plants that includes three different species, Cannabis sativa, Cannabis indica and Cannabis ruderalis. There are 483 identifiable chemical constituents known to exist in the Cannabis plant (Rudolf Brenneisen (2007) in Marijuana and the Cannabinoids, ElSohly, ed.; incorporated herein by reference), and at least 85 different cannabinoids have been isolated from the plant (El-Alfy, Abir T, et al. (2010) Pharmacology Biochemistry and Behavior 95 (4): 434-42; incorporated herein by reference). Cannabis plants are categorized based on the overall amount of THC produced, and on the ratio of THC to CBD. Although overall cannabinoid production is influenced by environmental factors, the THC/CBD ratio is genetically determined and remains fixed throughout the life.

IV. Cannabinoids

Cannabis plants produce a unique family of terpeno-phenolic compounds called cannabinoids. Cannabinoids are a class of diverse chemical compounds that activate cannabinoid receptors in the human brain, peripheral nervous system, and immune system (Mackie K. (2008) J. Neuroendocrinol. May 20: 1:10-4). Cannabinoids can be broadly categorized into endocannabinoids, which are endogenously produced compounds in humans and other animals, such as 2-Arachidonoylglycerol, and phytocannabinoids, which are cannabinoid mimetic compounds produced by plants. Additionally, cannabinoids can be synthesized in a laboratory setting, referred to herein as "synthetic cannabinoids".

Cannabinoids are the most studied group of secondary metabolites in Cannabis. Most exist in two forms, as acids and in neutral (decarboxylated) forms. The acid form is designated by an "A" at the end of its acronym (i.e. THCA). The phytocannabinoids are synthesized in the plant as acid forms, and while some decarboxylation does occur in the plant, it increases significantly post-harvest and the kinetics increase at high temperatures. (Sanchez and Verpoorte 2008). The biologically active forms for human consumption are the neutral forms and all cannabinoids in their acid forms (those ending in "-A") can be converted to their non-acidic forms through a process called decarboxylation. While some decarboxylation (e.g., neutralization) of cannabinoids does occur in the plant, production of the neutral forms increase significantly post-harvest with increases in temperature. (Sanchez and Verpoorte (2008) Plant Cell Physiol. December: 49(12)). Therefore, decarboxylation is usually achieved by (optionally) thorough drying of the plant material followed by heating it, often by combustion, vaporization, heating, or baking in an oven. Cannabinoid compositions can similarly be decarboxylated by being exposed to heat. Decarboxylation is usually achieved by thorough drying of the plant material followed by heating it, often by either combustion, vaporization, or heating or baking in an oven. Unless otherwise noted, references to cannabinoids in this disclosure refer to the "active" decarboxylated versions of the molecules (e.g., CBD or THC).

Typical cannabinoids isolated from Cannabis plants include, but are not limited to, Cannabigerolic Acid (CBGA), Cannabigerolic Acid monomethylether (CBGAM), Cannabigerol (CBG), Cannabigerol monomethylether (CBGM), Cannabigerovarinic Acid (CBGVA), Cannabigerovarin (CBGV), Cannabichromenic Acid (CBCA), Cannabichromene (CBC), Cannabichromevarinic Acid (CBCVA), Cannabichromevarin (CBCV), Cannabidiolic Acid (CBDA), Cannabidiol (CBD), Cannabidiol monomethylether (CBDM), Cannabidiol-$C_4$ (CBD-$C_4$), Cannabidivarinic Acid (CBDVA), Cannabidivarin (CBDV), Cannabidiorcol (CBD-$C_1$), Tetrahydrocannabinolic acid A (THCA-A), Tetrahydrocannabinolic acid B (THCA-B), Tetrahydrocannabinolic Acid (THCA), Tetrahydrocannabinol (THC), Tetrahydrocannabinolic acid $C_4$ (THCA-$C_4$), Tetrahydrocannbinol $C_4$(THC-$C_4$), Tetrahydrocannabivarinic acid (THCVA), Tetrahydrocannabivarin (THCV), Tetrahydrocannabiorcolic acid (THCA-$C_4$), Tetrahydrocannabiorcol (THC-$C_1$), $\Delta^7$-cis-iso-tetrahydrocannabivarin, $\Delta^8$-tetrahydrocannabinolic acid ($\Delta$8-THCA), Cannabivarinodiolic (CBNDVA), Cannabivarinodiol (CBNDV), $\Delta^8$-tetrahydrocannabinol ($\Delta^8$-THC), $\Delta^9$-tetrahydrocannabinol ($\Delta^9$-THC), Cannabicyclolic acid (CBLA), Cannabicyclol (CBL), Cannabicyclovarin (CBLV), Cannabielsoic acid A (CBEA-A), Cannabielsoic acid B (CBEA-B), Cannabielsoin (CBE), Cannabivarinselsoin (CBEV), Cannabivarinselsoinic Acid (CBEVA), Cannabielsoic Acid (CBEA), Cannabielvarinsoin (CBLV), Cannabielvarinsoinic Acid (CBLVA), Cannabinolic acid (CBNA), Cannabinol (CBN), Cannabivarinic Acid (CBNVA), Cannabinol methylether (CBNM), Cannabinol-$C_4$ (CBN-$C_4$), Cannabivarin (CBV), Cannabino-$C_2$ (CBN-$C_2$), Cannabiorcol (CBN-$C_1$), Cannabinodiol (CBND), Cannabinodiolic Acid (CBNDA), Cannabinodivarin (CBDV), Cannabitriol (CBT), 10-Ethoxy-9-hydroxy-$\Delta^{6a}$-tetrahydrocannabinol, 8,9-Dihydroxy-$\Delta^{6a(10a)}$-tetrahydrocannabinol (8,9-Di-OH-CBT-$C_5$), Cannabitriolvarin (CBTV), Ethoxycannabitriolvarin (CBTVE), Dehydrocannabifuran (DCBF), Cannbifuran (CBF), Cannabichromanon (CBCN), Cannabicitran (CBT), 10-Oxo-$\Delta^{6a(10a)}$-tetrahydrocannabinol (OTHC), $\Delta^9$-cis-tetrahydrocannabinol (cis-THC), Cannabiripsol (CBR), 3,4,5,6-tetrahydro-7-hydroxy-alpha-alpha-2-trimethyl-9-n-propyl-2,6-methano-2H-1-benzoxocin-5-methanol (OH-iso-HHCV), Trihydroxy-delta-9-tetrahydrocannabinol (triOH-THC), Yangonin, Epigallocatechin gallate, Dodeca-2E, 4E, 8Z, 10Z-tetraenoic acid isobutylamide, and Dodeca-2E,4E-dienoic acid isobutylamide. See Holley et al. (1975) *J. Pharm. Sci.* 64:892-894 and De Zeeuw et al. (9172) Science 175:778-779, each of which is herein incorporated by reference in its entirety for all purposes.

Brief descriptions and chemical structures for several of the major cannabinoids are provided below.

Tetrahydrocannabinol

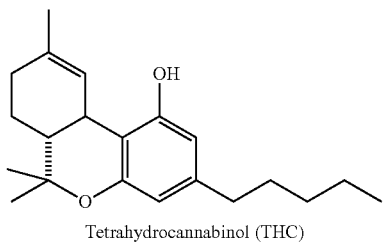

Tetrahydrocannabinol (THC)

Known as delta-9-tetrahydrocannabinol ($\Delta 9$-THC), THC is the principal psychoactive constituent (or cannabinoid) of the *Cannabis* plant. The initially synthesized and accumulated form in plant is THC acid (THCA). THC has mild to moderate analgesic effects, and *Cannabis* can be used to treat pain by altering transmitter release on dorsal root ganglion of the spinal cord and in the periaqueductal gray. Other effects include relaxation, alteration of visual, auditory, and olfactory senses, fatigue, and appetite stimulation. THC has marked antiemetic properties, and may also reduce aggression in certain subjects (Hoaken (2003) *Addictive Behaviors* 28: 1533-1554).

The pharmacological actions of THC result from its partial agonist activity at the cannabinoid receptor CB1, located mainly in the central nervous system, and the CB2 receptor, mainly expressed in cells of the immune system (Pertwee, (2006) *International Journal of Obesity* 30: S13-S18.) It is also suggested that THC has an anticholinesterase action, which may implicate it as a potential treatment for Alzheimer's and Myasthenia gravis (Eubanks et al., (2006) *Molecular Pharmaceutics* 3 (6): 773-7).

In the *Cannabis* plant, THC occurs mainly as tetrahydrocannabinolic acid (THCA, 2-COOH-THC). Geranyl pyrophosphate and olivetolic acid react, catalyzed by an enzyme to produce cannabigerolic acid, which is cyclized by the enzyme THC acid synthase to give THCA. Over time, or when heated, THCA is decarboxylated producing THC. The pathway for THCA biosynthesis is similar to that which produces the bitter acid humulone in hops. See Fellermeier et al., (1998) *FEBS Letters* 427 (2): 283-5); de Meijer et al. I, II, III, and IV (I: 2003, Genetics, 163:335-346; II: 2005, *Euphytica*, 145:189-198; III: 2009, *Euphytica*, 165:293-311; and IV: 2009, *Euphytica*, 168:95-112).

Non-limiting examples of THC variants include $\Delta^9$-THC-$C_5$, $\Delta^9$-THC-$C_4$, $\Delta^9$-THCV-$C_3$, $\Delta^9$-THCO-$C_1$, $\Delta^9$-THCA-$C_5$ A, $\Delta^9$-THCA-$C_5$ B, $\Delta^9$-THCA-$C_4$ A, $\Delta^9$-THCA-$C_4$ B, $\Delta^9$-THCVA-$C_3$ A, $\Delta^9$-THCOA-$C_1$ A, $\Delta^9$-THCOA-$C_1$ B, $\Delta^8$-THC-$C_5$, $\Delta^8$-THCA-$C_5$ A, (–)-cis-$\Delta^9$-THC-$C_5$.

Cannabidiol

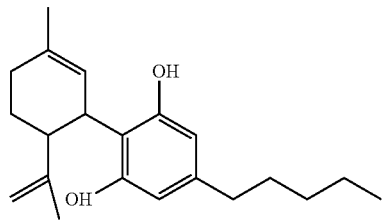

Cannabidiol (CBD)

CBD is a cannabinoid found in *Cannabis* shown to display sedative effects in animal tests (Pickens, (1981) *Br. J. Pharmacol.* 72 (4): 649-56). Some research, however, indicates that CBD can increase alertness, and attenuate the memory-impairing effect of THC. (Nicholson et al., June (2004) *J Clin Psychopharmacol* 24 (3): 305-13; Morgan et al., (2010) *The British Journal of Psychiatry*, 197:258-290). It may decrease the rate of THC clearance from the body, perhaps by interfering with the metabolism of THC in the liver. Medically, it has been shown to relieve convulsion, inflammation, anxiety, and nausea, as well as inhibit cancer cell growth (Mechoulam, et al., 2007, *Chemistry & Biodiversity* 4 (8): 1678-1692), for example reducing growth and invasiveness of aggressive human breast cancer cells (McAllister et al., 2007, *Mol. Cancer Ther.* 6 (11): 2921-7) Recent studies have also shown CBD to be as effective as atypical antipsychotics in treating schizophrenia (Zuardi et al., 2006, *Braz. J. Med. Biol. Res.* 39 (4): 421-429), and studies also suggests that it may relieve symptoms of dystonia (Consroe, 1986, *The International journal of neuroscience* 30 (4): 277-282).

*Cannabis* produces CBD-carboxylic acid through the same metabolic pathway as THC, until the last step, where CBDA synthase performs catalysis instead of THCA synthase. See Marks et al. (2009) Journal of Experimental Botany 60 (13): 3715-3726) and Meijer et al. I, II, III, and IV.

Non-limiting examples of CBD variants include CBD-$C_5$, CBDM-$C_5$, CBD-$C_4$, CBDV-$C_3$, CBD-$C_1$, CBDA-$C_5$, and CBDVA-$C_3$.

Cannabigerol

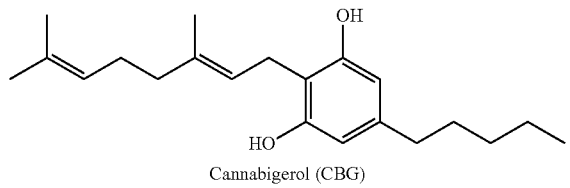

Cannabigerol (CBG)

CBG is a non-psychoactive cannabinoid found in the *Cannabis* genus of plants. Cannabigerol has been found to act as a high affinity α2-adrenergic receptor agonist, moderate affinity 5-HT1A receptor antagonist, and low affinity CB1 receptor antagonist. It also binds to the CB2 receptor. Cannabigerol has also been shown to reduce depression in animal models (US Patent Application Publication No. 2008-0031977). In particular CBG has been shown to have significant potential applications in the treatment of glaucoma, depression, Huntington's disease, MRSA, cachexia, and cancer (Craig et al. 1984, Experimental eye research 39 (3):251-259; U.S. Pat. No. 8,481,085; Valdeolivas et al. 2015, Neurotherapeutics January 12(1):185-99; Appendino G et al., 2008, J. Nat Prod. August:71(8):1427-30; Borrelli F et al. 2013, Biochem Pharmacol May 1:85(9):1306-16; Borrelli F. et al. 2014, Carcinogenesis December:35(12): 2787-97) Non-limiting examples of CBG variants include (E)-CBG-$C_5$, (E)-CBGM-$C_5$ A, (Z)-CBGA-$C_5$ A, (E)-CBGV-$C_3$, (E)-CBGA-$C_5$ A, (E)-CBGAM-$C_5$ A, and (E)-CBGVA-$C_3$ A.

Cannabinol

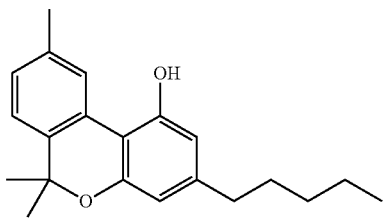

Cannabinol (CBN)

CBN is a mildly to non-psychoactive substance cannabinoid found in *Cannabis sativa* and *Cannabis indica/afghanica*. It is also a metabolite of tetrahydrocannabinol (THC). CBN acts as a weak agonist of the CB1 and CB2 receptors, with lower affinity in comparison to THC. Non-limiting examples of CBN variants include CBN-$C_5$, CBN-$C_4$, CBN-$C_3$, CBN-$C_2$, CBN-$C_1$, CBNA-$C_5$ A, and CBNM-$C_5$.

Cannabichromene

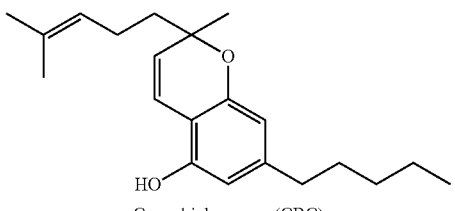

Cannabichromene (CBC)

CBC bears structural similarity to the other natural cannabinoids, including tetrahydrocannabinol, tetrahydrocannabivarin, cannabidiol, and cannabinol, among others. Evidence has suggested that it may play a role in the anti-inflammatory and anti-viral effects of *Cannabis*, and may contribute to the overall analgesic effects of *Cannabis*. Non-limiting examples of CBC variants include CBC-$C_5$, CBCA-$C_5$ A, CBCV-$C_3$, and CBCVA-$C_3$ A.

Cannabivarin

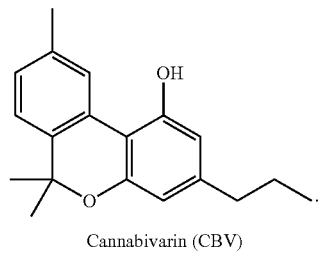

Cannabivarin (CBV)

Cannabivarin, also known as cannabivarol or CBV, is a non-psychoactive cannabinoid found in minor amounts in the hemp plant *Cannabis sativa*. It is an analog of cannabinol (CBN) with the side chain shortened by two methylene bridges (—CH2-). CBV is an oxidation product of tetrahydrocannabivarin (THCV, THV).

Cannabidivarin

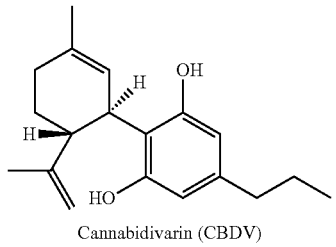

Cannabidivarin (CBDV)

CBDV is a non-psychoactive cannabinoid found in *Cannabis*. It is a homolog of cannabidiol (CBD), with the side-chain shortened by two methylene bridges (CH2 units). Cannabidivarin has been found reduce the number and severity of seizures in animal models (U.S. patent application Ser. No. 13/075,873). Plants with relatively high levels of CBDV have been reported in feral populations of *C. indica* (=*C. sativa* ssp. *indica* var. *kafiristanica*) from northwest India, and in hashish from Nepal.

Tetrahydrocannabivarin

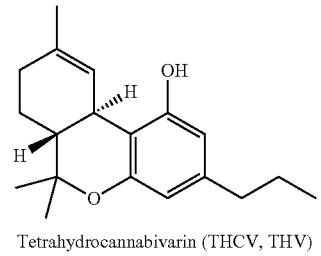

Tetrahydrocannabivarin (THCV, THV)

THCV, or THV is a homologue of tetrahydrocannabinol (THC) having a propyl (3-carbon) side chain. This terpenophenolic compound is found naturally in Cannabis, sometimes in significant amounts. Plants with elevated levels of propyl cannabinoids (including THCV) have been found in populations of Cannabis sativa L. ssp. indica (=Cannabis indica Lam.) from China, India, Nepal, Thailand, Afghanistan, and Pakistan, as well as southern and western Africa. THCV has been shown to be a CB1 receptor antagonist, i.e. it blocks the effects of THC. Tetrahydrocannabinol has been shown to increase metabolism, help weight loss and lower cholesterol in animal models (U.S. patent application Ser. No. 11/667,860).

Cannabicyclol

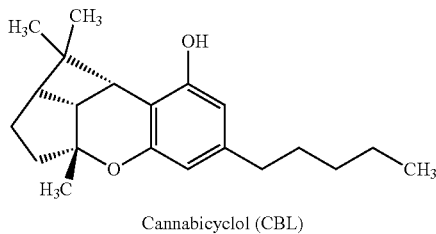

Cannabicyclol (CBL)

Cannabicyclol (CBL) is a non-psychotomimetic cannabinoid found in the Cannabis species. CBL is a degradative product like cannabinol. Light converts cannabichromene to CBL. Non-limiting examples of CBL variants include CBL-$C_5$, CBLA-$C_5$ A, and CBLV-$C_3$.

Cannabitriol

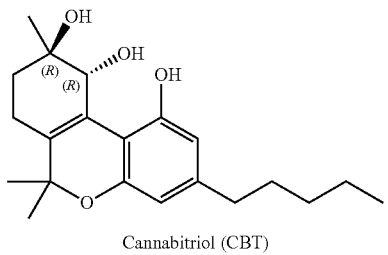

Cannabitriol (CBT)

Non-limiting examples of CBT include (−)-trans-CBT-$C_5$, (+)-trans-CBT-$C_5$, (±)-trans-CBT-$C_5$, (−)-trans-CBT-OEt-$C_5$, (±)-trans-CBT-$C_3$, 8,9-Di-OH-CBT-$C_5$, CBDA-$C_5$ 9-OH-CBT-$C_5$ ester, Cannabiripsol-$C_5$, (−)-Cannabitetrol, and OTHC.

Cannabielsoin-type

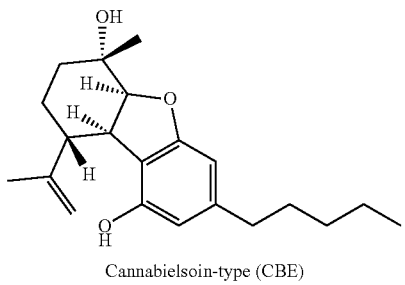

Cannabielsoin-type (CBE)

Non-limiting examples of CBE variants include CBE-$C_5$, CBE-$C_3$, CBEA-$C_5$ A, CBEA-$C_5$ B, CBEA-$C_3$ B, OH-iso-HHCV-$C_3$, DCBF-$C_5$, and CBF-$C_5$.

Cannabinoid Biosynthesis

The biosynthetic pathway of cannabinoids has been studied in great detail. According to the current model, phenolic precursors such as geranyl pyrophosphate (GPP) and polyketide, olivetolic acid (OA) are condensed by geranyl pyrophosphate olivetolate geranyl transferase (GOT) to form cannabigerolic acid (CBGA). Alternatively, GPP and divarinic acid can be condensed by GOT to form cannabigerovarinic acid (CBGVA). CBGA or CBGVA are considered to be the "primary cannabinoids" from which others can be produced.

CBGA/CBGVA is quickly transformed in plants into, for example: (1) CBCA/CBCVA by CBCA synthase; (2) THCA/THCVA by THCA synthase; or (3) CBDA/CBDVA by CBDA synthase. The genes coding for THCA synthase and CBDA synthase are found on the same B locus. Thus Cannabis plants can be categorized into THC-CBD chemotypes based on the state of the B locus BT/BT (THC producing, chemotype I), BD/BD (CBD producing, chemotype III), and BT/BD (producing both THC and CBD, chemotype II). Additional information on the genetic regulation of cannabinoids can be found in de Meijer et al. I, II, III, and IV (I: 2003, Genetics, 163:335-346; II: 2005, Euphytica, 145:189-198; III: 2009, Euphytica, 165:293-311; and IV: 2009, Euphytica, 168:95-112). The BT and BD alleles are known, and can be easily detected using methods known to those skilled in the art, including Northerns, PCR, or sequencing. A representative sequence of THCA synthase is available at GenBank ID AB057805.1. A representative sequence of the CBDA synthase is available at GenBank ID AB292682.1.

V. Terpenes and Terpenoids

In addition to cannabinoids, Cannabis also produces over 120 different terpenes (Russo (2011) British Journal of Pharmacology, 163:1344-1364). Within the context and verbiage of this document the terms 'terpenoid' and 'terpene' are used interchangeably. In some embodiments, the present disclosure provides pharmaceutical compositions comprising one or more terpenes or terpenoids.

In addition to many circulatory and muscular effects, some terpenes interact with neurological receptors. A few terpenes produced by Cannabis plants also bind weakly to cannabinoid receptors. Some terpenes can alter the permeability of cell membranes and allow in either more or less THC, while other terpenes can affect serotonin and dopamine chemistry as neurotransmitters. Terpenoids are lipophilic, and can interact with lipid membranes, ion channels, a variety of different receptors (including both G-protein coupled odorant and neurotransmitter receptors), and enzymes. Some are capable of absorption through human skin and passing the blood brain barrier.

Terpenes are derived biosynthetically from units of isoprene, which have the molecular formula $C_5H_8$. The basic molecular formulae of terpenes are multiples of $(C_5H_8)_n$ where n is the number of linked isoprene units. The isoprene units may be linked together "head to tail" to form linear chains or they may be arranged to form rings. In one embodiment, the purified terpene is chosen from Limonene, Nerolidol, Beta-Myrcene, Linalool, Alpha-Caryophyllene, Beta-Caryophyllene, Alpha-Pinene, Beta-Pinene, Alpha-Bisabolol, Delta-3-Carene, Borneol, p-Cymene, Eucalyptol, Alpha-Humulene, Alpha-Terpineol, Terpinolene, Pulegone, Camphene, or Geraniol. Within the context of this disclosure, the term "terpene" includes Hemiterpenes, Monoterpenols, Terpene esters, Diterpenes, Monoterpenes, Polyterpenes, Tetraterpenes, Terpenoid oxides, Sesterterpenes, Sesquiterpenes, Norisoprenoids, as well as their isomers, enantiomers, or derivatives. Within the context of this disclosure, the term terpene includes the α-(alpha), β-(beta), γ-(gamma), oxo-, isomers, or any combinations thereof.

Examples of terpenes within the context of this disclosure include: 7,8-dihydro-alpha-ionone, 7,8-dihydro-beta-ionone, Acetanisole, Acetic Acid, Acetyl Cedrene, Anethole, Anisole, Benzaldehyde, Bergamotene (Alpha-cis-Bergamotene) (Alpha-trans-Bergamotene), Bisabolol (Beta-Bisabolol), Alpha Bisabolol, Borneol, Bornyl Acetate, Butanoic/Butyric Acid, Cadinene (Alpha-Cadinene) (Gamma-Cadinene), Cafestol, Caffeic acid, Camphene, Camphor, Capsaicin, Carene (Delta-3-Carene), Carotene, Carvacrol, Dextro-Carvone, Laevo-Carvone, Alpha-Caryophyllene, Beta-Caryophyllene, Caryophyllene oxide, Cedrene (Alpha-Cedrene) (Beta-Cedrene), Cedrene Epoxide (Alpha-Cedrene Epoxide), Cedrol, Cembrene, Chlorogenic Acid, Cinnamaldehyde, Alpha-amyl-Cinnamaldehyde, Alpha-hexyl-Cinnamaldehyde, Cinnamic Acid, Cinnamyl Alcohol, Citronellal, Citronellol, Cryptone, Curcumene (Alpha-Curcumene) (Gamma-Curcumene), Decanal, Dehydrovomifoliol, Diallyl Disulfide, Dihydroactinidiolide, Dimethyl Disulfide, Eicosane/Icosane, Elemene (Beta-Elemene), Estragole, Ethyl acetate, Ethyl Cinnamate, Ethyl maltol, Eucalyptol/1,8-Cineole, Eudesmol (Alpha-Eudesmol) (Beta-Eudesmol) (Gamma-Eudesmol), Eugenol, Euphol, Farnesene, Farnesol, Fenchol (Beta-Fenchol), Fenchone, Geraniol, Geranyl acetate, Germacrenes, Germacrene B, Guaia-1(10),11-diene, Guaiacol, Guaiene (Alpha-Guaiene), Gurjunene (Alpha-Gurjunene), Herniarin, Hexanaldehyde, Hexanoic Acid, Humulene (Alpha-Humulene) (Beta-Humulene), Ionol (3-oxo-alpha-ionol) (Beta-Ionol), Ionone (Alpha-Ionone) (Beta-Ionone), Ipsdienol, Isoamyl Acetate, Isoamyl Alcohol, Isoamyl Formate, Isoborneol, Isomyrcenol, Isopulegol, Isovaleric Acid, Isoprene, Kahweol, Lavandulol, Limonene, Gamma-Linolenic Acid, Linalool, Longifolene, Alpha-Longipinene, Lycopene, Menthol, Methyl butyrate, 3-Mercapto-2-Methylpentanal, Mercaptan/Thiols, Beta-Mercaptoethanol, Mercaptoacetic Acid, Allyl Mercaptan, Benzyl Mercaptan, Butyl Mercaptan, Ethyl Mercaptan, Methyl Mercaptan, Furfuryl Mercaptan, Ethylene Mercaptan, Propyl Mercaptan, Thenyl Mercaptan, Methyl Salicylate, Methylbutenol, Methyl-2-Methylvalerate, Methyl Thiobutyrate, Myrcene (Beta-Myrcene), Gamma-Muurolene, Nepetalactone, Nerol, Nerolidol, Neryl acetate, Nonanaldehyde, Nonanoic Acid, Ocimene, Octanal, Octanoic Acid, P-Cymene, Pentyl butyrate, Phellandrene, Phenylacetaldehyde, Phenylethanethiol, Phenylacetic Acid, Phytol, Pinene, Beta-Pinene, Propanethiol, Pristimerin, Pulegone, Quercetin, Retinol, Rutin, Sabinene, Sabinene Hydrate, cis-Sabinene Hydrate, trans-Sabinene Hydrate, Safranal, Alpha-Selinene, Alpha-Sinensal, Beta-Sinensal, Beta-Sitosterol, Squalene, Taxadiene, Terpin hydrate, Terpineol, Terpine-4-ol, Alpha-Terpinene, Gamma-Terpinene, Terpinolene, Thiophenol, Thujone, Thymol, Alpha-Tocopherol, Tonka Undecanone, Undecanal, Valeraldehyde/Pentanal, Verdoxan, Alpha-Ylangene, Umbelliferone, or Vanillin.

Derivatives of terpenes include terpenoids, hemiterpenoids, monoterpenoids, sesquiterpenoids, sesterterpenoid, sesquarterpenoids, tetraterpenoids, triterpenoids, tetraterpenoids, polyterpenoids, isoprenoids, and steroids. Terpenoids, a.k.a. isoprenoids, are a large and diverse class of naturally occurring organic chemicals similar to terpenes, derived from five-carbon isoprene units assembled and modified in thousands of ways. Non-limiting examples of terpenoids include, Hemiterpenoids, 1 isoprene unit (5 carbons); Monoterpenoids, 2 isoprene units (10C); Sesquiterpenoids, 3 isoprene units (15C); Diterpenoids, 4 isoprene units (20C) (e.g. ginkgolides); Sesterterpenoids, 5 isoprene units (25C); Triterpenoids, 6 isoprene units (30C) (e.g. sterols); Tetraterpenoids, 8 isoprene units (40C) (e.g. carotenoids); and Polyterpenoid with a larger number of isoprene units.

Limonene

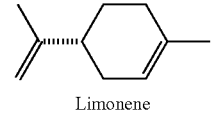

Limonene

D-Limonene, also known as limonene, is a monoterpenoid that is widely distributed in nature and often associated with citrus. It has strong anxiolytic properties in both mice and humans, apparently increasing serotonin and dopamine in mouse brain. D-limonene has potent antidepressant activity when inhaled. It is also under investigation for a variety of different cancer treatments, with some focus on its hepatic metabolite, perillic acid. There is evidence for activity in the treatment of dermatophytes and gastro-oesophageal reflux, as well as having general radical scavenging properties (Russo 2011, *British Journal of Pharmacology*, 163:1344-1364).

Valencene

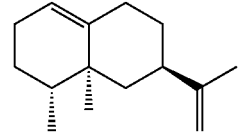

Valencene

Valencene is a sesquiterpene that is an aroma component of citrus fruit and citrus-derived odorants. It is obtained inexpensively from Valencia oranges. It has been shown to be anti-inflammatory and lower the levels of inflammatory markers in the white blood cells of the immune system (Tsoyi et al., J Enthnopharmacol. 2011, 11; 137(3):1311-7). Valencene is also a bronchodilator, which aides in oxygenation and can help promote cognitive function (Ertas et al., Nat Prod Res. 2014; 28(17):1405-8).

Eucalyptol

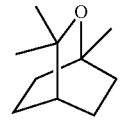

Eucalyptol

Eucalyptol is a monoterpenoid and is also known by a variety of synonyms: 1,8-cineol, 1,8-cineole, cajeputol, 1,8-epoxy-p-menthane, 1,8-oxido-p-menthane, eucalyptol, eucalyptole, 1,3,3-trimethyl-2-oxabicyclo[2.2.2]octane, cineol, and cineole. Eucalyptol has a fresh mint-like smell and a spicy, cooling taste. It is insoluble in water, but miscible with ether, ethanol, and chloroform. Eucalyptol is anti-inflammatory, anti-oxidant and neuroprotective (Seol et al., Adv Exp Med Biol. 2016; 929:389-398). This terpene may improve memory and positively influences cognitive abilities. Research has shown eucalyptol to be a potential treatment for Alzheimer's, as it lowered the inflammation caused by amyloid beta plaques (Khan et al., Neurochem Res. 2014. 39(2):344-52).

α-Bisabolol

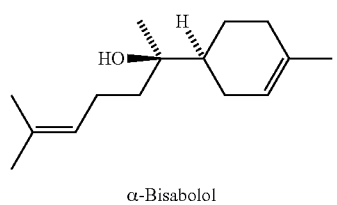

α-Bisabolol

α-Bisabolol is a natural monocyclic sesquiterpene alcohol present in the Chamomile flower (Miraj et al., Electron Physician. 2016. 20; 8(9):3024-3031), and provides soothing analgesic effects with anti-inflammatory (Leite Gde et al., Fioterapia. 2011, 82(2):208-11) and antioxidant properties (Braga et al., Pharmacology. 2009; 83(2):110-5).

Myrcene

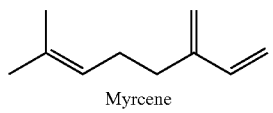

Myrcene

Myrcene is a monoterpenoid also found in *Cannabis*, and has a variety of pharmacological effects. It is often associated with a sweet fruit like taste. It reduces inflammation, aids sleep, and blocks hepatic carcinogenesis, as well as acting as an analgesic and muscle relaxant in mice. When β-myrcene is combined with Δ9-THC it may intensify the sedative effects of Δ9-THC, causing the well-known "couch-lock" effect that some *Cannabis* users experience (Russo 2011, *British Journal of Pharmacology*, 163:1344-1364).

Linalool

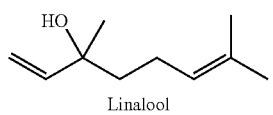

Linalool

D-Linalool, also known as linalool, is a monoterpenoid with very well-known anxiolytic effects. It is often associated with lavender, and frequented used in aromatherapy for its sedative impact. It acts as a local anesthetic and helps to prevent scarring from burns, is anti-nociceptive in mice, and shows anti-glutamatergic and anticonvulsant activity. Its effects on glutamate and GABA neurotransmitter systems are credited with giving it its sedative, anxiolytic, and anticonvulsant activities (Russo 2011, *British Journal of Pharmacology*, 163:1344-1364).

α-Pinene

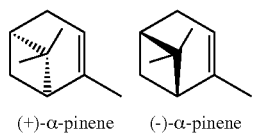

(+)-α-pinene    (-)-α-pinene

α-Pinene is a monoterpene common in nature, also with a plethora of effects on mammals and humans. It acts as an acetylcholinesterase inhibitor, which aids memory and counteracts the short-term memory loss associated with Δ$^9$-THC intoxication, is an effective antibiotic agent, and shows some activity against MRSA. In addition, α-pinene is a bronchodilator in humans and has anti-inflammatory properties via the prostaglandin E-1 pathway (Russo 2011, *British Journal of Pharmacology*, 163:1344-1364).

β-Caryophyllene

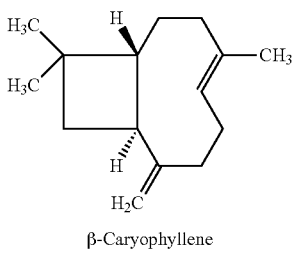

β-Caryophyllene

β-Caryophyllene (BCP) is often the most predominant sesquiterpenoid in *Cannabis*. It is less volatile than the monoterpenoids, thus it is found in higher concentrations in material that has been processed by heat to aid in decarboxylation. It is very interesting in that it is a selective full agonist at the CB2 receptor, which makes it the only phytocannabinoid found outside the *Cannabis* genus. In addition, it has anti-inflammatory and gastric cytoprotective properties, and may even have anti-malarial activity.

Caryophyllene oxide

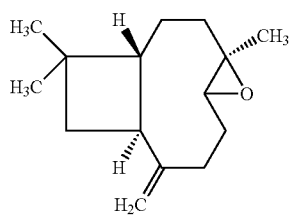

Caryophyllene oxide

Caryophyllene oxide is another sesquiterpenoid found in *Cannabis*, which has antifungal and anti-platelet aggregation properties (Russo 2011, *British Journal of Pharmacology*, 163:1344-1364).

Nerolidol

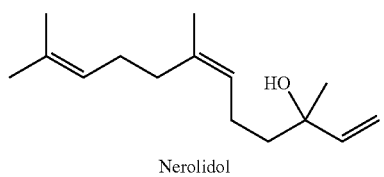

Nerolidol

Nerolidol is a sesquiterpene that is often found in citrus peels that exhibits a range of interesting properties. It acts as a sedative, inhibits fungal growth, and has potent antimalarial and antileishmanial activity. It also alleviated colon adenomas in rats (Russo 2011, *British Journal of Pharmacology*, 163:1344-1364).

Terpene Biosynthesis

Terpenoids are mainly synthesized in two metabolic pathways: mevalonic acid pathway (a.k.a. HMG-CoA reductase pathway, which takes place in the cytosol) and MEP/DOXP pathway (a.k.a. The 2-C-methyl-D-erythritol 4-phosphate/1-deoxy-D-xylulose 5-phosphate pathway, non-mevalonate pathway, or mevalonic acid-independent pathway, which takes place in plastids). Geranyl pyrophosphate (GPP), which is used by *Cannabis* plants to produce cannabinoids, is formed by condensation of dimethylallyl pyrophosphate (DMAPP) and isopentenyl pyrophosphate (IPP) via the catalysis of GPP synthase. Alternatively, DMAPP and IPP are ligated by FPP synthase to produce farnesyl pyrophosphate (FPP), which can be used to produce sesquiterpenoids. Geranyl pyrophosphate (GPP) can also be converted into monoterpenoids by limonene synthase.

VI. *Cannabis* Extracts

Extraction Methods

THC and CBD used in the compositions of the present disclosure can be obtained from any source of cannabinoids, including commercial sources for pure cannabinoids or raw *Cannabis* extracts.

In some embodiments, the THC and CBD cannabinoids are extracted. Botanical drug substances (BDS) can be extracted from starting plant materials according to methods known in the art. For example, suitable extraction methods include maceration, percolation, solvent extraction, steam distillation (giving you essential oil) or vaporization. General protocols for the preparation of botanical drug substances from *Cannabis* plant material are described in U.S. Pat. Nos. 8,603,515 and 9,730,911, both incorporated by reference herein.

Solvent extraction may be carried out using essentially any solvent that dissolves cannabinoids/cannabinoid acids, such as for example C1 to C5 alcohols (e.g. ethanol, methanol), C5-C12 alkanes (e.g. hexane), Norflurane (HFA134a), HFA227, and carbon dioxide. When solvents such as those listed above are used, the resultant primary extract typically contains non-specific lipid-soluble material or "ballast" e.g. waxes, wax esters and glycerides, unsaturated fatty acid residues, terpenes, carotenes, and flavonoids. The primary extract may be further purified for example by "winterization", which involves chilling to −20° C. followed by filtration to remove waxy ballast. In some embodiments, the primary extract can also be further purified by supercritical or subcritical extraction, vaporization, distillation, and chromatography.

In some embodiments, the botanical drug substance may be obtained by carbon dioxide ($CO_2$) extraction followed by a secondary extraction, e.g. an ethanolic precipitation, to remove a substantial proportion of non-cannabinoid materials. In some embodiments, the botanical drug substance is produced by a process comprising extraction with liquid $CO_2$ under sub-critical or super-critical conditions, and then a further extraction (e.g., an ethanolic precipitation) to remove significant amounts of ballast. If it is intended to prepare free cannabinoids from the *Cannabis* plant material, then the material is preferably heated to a defined temperature for a defined period of time in order to decarboxylate cannabinoid acids to free cannabinoids prior to extraction of the botanical drug substance.

In some embodiments, the botanical drug substance is prepared according to a process comprising the following steps: i) optional decarboxylation of the plant material, ii) extraction with liquid $CO_2$ (in some embodiments under sub-critical conditions), to produce a crude botanical drug substance, iii) precipitation with C1-C5 alcohol to reduce the proportion of non-target materials, iv) removal of the precipitate (preferably by filtration), v) optional treatment with activated charcoal, and vi) evaporation to remove C1-C5 alcohol and water, thereby producing a final botanical drug substance. Extraction techniques for cannabinoids can be found in U.S. Pat. No. 7,700,368, incorporated by reference herein.

In some embodiments, the botanical drug substance is prepared according to a process comprising the following steps: i) $CO_2$ extraction for plant terpenes, ii) ethanol extraction for crude cannabinoids, plant waxes, and plant oils (crude extract); iii) winterization of the crude extract at −80° C. for 24 hours; and iv) complete ethanol recovery and in-vessel decarboxylation of winterized crude before fractional distillation of cannabinoids.

Selection of Plant Material

Yield of particular cannabinoid or terpene from extraction varies greatly by plant tissue, type of extraction, age of material, and other variables (McPartland and Russo (2001) "*Cannabis* and *Cannabis* Extracts: Greater Than the Sum of Their Parts?" Hayworth Press). The purity of different active ingredients (e.g. cannabinoids and/or terpenes) may be enhanced in extracts by selection of appropriate starting plant material. In some embodiments, plants bred to express desired cannabinoid and/or terpene profiles (i.e., "chemovars") are selected as the starting plant material for extraction and/or purification. By way of example, if it is desired to prepare substantially pure $\Delta^9$ THC or $\Delta^9$ THCA, then "high THC" *Cannabis* plants can be selected as the starting material. Similarly, if it is desired to prepare substantially pure CBD or CBDA then "high CBD" *Cannabis* plants can be selected as the starting material. However, it is to be understood that the present disclosure is of general utility and is not limited to the use of particular *Cannabis* varieties as the starting material.

Purified *Cannabis* Compounds

In some embodiments, the botanical drug substance derived from *Cannabis* is further purified. In some embodiments, purification comprises various techniques, e.g., chromatography, crystallization, filtration, centrifuge, etc. or various combinations of said techniques. In one embodiment, "purified" means substantially free from other material, e.g., compounds, particles, vegetative material, plant derived substances, solvents, etc. In one example, the term "purified" refers to a compound purified from a crude extract, such as a biologically derived substance, thereby resulting in a significant difference between the purified compound and the extract.

Within the context of this disclosure, purified compounds may be purposely formulated with other compounds at various levels of purity. For example, depending on the desired outcome, a particular cannabinoid or terpene may be formulated with other molecules when it is 60-65% pure, 65-70% pure, 70-75% pure, 75-80% pure, 80-85% pure, 85-90% pure, 90-95% pure, 95-99% pure, 99-99.9% pure, 99.9+%, or greater than 99% pure.

In some embodiments the purity is determined by area normalization of an HPLC or GC-FID profile.

VI. Compositions

The present disclosure provides compositions comprising unique combinations of purified cannabinoids and purified terpenes. In some embodiments, the present disclosure provides compositions comprising one or more cannabinoids (e.g., a Cannabinoid Profile) and one or more terpenes (e.g., a Terpene Profile). In particular embodiments, the cannabinoids and terpenes are present in the composition at non-naturally occurring concentrations and/or ratios. In some embodiments, the compositions disclosed herein provide particular benefits previously unavailable with naturally occurring cannabinoid and/or terpene profiles, such as those found in plants, harvested flowers, extracts, or conventional products derived from the same.

In some embodiments, all components of the compositions of the present disclosure are completely derived from *Cannabis* extractions (i.e., all components are derived from the *Cannabis* plant). In some embodiments, the compositions of the present disclosure comprise one or more components are derived from sources other than the *Cannabis* plant (e.g., from other organisms, or chemically synthesized). For example, the compositions of the present disclosure can, in some embodiments, comprise cannabinoids and/or terpenes produced via standard chemical, biochemical, or biocatalytic methods. Persons having skill in the art will be familiar with various synthesis methods, including those of U.S. Pat. No. 9,359,625 and Taura et al. 1996, The Journal of Biological Chemistry, Vol. 271, No. 21, p. 17411-17416. Pharmaceutical grade "pure" cannabinoids may be purchased from commercial suppliers, for example CBD and THC can be purchased from Sigma-Aldrich Company Ltd, Fancy Road, Poole Dorset, BH12 4QH, or may be chemically synthesized.

In some embodiments, the compositions of the present invention comprise two or more active ingredients. In some embodiments, at least one active ingredient is a cannabinoid and at least one active ingredient is a terpene. In some embodiments, the compositions disclosed herein comprise a Terpene Profile and a Cannabinoid Profile. As used herein, the term "Terpene Profile" is defined as the absolute and/or relative abundance of terpenes in the compositions of the present disclosure. As used herein, the term "Cannabinoid Profile" is defined as the absolute and/or relative abundance of the cannabinoids in the compositions of the present disclosure.

In some embodiments, the compositions described herein comprise one or more terpenes and/or cannabinoids present at a non-naturally occurring concentration. As used herein, the term "non-naturally occurring concentration" refers to the amount of a compound or compounds in relation to an entire sample within a manmade composition. In one embodiment, the non-naturally occurring concentration is the amount of a cannabinoid in relation to the total composition. In one embodiment, the non-naturally occurring concentration is the amount of a terpene in relation to the total composition. In contrast, the term "naturally occurring concentration" refers to the amount of a compound or compounds in relation to an entire naturally occurring reference sample. In one embodiment, the naturally occurring concentration is the amount of a cannabinoid or terpene in a sample of a plant of genus *Cannabis*. In one embodiment, the naturally occurring concentration is the amount of a cannabinoid or terpene within the dried, or cured, flower of a plant of genus *Cannabis*. In one embodiment, the naturally occurring concentration is the amount of a cannabinoid or terpene within a crude extract of a plant of genus *Cannabis*.

In some embodiments, the compositions described herein comprise two or more terpenes present at a non-naturally occurring ratio. In some embodiments, the compositions described herein comprise two or more cannabinoids present at a non-naturally occurring ratio. As used herein, the term "non-naturally occurring ratio" refers to the proportion of one compound or compounds in relation to another compound or compounds in a composition created by a human. In one embodiment, the non-naturally occurring ratio is the amount of a first cannabinoid in relation to a second cannabinoid and is not observed in a plant of genus *Cannabis*. In one embodiment, the non-naturally occurring ratio is the amount of a first terpene in relation to a second terpene and is not observed in a plant of genus *Cannabis*. In one embodiment, the non-naturally occurring ratio is the amount of a cannabinoid in relation to a terpene and is not observed in a plant of genus *Cannabis*.

In contrast, the term "naturally occurring ratio" refers to the proportion of one compound or compounds in relation to another compound or compounds within a plant of genus *Cannabis*. In one embodiment, the naturally occurring ratio is the amount of a cannabinoid in relation to the amount of a cannabinoid within a plant of genus *Cannabis*. In one embodiment, the naturally occurring ratio is the amount of a cannabinoid in relation to the amount of a terpene within a plant of genus *Cannabis*. In one embodiment, the naturally occurring ratio is the amount of a cannabinoid in relation to the amount of a terpene within a flower of genus *Cannabis*. In one embodiment, the naturally occurring ratio is the amount of a cannabinoid in relation to the amount of a terpene within a plant extract of genus. In one embodiment, the naturally occurring ratio is the amount of a cannabinoid in relation to the amount of a terpene within a formulation made from plant extract of genus *Cannabis*.

In one embodiment, the non-naturally or naturally occurring ratio is expressed as a molar ratio. In one embodiment, the non-naturally or naturally occurring ratio is expressed as a mass. In one embodiment, the mass and/or molar ratio is measured by chromatography and/or spectroscopy.

Cannabinoid Profiles

In some embodiments, the active ingredient portion of the disclosed pharmaceutical compositions comprise one or more cannabinoids (e.g., a Cannabinoid Profile). In some embodiments, the compositions comprise 2, 3, 4, 5, 6, 7, 8, 9, 10 or more cannabinoids. In some embodiments, the compositions comprise one or more cannabinoids selected from THC, CBD, CBG, CBN, and THCV. In some embodiments, the compositions comprise THC. In some embodiments, the compositions comprise CBD. In some embodiments, the compositions comprise THC and CBD.

In some embodiments, the active ingredient portion of the disclosed pharmaceutical comprises 1%, 2%, 3%, 4%, 5%, 6%, 7% 8%, 9% 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50% THC by weight, and any ranges and subranges there between.

Thus, in some embodiments, the active ingredient portion of the disclosed pharmaceutical comprises 1%, 2%, 3%, 4%, 5%, 6%, 7% 8%, 9% 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% CBD by weight, and any ranges and subranges there between.

In some embodiments, the active ingredient portion of the disclosed pharmaceutical consists of THC and CBD. Thus in some embodiments, the active ingredient portion consists of X % THC and Y % CBD, wherein X and Y can each be 0-100%, so long as X+Y=100%.

In some embodiments, the active ingredient portion of the disclosed pharmaceutical comprises 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, or 99 mg THC, and any ranges and subranges there between.

In some embodiments, the disclosed pharmaceutical comprises 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 11 mg/mL, 12 mg/mL, 13 mg/mL, 14 mg/mL, 15 mg/mL, 16 mg/mL, 17 mg/mL, 18 mg/mL, 19 mg/mL, 20 mg/mL, 21 mg/mL, 22 mg/mL, 23 mg/mL, 24 mg/mL, 25 mg/mL, 26 mg/mL, 27 mg/mL, 28 mg/mL, 29 mg/mL, 30 mg/mL, 31 mg/mL, 32 mg/mL, 33 mg/mL, 34 mg/mL, 35 mg/mL, 36 mg/mL, 37 mg/mL, 38 mg/mL, 39 mg/mL, 40 mg/mL, 41 mg/mL, 42 mg/mL, 43 mg/mL, 44 mg/mL, 45 mg/mL, 46 mg/mL, 47 mg/mL, 48 mg/mL, 49 mg/mL, 50 mg/mL, 51 mg/mL, 52 mg/mL, 53 mg/mL, 54 mg/mL, 55 mg/mL, 56 mg/mL, 57 mg/mL, 58 mg/mL, 59 mg/mL, 60 mg/mL, 61 mg/mL, 62 mg/mL, 63 mg/mL, 64 mg/mL, 65 mg/mL, 66 mg/mL, 67 mg/mL, 68 mg/mL, 69 mg/mL, 70 mg/mL, 71 mg/mL, 72 mg/mL, 73 mg/mL, 74 mg/mL, 75 mg/mL, 76 mg/mL, 77 mg/mL, 78 mg/mL, 79 mg/mL, 80 mg/mL, 81 mg/mL, 82 mg/mL, 83 mg/mL, 84 mg/mL, 85 mg/mL, 86 mg/mL, 87 mg/mL, 88 mg/mL, 89 mg/mL, 90 mg/mL, 91 mg/mL, 92 mg/mL, 93 mg/mL, 94 mg/mL, 95 mg/mL, 96 mg/mL, 97 mg/mL, 98 mg/mL, or 99 mg/mL THC, and any ranges and subranges there between. In some embodiments, the disclosed pharmaceutical comprises 7.1 mg/mL, 7.2 mg/mL, 7.3 mg/mL, 7.4 mg/mL, 7.5 mg/mL, 7.6 mg/mL, 7.7 mg/mL, 7.8 mg/mL, 7.9 mg/mL, 8.0 mg/mL, 8.1 mg/mL, 8.2 mg/mL, 8.3 mg/mL, 8.4 mg/mL, 8.5 mg/mL, 8.6 mg/mL, 8.7 mg/mL, 8.8 mg/mL, or 8.9 mg/mL THC, and any ranges and subranges there between.

In some embodiments, the active ingredient portion of the disclosed pharmaceutical comprises 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg of CBD or more, and any ranges and subranges there between.

In some embodiments, the disclosed pharmaceutical comprises 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 11 mg/mL, 12 mg/mL, 13 mg/mL, 14 mg/mL, 15 mg/mL, 16 mg/mL, 17 mg/mL, 18 mg/mL, 19 mg/mL, 20 mg/mL, 21 mg/mL, 22 mg/mL, 23 mg/mL, 24 mg/mL, 25 mg/mL, 26 mg/mL, 27 mg/mL, 28 mg/mL, 29 mg/mL, 30 mg/mL, 31 mg/mL, 32 mg/mL, 33 mg/mL, 34 mg/mL, 35 mg/mL, 36 mg/mL, 37 mg/mL, 38 mg/mL, 39 mg/mL, 40 mg/mL, 41 mg/mL, 42 mg/mL, 43 mg/mL, 44 mg/mL, 45 mg/mL, 46 mg/mL, 47 mg/mL, 48 mg/mL, 49 mg/mL, 50 mg/mL, 51 mg/mL, 52 mg/mL, 53 mg/mL, 54 mg/mL, 55 mg/mL, 56 mg/mL, 57 mg/mL, 58 mg/mL, 59 mg/mL, 60 mg/mL, 61 mg/mL, 62 mg/mL, 63 mg/mL, 64 mg/mL, 65 mg/mL, 66 mg/mL, 67 mg/mL, 68 mg/mL, 69 mg/mL, 70 mg/mL, 71 mg/mL, 72 mg/mL, 73 mg/mL, 74 mg/mL, 75 mg/mL, 76 mg/mL, 77 mg/mL, 78 mg/mL, 79 mg/mL, 80 mg/mL, 81 mg/mL, 82 mg/mL, 83 mg/mL, 84 mg/mL, 85 mg/mL, 86 mg/mL, 87 mg/mL, 88 mg/mL, 89 mg/mL, 90 mg/mL, 91 mg/mL, 92 mg/mL, 93 mg/mL, 94 mg/mL, 95 mg/mL, 96 mg/mL, 97 mg/mL, 98 mg/mL, 99 mg/mL, 100 mg/mL, 105 mg/mL, 110 mg/mL, 115 mg/mL, 120 mg/mL, 125 mg/mL, 130 mg/mL, 135 mg/mL, 140 mg/mL, 145 mg/mL, 150 mg/mL, 155 mg/mL, 160 mg/mL, 165 mg/mL, 170 mg/mL, 175 mg/mL, 180 mg/mL, 185 mg/mL, 190 mg/mL, 195 mg/mL, 200 mg/mL, 205 mg/mL, 210 mg/mL, 215 mg/mL, 220 mg/mL, 225 mg/mL, 230 mg/mL, 235 mg/mL, 240 mg/mL, 245 mg/mL, 250 mg/mL, 255 mg/mL, 260 mg/mL, 265 mg/mL, 270 mg/mL, 275 mg/mL, 280 mg/mL, 285 mg/mL, 290 mg/mL, 295 mg/mL, 300 mg/mL, 305 mg/mL, 310 mg/mL, 315 mg/mL, 320 mg/mL, 325 mg/mL, 330 mg/mL, 335 mg/mL, 340 mg/mL, 345 mg/mL, 350 mg/mL, 355 mg/mL, 360 mg/mL, 365 mg/mL, 370 mg/mL, 375 mg/mL, 380 mg/mL, 385 mg/mL, 390 mg/mL, 395 mg/mL, 400 mg/mL, 405 mg/mL, 410 mg/mL, 415 mg/mL, 420 mg/mL, 425 mg/mL, 430 mg/mL, 435 mg/mL, 440 mg/mL, 445 mg/mL, 450 mg/mL, 455 mg/mL, 460 mg/mL, 465 mg/mL, 470 mg/mL, 475 mg/mL, 480 mg/mL, 485 mg/mL, 490 mg/mL, 495 mg/mL, 500 mg/mL, 505 mg/mL, 510 mg/mL, 515 mg/mL, 520 mg/mL, 525 mg/mL, 530 mg/mL, 535 mg/mL, 540 mg/mL, 545 mg/mL, 550 mg/mL, 555 mg/mL, 560 mg/mL, 565 mg/mL, 570 mg/mL, 575 mg/mL, 580 mg/mL, 585 mg/mL, 590 mg/mL, 595 mg/mL, 600 mg/mL, 605 mg/mL, 610 mg/mL, 615 mg/mL, 620 mg/mL, 625 mg/mL, 630 mg/mL, 635 mg/mL, 640 mg/mL, 645 mg/mL, 650 mg/mL of CBD or more, and any ranges and subranges there between. In some embodiments, the disclosed pharmaceutical comprises 1 mg/mL, 1.1 mg/mL, 1.2 mg/mL, 1.3 mg/mL, 1.4 mg/mL, 1.5 mg/mL, 1.6 mg/mL, 1.61 mg/mL, 1.62 mg/mL, 1.63 mg/mL, 1.64 mg/mL, 1.65 mg/mL, 1.66 mg/mL, 1.67 mg/mL, 1.68 mg/mL, 1.69 mg/mL 1.7 mg/mL, 1.8 mg/mL, of 1.9 mg/mL of CBD, including any ranges or subranges there between.

In some embodiments, the active ingredient portion of the disclosed pharmaceutical comprises THC and CBD present at a non-naturally occurring ratio. In some embodiments, the active ingredient portion of the disclosed pharmaceutical comprises THC and CBD present at a mass ratio of 1:1, 2:1, 3:1, 4:1, 5:1, 6:1, 7:1, 8:1, 9:1, or 10:1.

In some embodiments, the Cannabinoid Profile of the disclosed pharmaceutical comprises THC and CBD, wherein the Cannabinoid profile comprises about 40%-60% THC by weight, 40%-55% THC by weight, 40%-50% THC by weight, 40%-45% THC by weight, 45%-60% THC by weight, 50%-60% THC by weight, or about 55%-60% THC by weight. In some embodiments, the Cannabinoid Profile of the disclosed pharmaceutical comprises THC and CBD, wherein the Cannabinoid profile comprises about 45%-55% THC by weight, 50%-55% THC by weight, or about 45%-50% THC by weight. In some embodiments, the Cannabinoid Profile of the disclosed pharmaceutical comprises THC and CBD, wherein the Cannabinoid profile comprises about 45%, 46%, 47%, 48%, 49%, 50%, 51%, 52%, 53%, 54%, or 55% THC by weight.

In some embodiments, the Cannabinoid Profile of the disclosed pharmaceutical comprises THC and CBD, wherein the Cannabinoid profile comprises about 75%-95% THC by weight, 75%-90% THC by weight, 75%-85% THC by weight, 75%-80% THC by weight, 80%-95% THC by weight, 85%-95% THC by weight, or about 90%-95% THC by weight. In some embodiments, the Cannabinoid Profile of the disclosed pharmaceutical comprises THC and CBD, wherein the Cannabinoid profile comprises about 80%-90% THC by weight, 80%-85% THC by weight, or about 85%-90% THC by weight. In some embodiments, the Cannabinoid Profile of the disclosed pharmaceutical comprises THC and CBD, wherein the Cannabinoid profile comprises about 80%, 81%, 82%, 83%, 84%, 85%, 86%, 87%, 88%, 89%, or 90% THC by weight.

In some embodiments, the Cannabinoid Profile of the disclosed pharmaceutical comprises THC and CBD, wherein the Cannabinoid profile comprises about 40%-60% CBD by weight, 40%-55% CBD by weight, 40%-50% CBD by weight, 40%-45% CBD by weight, 45%-60% CBD by weight, 50%-60% CBD by weight, or about 55%-60% CBD by weight. In some embodiments, the Cannabinoid Profile of the disclosed pharmaceutical comprises THC and CBD, wherein the Cannabinoid profile comprises about 45%-55% CBD by weight, 50%-55% CBD by weight, or about 45%-50% CBD by weight. In some embodiments, the Cannabinoid Profile of the disclosed pharmaceutical comprises THC and CBD, wherein the Cannabinoid profile comprises about 45%, 46%, 47%, 48%, 49%, 50%, 51%, 52%, 53%, 54%, or 55% CBD by weight.

In some embodiments, the Cannabinoid Profile of the disclosed pharmaceutical comprises THC and CBD, wherein the Cannabinoid profile comprises about 5%-25% CBD by weight, 5%-20% CBD by weight, 5%-15% CBD by weight, 5%-10% CBD by weight, 10%-25% CBD by weight, 15%-25% CBD by weight, or about 20%-25% CBD by weight. In some embodiments, the Cannabinoid Profile of the disclosed pharmaceutical comprises THC and CBD, wherein the Cannabinoid profile comprises about 10%-20% CBD by weight, 15%-20% CBD by weight, or about 10%-15% CBD by weight. In some embodiments, the Cannabinoid Profile of the disclosed pharmaceutical comprises THC and CBD, wherein the Cannabinoid profile comprises about 10%, 11%, 12%, 13%, 14%, 15%, 16%, 17%, 18%, 19%, or 20% CBD by weight.

In some embodiments, the Cannabinoid Profile of the disclosed pharmaceutical comprises THC and CBD, wherein the Cannabinoid Profile comprises about 40%-60% THC by weight and about 40%-60% CBD by weight. In some embodiments, the Cannabinoid Profile of the disclosed pharmaceutical comprises about 45%-55% THC by weight and about 45%-55% CBD by weight. In some embodiments, the Cannabinoid Profile of the disclosed pharmaceutical comprises about 75%-95% THC by weight and about 5%-25% CBD by weight. In some embodiments, the Cannabinoid Profile of the disclosed pharmaceutical comprises about 80%-90% THC by weight and about 10%-20% CBD by weight. In some embodiments, the Cannabinoid Profile of the disclosed pharmaceutical comprises about 80%-85% THC by weight and about 15%-20% CBD by weight. In such embodiments, the percentage of each of THC and CBD can vary according to the prescribed ranges so long as the total of % THC+% CBD=100%.

Terpene Profiles

In some embodiments, the active ingredient portion of the disclosed pharmaceutical compositions comprises one or more terpenes (e.g., a Terpene Profile). In some embodiments, the active ingredient portion comprises 2, 3, 4, 5, 6, 7, 8, 9, 10 or more terpenes. In some embodiments, the active ingredient portion comprises at least one terpene selected from the group consisting of α-pinene, valencene, eucalyptol, β-caryophyllene, myrcene, α-bisabolol, and pulegone. In some embodiments, the active ingredient portion comprises at least one terpene selected from the group consisting of α-pinene, valencene, and eucalyptol. In some embodiments, the active ingredient portion comprises at least one terpene selected from the group consisting of β-caryophyllene, myrcene, α-bisabolol, and pulegone. In some embodiments, the active ingredient portion comprises at least one terpene selected from the group consisting of β-caryophyllene, myrcene, and α-bisabolol.

Generally speaking, terpenes are considered to be pharmacologically relevant when present in concentrations of at least 0.05% in plant material (Hazekamp and Fischedick (2010) Phytochemistry 2058-73; (Russo 2011) *British Journal of Pharmacology*, 163:1344-1364). Terpenes that are formulated with lower cannabinoid contents may be considered pharmacologically relevant at lower concentrations, as these formulations would likely be administered at higher doses (due to their lower cannabinoid content). Thus, although there are an estimated 120 different terpenes, only a few are produced at high enough levels to be detectable, and fewer still which are able to reach organoleptic or pharmacologically relevant levels. In some embodiments, the compositions provided herein comprise one or more "rare terpenes". Herein, a "rare terpene" refers to a terpene that is generally not present as a dominant terpene in a full spectrum terpene profile of a given *Cannabis* strain. For example, in some instances, a rare terpene is a secondary or tertiary terpene that occurs in lower concentrations in most strains.

In some embodiments, the active ingredient portion of the disclosed pharmaceutical comprises 1%, 2%, 3%, 4%, 5%, 6%, 7% 8%, 9% 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% α-pinene, valencene, eucalyptol, β-caryophyllene, myrcene, α-bisabolol, or pulegone by weight, and any ranges and subranges there between.

In some embodiments, the active ingredient portion of the disclosed pharmaceutical comprises 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, or 99 mg α-pinene, valencene, eucalyptol, β-caryophyllene, myrcene, α-bisabolol, or pulegone, and any ranges and subranges there between, and any ranges and subranges there between.

In some embodiments, the active ingredient portion of the disclosed pharmaceutical comprises 1 µg, 2 µg, 3 µg, 4 µg, 5 µg, 6 µg, 7 µg, 8 µg, 9 µg, 10 µg, 11 µg, 12 µg, 13 µg, 14 µg, 15 µg, 16 µg, 17 µg, 18 µg, 19 µg, 20 µg, 21 µg, 22 µg, 23 µg, 24 µg, 25 µg, 26 µg, 27 µg, 28 µg, 29 µg, 30 µg, 31 µg, 32 µg, 33 µg, 34 µg, 35 µg, 36 µg, 37 µg, 38 µg, 39 µg, 40 µg, 41 µg, 42 µg, 43 µg, 44 µg, 45 µg, 46 µg, 47 µg, 48 µg, 49 µg, 50 µg, 51 µg, 52 µg, 53 µg, 54 µg, 55 µg, 56 µg, 57 µg, 58 µg, 59 µg, 60 µg, 61 µg, 62 µg, 63 µg, 64 µg, 65 µg, 66 µg, 67 µg, 68 µg, 69 µg, 70 µg, 71 µg, 72 µg, 73 µg, 74 µg, 75 µg, 76 µg, 77 µg, 78 µg, 79 µg, 80 µg, 81 µg, 82 µg, 83 µg, 84 µg, 85 µg, 86 µg, 87 µg, 88 µg, 89 µg, 90 µg, 91 µg, 92 µg, 93 µg, 94 µg, 95 µg, 96 µg, 97 µg, 98 µg, or 99 µg α-pinene, valencene, eucalyptol, β-caryophyllene, myrcene, α-bisabolol, or pulegone, and any ranges and subranges there between, and any ranges and subranges there between. In some embodiments, the active ingredient portion of the disclosed pharmaceutical comprises 1.1 µg, 1.2 µg, 1.3 µg, 1.4 µg, 1.5 µg, 1.6 µg, 1.7 µg, 1.8 µg, or 1.9 µg α-pinene, valencene, eucalyptol, β-caryophyllene, myrcene, α-bisabolol, or pulegone, and any ranges and subranges there between, and any ranges and subranges there between.

In some embodiments, the active ingredient portion of the disclosed pharmaceutical comprises 1 ng, 2 ng, 3 ng, 4 ng, 5 ng, 6 ng, 7 ng, 8 ng, 9 ng, 10 ng, 11 ng, 12 ng, 13 ng, 14 ng, 15 ng, 16 ng, 17 ng, 18 ng, 19 ng, 20 ng, 21 ng, 22 ng, 23 ng, 24 ng, 25 ng, 26 ng, 27 ng, 28 ng, 29 ng, 30 ng, 31 ng, 32 ng, 33 ng, 34 ng, 35 ng, 36 ng, 37 ng, 38 ng, 39 ng, 40 ng, 41 ng, 42 ng, 43 ng, 44 ng, 45 ng, 46 ng, 47 ng, 48 ng, 49 ng, 50 ng, 51 ng, 52 ng, 53 ng, 54 ng, 55 ng, 56 ng, 57 ng, 58 ng, 59 ng, 60 ng, 61 ng, 62 ng, 63 ng, 64 ng, 65 ng, 66 ng, 67 ng, 68 ng, 69 ng, 70 ng, 71 ng, 72 ng, 73 ng, 74 ng, 75 ng, 76 ng, 77 ng, 78 ng, 79 ng, 80 ng, 81 ng, 82 ng, 83 ng, 84 ng, 85 ng, 86 ng, 87 ng, 88 ng, 89 ng, 90 ng, 91 ng, 92 ng, 93 ng, 94 ng, 95 ng, 96 ng, 97 ng, 98 ng, or 99 ng, 100 ng, 150 ng, 200 ng, 250 ng, 300 ng, 350 ng, 400 ng, 450 ng, 500 ng, 550 ng, 600 ng, 650 ng, 600 ng, 750 ng, 800 ng, 850 ng, 900 ng, or 950 ng α-pinene, valencene, eucalyptol, β-caryophyllene, myrcene, α-bisabolol, or pulegone, and any ranges and subranges there between, and any ranges and subranges there between.

In some embodiments, the disclosed pharmaceutical comprises 0.01 mg/mL, 0.02 mg/mL, 0.03 mg/mL, 0.04 mg/mL, 0.05 mg/mL, 0.06 mg/mL, 0.07 mg/mL, 0.08 mg/mL, 0.09 mg/mL, 0.1 mg/mL, 0.11 mg/mL, 0.12 mg/mL, 0.13 mg/mL, 0.14 mg/mL, 0.15 mg/mL, 0.16 mg/mL, 0.17 mg/mL, 0.18 mg/mL, 0.19 mg/mL, 0.2 mg/mL, 0.21 mg/mL, 0.22 mg/mL, 0.23 mg/mL, 0.24 mg/mL, 0.25 mg/mL, 0.26 mg/mL, 0.27 mg/mL, 0.28 mg/mL, 0.29 mg/mL, 0.3 mg/mL, 0.31 mg/mL, 0.32 mg/mL, 0.33 mg/mL, 0.34 mg/mL, 0.35 mg/mL, 0.36 mg/mL, 0.37 mg/mL, 0.38 mg/mL, 0.39 mg/mL, 0.4 mg/mL, 0.41 mg/mL, 0.42 mg/mL, 0.43 mg/mL, 0.44 mg/mL, 0.45 mg/mL, 0.46 mg/mL, 0.47 mg/mL, 0.48 mg/mL, 0.49 mg/mL, 0.5 mg/mL, 0.51 mg/mL, 0.52 mg/mL, 0.53 mg/mL, 0.54 mg/mL, 0.55 mg/mL, 0.56 mg/mL, 0.57 mg/mL, 0.58 mg/mL, 0.59 mg/mL, 0.6 mg/mL, 0.61 mg/mL, 0.62 mg/mL, 0.63 mg/mL, 0.64 mg/mL, 0.65 mg/mL, 0.66 mg/mL, 0.67 mg/mL, 0.68 mg/mL, 0.69 mg/mL, 0.7 mg/mL, 0.71 mg/mL, 0.72 mg/mL, 0.73 mg/mL, 0.74 mg/mL, 0.75 mg/mL, 0.76 mg/mL, 0.77 mg/mL, 0.78 mg/mL, 0.79 mg/mL, 0.8 mg/mL, 0.81 mg/mL, 0.82 mg/mL, 0.83 mg/mL, 0.84 mg/mL, 0.85 mg/mL, 0.86 mg/mL, 0.87 mg/mL, 0.88 mg/mL, 0.89 mg/mL, 0.9 mg/mL, 0.91 mg/mL, 0.92 mg/mL, 0.93 mg/mL, 0.94 mg/mL, 0.95 mg/mL, 0.96 mg/mL, 0.97 mg/mL, 0.98 mg/mL, 0.99 mg/mL, 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 11 mg/mL, 12 mg/mL, 13 mg/mL, 14 mg/mL, 15 mg/mL, 16 mg/mL, 17 mg/mL, 18 mg/mL, 19 mg/mL, 20 mg/mL, 21 mg/mL, 22 mg/mL, 23 mg/mL, 24 mg/mL, 25 mg/mL, 26 mg/mL, 27 mg/mL, 28 mg/mL, 29 mg/mL, 30 mg/mL, 31 mg/mL, 32 mg/mL, 33 mg/mL, 34 mg/mL, 35 mg/mL, 36 mg/mL, 37 mg/mL, 38 mg/mL, 39 mg/mL, 40 mg/mL, 41 mg/mL, 42 mg/mL, 43 mg/mL, 44 mg/mL, 45 mg/mL, 46 mg/mL, 47 mg/mL, 48 mg/mL, 49 mg/mL, 50 mg/mL, 51 mg/mL, 52 mg/mL, 53 mg/mL, 54 mg/mL, 55 mg/mL, 56 mg/mL, 57 mg/mL, 58 mg/mL, 59 mg/mL, 60 mg/mL, 61 mg/mL, 62 mg/mL, 63 mg/mL, 64 mg/mL, 65 mg/mL, 66 mg/mL, 67 mg/mL, 68 mg/mL, 69 mg/mL, 70 mg/mL, 71 mg/mL, 72 mg/mL, 73 mg/mL, 74 mg/mL, 75 mg/mL, 76 mg/mL, 77 mg/mL, 78 mg/mL, 79 mg/mL, 80 mg/mL, 81 mg/mL, 82 mg/mL, 83 mg/mL, 84 mg/mL, 85 mg/mL, 86 mg/mL, 87 mg/mL, 88 mg/mL, 89 mg/mL, 90 mg/mL, 91 mg/mL, 92 mg/mL, 93 mg/mL, 94 mg/mL, 95 mg/mL, 96 mg/mL, 97 mg/mL, 98 mg/mL, or 99 mg/mL α-pinene, valencene, eucalyptol, β-caryophyllene, myrcene, α-bisabolol, or pulegone, and any ranges and subranges there between, and any ranges and subranges there between.

In some embodiments, the disclosed pharmaceutical comprises 0.01 µg/mL, 0.02 µg/mL, 0.03 µg/mL, 0.04 µg/mL, 0.05 µg/mL, 0.06 µg/mL, 0.07 µg/mL, 0.08 µg/mL, 0.09 µg/mL, 0.1 µg/mL, 0.11 µg/mL, 0.12 µg/mL, 0.13 µg/mL, 0.14 µg/mL, 0.15 µg/mL, 0.16 µg/mL, 0.17 µg/mL, 0.18

µg/mL, 0.19 µg/mL, 0.2 µg/mL, 0.21 µg/mL, 0.22 µg/mL, 0.23 µg/mL, 0.24 µg/mL, 0.25 µg/mL, 0.26 µg/mL, 0.27 µg/mL, 0.28 µg/mL, 0.29 µg/mL, 0.3 µg/mL, 0.31 µg/mL, 0.32 µg/mL, 0.33 µg/mL, 0.34 µg/mL, 0.35 µg/mL, 0.36 µg/mL, 0.37 µg/mL, 0.38 µg/mL, 0.39 µg/mL, 0.4 µg/mL, 0.41 µg/mL, 0.42 µg/mL, 0.43 µg/mL, 0.44 µg/mL, 0.45 µg/mL, 0.46 µg/mL, 0.47 µg/mL, 0.48 µg/mL, 0.49 µg/mL, 0.5 µg/mL, 0.51 µg/mL, 0.52 µg/mL, 0.53 µg/mL, 0.54 µg/mL, 0.55 µg/mL, 0.56 µg/mL, 0.57 µg/mL, 0.58 µg/mL, 0.59 µg/mL, 0.6 µg/mL, 0.61 µg/mL, 0.62 µg/mL, 0.63 µg/mL, 0.64 µg/mL, 0.65 µg/mL, 0.66 µg/mL, 0.67 µg/mL, 0.68 µg/mL, 0.69 µg/mL, 0.7 µg/mL, 0.71 µg/mL, 0.72 µg/mL, 0.73 µg/mL, 0.74 µg/mL, 0.75 µg/mL, 0.76 µg/mL, 0.77 µg/mL, 0.78 µg/mL, 0.79 µg/mL, 0.8 µg/mL, 0.81 µg/mL, 0.82 µg/mL, 0.83 µg/mL, 0.84 µg/mL, 0.85 µg/mL, 0.86 µg/mL, 0.87 µg/mL, 0.88 µg/mL, 0.89 µg/mL, 0.9 µg/mL, 0.91 µg/mL, 0.92 µg/mL, 0.93 µg/mL, 0.94 µg/mL, 0.95 µg/mL, 0.96 µg/mL, 0.97 µg/mL, 0.98 µg/mL, 0.99 µg/mL, 1 µg/mL, 2 µg/mL, 3 µg/mL, 4 µg/mL, 5 µg/mL, 6 µg/mL, 7 µg/mL, 8 µg/mL, 9 µg/mL, 10 µg/mL, 11 µg/mL, 12 µg/mL, 13 µg/mL, 14 µg/mL, 15 µg/mL, 16 µg/mL, 17 µg/mL, 18 µg/mL, 19 µg/mL, 20 µg/mL, 21 µg/mL, 22 µg/mL, 23 µg/mL, 24 µg/mL, 25 µg/mL, 26 µg/mL, 27 µg/mL, 28 µg/mL, 29 µg/mL, 30 µg/mL, 31 µg/mL, 32 µg/mL, 33 µg/mL, 34 µg/mL, 35 µg/mL, 36 µg/mL, 37 µg/mL, 38 µg/mL, 39 µg/mL, 40 µg/mL, 41 µg/mL, 42 µg/mL, 43 µg/mL, 44 µg/mL, 45 µg/mL, 46 µg/mL, 47 µg/mL, 48 µg/mL, 49 µg/mL, 50 µg/mL, 51 µg/mL, 52 µg/mL, 53 µg/mL, 54 µg/mL, 55 µg/mL, 56 µg/mL, 57 µg/mL, 58 µg/mL, 59 µg/mL, 60 µg/mL, 61 µg/mL, 62 µg/mL, 63 µg/mL, 64 µg/mL, 65 µg/mL, 66 µg/mL, 67 µg/mL, 68 µg/mL, 69 µg/mL, 70 µg/mL, 71 µg/mL, 72 µg/mL, 73 µg/mL, 74 µg/mL, 75 µg/mL, 76 µg/mL, 77 µg/mL, 78 µg/mL, 79 µg/mL, 80 µg/mL, 81 µg/mL, 82 µg/mL, 83 µg/mL, 84 µg/mL, 85 µg/mL, 86 µg/mL, 87 µg/mL, 88 µg/mL, 89 µg/mL, 90 µg/mL, 91 µg/mL, 92 µg/mL, 93 µg/mL, 94 µg/mL, 95 µg/mL, 96 µg/mL, 97 µg/mL, 98 µg/mL, or 99 µg/mL α-pinene, valencene, eucalyptol, β-caryophyllene, myrcene, α-bisabolol, or pulegone, and any ranges and subranges there between, and any ranges and subranges there between.

In some embodiments, the disclosed pharmaceutical comprises 100 ng/mL, 150 ng/mL, 200 ng/mL, 250 ng/mL, 300 ng/mL, 350 ng/mL, 400 ng/mL, 401 ng/mL, 402 ng/mL, 403 ng/mL, 404 ng/mL, 405 ng/mL, 406 ng/mL, 407 ng/mL, 408 ng/mL, 409 ng/mL, 410 ng/mL, 411 ng/mL, 412 ng/mL, 413 ng/mL, 414 ng/mL, 415 ng/mL, 416 ng/mL, 417 ng/mL, 418 ng/mL, 419 ng/mL, 420 ng/mL, 421 ng/mL, 422 ng/mL, 423 ng/mL, 424 ng/mL, 425 ng/mL, 426 ng/mL, 427 ng/mL, 428 ng/mL, 429 ng/mL, 450 ng/mL, 500 ng/mL, 525 ng/mL, 526 ng/mL, 527 ng/mL, 528 ng/mL, 529 ng/mL, 530 ng/mL, 531 ng/mL, 532 ng/mL, 533 ng/mL, 534 ng/mL, 535 ng/mL, 536 ng/mL, 537 ng/mL, 538 ng/mL, 539 ng/mL, 540 ng/mL, 541 ng/mL, 542 ng/mL, 543 ng/mL, 544 ng/mL, 545 ng/mL, 546 ng/mL, 547 ng/mL, 548 ng/mL, 549 ng/mL, 550 ng/mL, 551 ng/mL, 552 ng/mL, 553 ng/mL, 554 ng/mL, 555 ng/mL, 556 ng/mL, 557 ng/mL, 558 ng/mL, 559 ng/mL, 560 ng/mL, 600 ng/mL, 650 ng/mL, 700 ng/mL, 750 ng/mL, 800 ng/mL, 850 ng/mL, 900 ng/mL, or 950 ng/mL α-pinene, valencene, eucalyptol, β-caryophyllene, myrcene, α-bisabolol, or pulegone, and any ranges and subranges there between, and any ranges and subranges there between.

In some embodiments, the Terpene Profile of the disclosed pharmaceutical comprises 3 terpenes selected from the group consisting of α-pinene, valencene, eucalyptol, β-caryophyllene, myrcene, α-bisabolol, and pulegone. In some embodiments, the Terpene Profile of the disclosed pharmaceutical comprises α-pinene, valencene, and eucalyptol. In some embodiments, the Terpene Profile comprises, in order of relative abundance (from low to high):

(a) α-pinene, valencene, and eucalyptol;
(b) α-pinene, eucalyptol, and valencene;
(c) valencene, α-pinene, and eucalyptol;
(d) valencene, eucalyptol, and α-pinene;
(e) eucalyptol, α-pinene, and valencene; or
(f) eucalyptol, valencene, and α-pinene.

In some embodiments, the Terpene Profile of the disclosed pharmaceutical comprises α-pinene, valencene, and eucalyptol at a non-naturally occurring ratio. In some embodiments, the Terpene Profile of the disclosed pharmaceutical comprises α-pinene, valencene, and eucalyptol, wherein α-pinene and valencene are present at a mass ratio of 5:1 to 1:5, 4:1 to 1:4, 3:1 to 1:3, 2:1 to 1:2, or 1:1. In some embodiments, the Terpene Profile comprises α-pinene, valencene, and eucalyptol, wherein α-pinene and eucalyptol are present at a mass ratio of 5:1 to 1:5, 4:1 to 1:4, 3:1 to 1:3, 2:1 to 1:2, or 1:1. In some embodiments, the Terpene Profile of the disclosed pharmaceutical comprises α-pinene, valencene, and eucalyptol, wherein valencene and eucalyptol are present at a mass ratio of 5:1 to 1:5, 4:1 to 1:4, 3:1 to 1:3, 2:1 to 1:2, or 1:1.

In some embodiments, the Terpene Profile of the disclosed pharmaceutical comprises α-pinene, valencene, and eucalyptol, wherein the Terpene Profile comprises about 15%-35% α-pinene by weight, about 20%-35% α-pinene by weight, about 25%-35% α-pinene by weight, about 30%-35% α-pinene by weight, about 15%-30% α-pinene by weight, about 15%-25% α-pinene by weight, or about 15%-20% α-pinene by weight. In some embodiments, the Terpene Profile of the disclosed pharmaceutical comprises α-pinene, valencene, and eucalyptol, wherein the Terpene Profile comprises about 20%-30% α-pinene by weight, about 20%-25% α-pinene by weight, or about 25%-30% α-pinene by weight. In some embodiments, the Terpene Profile of the disclosed pharmaceutical comprises α-pinene, valencene, and eucalyptol, wherein the Terpene Profile comprises about 20%, 21%, 22%, 23%, 24%, 25%, 26%, 27%, 28%, 29% or about 30% α-pinene by weight.

In some embodiments, the Terpene Profile of the disclosed pharmaceutical comprises α-pinene, valencene, and eucalyptol, wherein the Terpene Profile comprises about 20%-40% α-pinene by weight, about 25%-40% α-pinene by weight, about 30%-40% α-pinene by weight, about 35%-40% α-pinene by weight, about 20%-35% α-pinene by weight, about 20%-30% α-pinene by weight, or about 20%-25% α-pinene by weight. In some embodiments, the Terpene Profile of the disclosed pharmaceutical comprises α-pinene, valencene, and eucalyptol, wherein the Terpene Profile comprises about 25%-35% α-pinene by weight, about 25%-30% α-pinene by weight, or about 20%-25% α-pinene by weight. In some embodiments, the Terpene Profile of the disclosed pharmaceutical comprises α-pinene, valencene, and eucalyptol, wherein the Terpene Profile comprises about 25%, 26%, 27%, 28%, 29%, 30%, 31%, 32%, 33%, 34%, or about 35% α-pinene by weight.

In some embodiments, the Terpene Profile of the disclosed pharmaceutical comprises α-pinene, valencene, and eucalyptol, wherein the Terpene Profile comprises about 15%-35% valencene by weight, about 20%-35% valencene by weight, about 25%-35% valencene by weight, about 30%-35% valencene by weight, about 15%-30% valencene by weight, about 15% 20%-25% valencene by weight, or about 15%-20% valencene by weight. In some embodiments, the Terpene Profile of the disclosed pharmaceutical comprises α-pinene, valencene, and eucalyptol, wherein the Terpene Profile comprises about 20%-30% valencene by weight, about 20%-25% valencene by weight, or about 25%-30% valencene by weight. In some embodiments, the Terpene Profile of the disclosed pharmaceutical comprises α-pinene, valencene, and eucalyptol, wherein the Terpene Profile comprises about 20%, 21%, 22%, 23%, 24%, 25%, 26%, 27%, 28%, 29% or about 30% valencene by weight.

In some embodiments, the Terpene Profile of the disclosed pharmaceutical comprises α-pinene, valencene, and eucalyptol, wherein the Terpene Profile comprises about 20%-40% valencene by weight, about 20%-35% valencene by weight, about 20%-30% valencene, about 20%-25% valencene by weight, about 20%-35% valencene by weight, about 20%-30% valencene, or about 20%-25% valencene by weight. In some embodiments, the Terpene Profile of the disclosed pharmaceutical comprises α-pinene, valencene, and eucalyptol, wherein the Terpene Profile comprises about 25%-35% valencene by weight, about 25%-30% valencene by weight, or about 30%-35% valencene by weight. In some embodiments, the Terpene Profile of the disclosed pharmaceutical comprises α-pinene, valencene, and eucalyptol, wherein the Terpene Profile comprises about 25%, 26%, 27%, 28%, 29%, 30%, 31%, 32%, 33%, 34%, or about 35% valencene by weight.

In some embodiments, the Terpene Profile of the disclosed pharmaceutical comprises α-pinene, valencene, and eucalyptol, wherein the Terpene Profile comprises about 40%-60% eucalyptol by weight, 45%-60% eucalyptol by weight, 50%-60% eucalyptol by weight, 55%-60% eucalyptol by weight, 40%-55% eucalyptol by weight, 40%-50% eucalyptol by weight, or about 40%-55% eucalyptol by weight. In some embodiments, the Terpene Profile of the disclosed pharmaceutical comprises α-pinene, valencene, and eucalyptol, wherein the Terpene Profile comprises about 45%-55% eucalyptol by weight, about 50%-55% eucalyptol by weight, or about 45%-50% eucalyptol by weight. In some embodiments, the Terpene Profile of the disclosed pharmaceutical comprises α-pinene, valencene, and eucalyptol, wherein the Terpene Profile comprises about 45%, 46%, 47%, 48%, 49%, 50%, 51%, 52%, 53%, 54%, or about 55% eucalyptol by weight.

In some embodiments, the Terpene Profile of the disclosed pharmaceutical comprises α-pinene, valencene, and eucalyptol, wherein the Terpene Profile comprises about 30%-50% eucalyptol by weight, 30%-45% eucalyptol by weight, 30%-40% eucalyptol by weight, 30%-35% eucalyptol by weight, 35%-50% eucalyptol by weight, 40%-50% eucalyptol by weight, or about 45%-40% eucalyptol by weight. In some embodiments, the Terpene Profile of the disclosed pharmaceutical comprises α-pinene, valencene, and eucalyptol, wherein the Terpene Profile comprises about 35%-45% eucalyptol by weight, about 40%-45% eucalyptol by weight, or about 35%-40% eucalyptol by weight. In some embodiments, the Terpene Profile of the disclosed pharmaceutical comprises α-pinene, valencene, and eucalyptol, wherein the Terpene Profile comprises about 35%, 36%, 37%, 38%, 39%, 40%, 41%, 42%, 43%, 44%, or 45% eucalyptol by weight.

In some embodiments, the Terpene Profile of the disclosed pharmaceutical comprises α-pinene, valencene, and eucalyptol, wherein the Terpene Profile comprises about 20%-40% α-pinene by weight, about 20%-35% α-pinene by weight, about 20%-30% α-pinene by weight, about 20%-25% α-pinene by weight, about 25%-40% α-pinene by weight, about 30%-40% α-pinene by weight, or about 35%-40% α-pinene by weight. In some embodiments, the Terpene Profile of the disclosed pharmaceutical comprises α-pinene, valencene, and eucalyptol, wherein the Terpene Profile comprises about 25%-35% α-pinene by weight, about 25%-30% α-pinene by weight, or about 30%-35% α-pinene by weight. In some embodiments, the Terpene Profile of the disclosed pharmaceutical comprises α-pinene, valencene, and eucalyptol, wherein the Terpene Profile comprises about 20%, 21%, 22%, 23%, 24%, 25%, 26%, 27%, 28%, 29%, 30%, 31%, 32%, 33%, 34%, 35%, 36%, 37%, 38%, 39%, or 40% α-pinene by weight.

In some embodiments, the Terpene Profile of the disclosed pharmaceutical comprises α-pinene, valencene, and eucalyptol, wherein the Terpene Profile comprises about 20%-40% valencene by weight, about 20%-35% valencene by weight, about 20%-30% valencene by weight, about 20%-25% valencene by weight, about 25%-40% valencene by weight, about 30%-40% valencene by weight, or about 35%-40% valencene by weight. In some embodiments, the Terpene Profile of the disclosed pharmaceutical comprises α-pinene, valencene, and eucalyptol, wherein the Terpene Profile comprises about 25%-35% valencene by weight, about 25%-30% valencene by weight, or about 30%-35% valencene by weight. In some embodiments, the Terpene Profile of the disclosed pharmaceutical comprises α-pinene, valencene, and eucalyptol, wherein the Terpene Profile comprises about 20%, 21%, 22%, 23%, 24%, 25%, 26%, 27%, 28%, 29%, 30%, 31%, 32%, 33%, 34%, 35%, 36%, 37%, 38%, 39%, or 40% valencene by weight.

In some embodiments, the Terpene Profile of the disclosed pharmaceutical comprises α-pinene, valencene, and eucalyptol, wherein the Terpene Profile comprises about 20%-40% eucalyptol by weight, about 20%-35% eucalyptol by weight, about 20%-30% eucalyptol by weight, about 20%-25% eucalyptol by weight, about 25%-40% eucalyptol by weight, about 30%-40% eucalyptol by weight, or about 35%-40% eucalyptol by weight. In some embodiments, the Terpene Profile of the disclosed pharmaceutical comprises α-pinene, valencene, and eucalyptol, wherein the Terpene Profile comprises about 25%-35% eucalyptol by weight, about 25%-30% eucalyptol by weight, or about 30%-35% eucalyptol by weight. In some embodiments, the Terpene Profile of the disclosed pharmaceutical comprises α-pinene, valencene, and eucalyptol, wherein the Terpene Profile comprises about 20%, 21%, 22%, 23%, 24%, 25%, 26%, 27%, 28%, 29%, 30%, 31%, 32%, 33%, 34%, 35%, 36%, 37%, 38%, 39%, or 40% eucalyptol by weight.

In some embodiments, the Terpene Profile of the disclosed pharmaceutical comprises α-pinene, valencene, and eucalyptol, wherein the Terpene Profile comprises 15%-35% α-pinene by weight, 15%-35% valencene by weight, and 40%-60% eucalyptol by weight. In some embodiments, the Terpene Profile of the disclosed pharmaceutical comprises α-pinene, valencene, and eucalyptol, wherein the Terpene Profile comprises 20%-25% α-pinene by weight, 20%-25% valencene by weight, and 45%-55% eucalyptol by weight. In some embodiments, the Terpene Profile of the disclosed pharmaceutical comprises α-pinene, valencene, and eucalyptol, wherein the Terpene Profile comprises 20%-40% α-pinene by weight, 20%-40% valencene by weight, and 20%-40% eucalyptol by weight. In some embodiments, the Terpene Profile of the disclosed pharmaceutical comprises α-pinene, valencene, and eucalyptol, wherein the Terpene Profile comprises 25%-35% α-pinene by weight, 25%-35% valencene by weight, and 25%-35% eucalyptol by weight. In such embodiments, the percentage of each of α-pinene, valencene, and eucalyptol can vary according to the prescribed ranges so long as the total of % α-pinene+% valencene+% eucalyptol=100%.

In some embodiments, the Terpene Profile of the disclosed pharmaceutical comprises 4 terpenes selected from the group consisting of α-pinene, valencene, eucalyptol, β-caryophyllene, myrcene, α-bisabolol, and pulegone. In some embodiments, the Terpene Profile of the disclosed pharmaceutical comprises β-caryophyllene, myrcene, α-bisabolol, and pulegone. In some embodiments, the Terpene Profile comprises in order of relative abundance (from low to high):

(a) β-caryophyllene, myrcene, α-bisabolol, and pulegone;
(b) β-caryophyllene, myrcene, pulegone, and α-bisabolol;
(c) β-caryophyllene, pulegone, myrcene, and α-bisabolol;
(d) β-caryophyllene, pulegone, α-bisabolol, and myrcene;
(e) β-caryophyllene, α-bisabolol, pulegone, and myrcene;
(f) β-caryophyllene, α-bisabolol, myrcene, and pulegone;
(g) α-bisabolol, β-caryophyllene, myrcene, and pulegone;
(h) α-bisabolol, β-caryophyllene, pulegone, and myrcene;
(i) α-bisabolol, myrcene, β-caryophyllene, and pulegone;
(j) α-bisabolol, myrcene, pulegone, and β-caryophyllene;
(k) α-bisabolol, pulegone, myrcene, and β-caryophyllene;
(l) α-bisabolol, pulegone, β-caryophyllene, and myrcene;
(m) myrcene, α-bisabolol, β-caryophyllene, and pulegone;
(n) myrcene, α-bisabolol, pulegone, and β-caryophyllene;
(o) myrcene, β-caryophyllene, α-bisabolol, and pulegone;
(p) myrcene, β-caryophyllene, pulegone, and α-bisabolol;
(q) myrcene, pulegone, β-caryophyllene, and α-bisabolol;
(r) myrcene, pulegone, α-bisabolol, and β-caryophyllene;
(s) pulegone, myrcene, α-bisabolol, and β-caryophyllene;
(t) pulegone, myrcene, β-caryophyllene, and α-bisabolol;
(u) pulegone, α-bisabolol, myrcene, and β-caryophyllene;
(v) pulegone, α-bisabolol, β-caryophyllene, and myrcene;
(w) pulegone, β-caryophyllene, α-bisabolol, and myrcene; or
(x) pulegone, β-caryophyllene, myrcene, and α-bisabolol.

In some embodiments, the Terpene Profile of the disclosed pharmaceutical comprises β-caryophyllene, myrcene, α-bisabolol, and pulegone at a non-naturally occurring ratio. In some embodiments, the Terpene Profile of the disclosed pharmaceutical comprises β-caryophyllene, myrcene, α-bisabolol, and pulegone, wherein β-caryophyllene and myrcene are present at a mass ratio of 5:1 to 1:5, 4:1 to 1:4, 3:1 to 1:3, 2:1 to 1:2, or 1:1. In some embodiments, the Terpene Profile comprises β-caryophyllene, myrcene, α-bisabolol, and pulegone, wherein β-caryophyllene and α-bisabolol are present at a mass ratio of 5:1 to 1:5, 4:1 to 1:4, 3:1 to 1:3, 2:1 to 1:2, or 1:1. In some embodiments, the Terpene Profile comprises β-caryophyllene, myrcene, α-bisabolol, and pulegone, wherein β-caryophyllene and pulegone are present at a mass ratio of 5:1 to 1:5, 4:1 to 1:4, 3:1 to 1:3, 2:1 to 1:2, or 1:1. In some embodiments, the Terpene Profile comprises β-caryophyllene, myrcene, α-bisabolol, and pulegone, wherein myrcene and α-bisabolol are present at a mass ratio of 5:1 to 1:5, 4:1 to 1:4, 3:1 to 1:3, 2:1 to 1:2, or 1:1. In some embodiments, the Terpene Profile comprises β-caryophyllene, myrcene, α-bisabolol, and pulegone, wherein myrcene and pulegone are present at a mass ratio of 5:1 to 1:5, 4:1 to 1:4, 3:1 to 1:3, 2:1 to 1:2, or 1:1. In some embodiments, the Terpene Profile comprises β-caryophyllene, myrcene, α-bisabolol, and pulegone, wherein α-bisabolol and pulegone are present at a mass ratio of 5:1 to 1:5, 4:1 to 1:4, 3:1 to 1:3, 2:1 to 1:2, or 1:1.

In some embodiments, the Terpene Profile of the disclosed pharmaceutical comprises β-caryophyllene, myrcene, α-bisabolol, and pulegone, wherein the Terpene profile comprises about 35%-55% β-caryophyllene by weight, about 35%-50% β-caryophyllene by weight, about 35%-45% β-caryophyllene by weight, about 35%-40% β-caryophyllene by weight, about 40%-55% β-caryophyllene by weight, about 45%-55% β-caryophyllene by weight, or about 50%-55% β-caryophyllene by weight. In some embodiments, the Terpene Profile of the disclosed pharmaceutical comprises β-caryophyllene, myrcene, α-bisabolol, and pulegone, wherein the Terpene profile comprises about 40%-50% β-caryophyllene by weight, about 45%-50% β-caryophyllene by weight, or about 40%-45% β-caryophyllene by weight. In some embodiments, the Terpene Profile of the disclosed pharmaceutical comprises β-caryophyllene, myrcene, α-bisabolol, and pulegone, wherein the Terpene profile comprises about 40%, 41%, 42%, 43%, 44%, 45%, 46%, 47%, 48%, 49%, or 50% by weight β-caryophyllene.

In some embodiments, the Terpene Profile of the disclosed pharmaceutical comprises β-caryophyllene, myrcene, α-bisabolol, and pulegone, wherein the Terpene profile comprises about 10%-30% myrcene by weight, about 10%-25% myrcene by weight, about 10%-20% myrcene by weight, about 10%-15% myrcene by weight, about 15%-30% myrcene by weight, about 20%-30% myrcene by weight, or about 25%-30% myrcene by weight. In some embodiments, the Terpene Profile of the disclosed pharmaceutical comprises β-caryophyllene, myrcene, α-bisabolol, and pulegone, wherein the Terpene profile comprises about 15%-25% myrcene by weight, about 20%-25% myrcene by weight, or about 15%-20% myrcene by weight. In some embodiments, the Terpene Profile of the disclosed pharmaceutical comprises β-caryophyllene, myrcene, α-bisabolol, and pulegone, wherein the Terpene profile comprises about 15%, 16%, 17%, 18%, 19%, 20%, 21%, 22%, 23%, 24% or about 25% myrcene by weight.

In some embodiments, the Terpene Profile of the disclosed pharmaceutical comprises β-caryophyllene, myrcene, α-bisabolol, and pulegone, wherein the Terpene profile comprises about 10%-30% α-bisabolol by weight, about 10%-25% α-bisabolol by weight, about 10%-20% α-bisabolol by weight, about 10%-15% α-bisabolol by weight, about 15%-30% α-bisabolol by weight, about 20%-30% α-bisabolol by weight, or about 25%-30% α-bisabolol by weight. In some embodiments, the Terpene Profile of the disclosed pharmaceutical comprises β-caryophyllene, myrcene, α-bisabolol, and pulegone, wherein the Terpene profile comprises about 15%-25% α-bisabolol by weight, about 20%-25% α-bisabolol by weight, or about 15%-20% α-bisabolol by weight. In some embodiments, the Terpene Profile of the disclosed pharmaceutical comprises β-caryophyllene, myrcene, α-bisabolol, and pulegone, wherein the Terpene profile comprises about 15%, 16%, 17%, 18%, 19%, 20%, 21%, 22%, 23%, 24% or about 25% α-bisabolol by weight.

In some embodiments, the Terpene Profile of the disclosed pharmaceutical comprises β-caryophyllene, myrcene, α-bisabolol, and pulegone, wherein the Terpene profile comprises about 5%-25% pulegone by weight, about 5%-20% pulegone by weight, about 5%-15% pulegone by weight, about 5%-10% pulegone by weight, about 10%-25% pulegone by weight, about 15%-25% pulegone by weight, or about 20%-25% pulegone by weight. In some embodiments, the Terpene Profile of the disclosed pharmaceutical comprises β-caryophyllene, myrcene, α-bisabolol, and pulegone, wherein the Terpene profile comprises about 10%-20% pulegone by weight, about 10%-15% pulegone by weight, or about 15%-20% pulegone by weight. In some embodiments, the Terpene Profile of the disclosed pharmaceutical comprises β-caryophyllene, myrcene, α-bisabolol, and pulegone, wherein the Terpene profile comprises about 10%, 11%, 12%, 13%, 14%, 15%, 16%, 17%, 18%, 19% or about 20% pulegone by weight.

In some embodiments, the Terpene Profile of the disclosed pharmaceutical comprises (3-caryophyllene, myrcene, α-bisabolol, and pulegone, wherein the Terpene profile comprises about 15%-35% β-caryophyllene by weight, about 15%-30% β-caryophyllene by weight, about 15%-25% β-caryophyllene by weight, about 15%-20% β-caryophyllene by weight, about 20%-35% β-caryophyllene by weight, about 25%-35% β-caryophyllene by weight, or about 30%-35% β-caryophyllene by weight. In some embodiments, the Terpene Profile of the disclosed pharmaceutical comprises β-caryophyllene, myrcene, α-bisabolol, and pulegone, wherein the Terpene profile comprises about 20%-30% β-caryophyllene by weight, about 25%-30% β-caryophyllene by weight, or about 20%-25% β-caryophyllene by weight. In some embodiments, the Terpene Profile of the disclosed pharmaceutical comprises β-caryophyllene, myrcene, α-bisabolol, and pulegone, wherein the Terpene profile comprises about 20%, 21%, 22%, 23%, 24%, 25%, 26%, 27%, 28%, 29%, or about 30% β-caryophyllene by weight.

In some embodiments, the Terpene Profile of the disclosed pharmaceutical comprises (3-caryophyllene, myrcene, α-bisabolol, and pulegone, wherein the Terpene profile comprises about 15%-35% myrcene by weight, about 15%-30% myrcene by weight, about 15%-25% myrcene by weight, about 15%-20% myrcene by weight, about 20%-35% myrcene by weight, about 25%-35% myrcene by weight, or about 30%-35% myrcene by weight. In some embodiments, the Terpene Profile of the disclosed pharmaceutical comprises β-caryophyllene, myrcene, α-bisabolol, and pulegone, wherein the Terpene profile comprises about 20%-30% myrcene by weight, about 25%-30% myrcene by weight, or about 20%-25% myrcene by weight. In some embodiments, the Terpene Profile of the disclosed pharmaceutical comprises β-caryophyllene, myrcene, α-bisabolol, and pulegone, wherein the Terpene profile comprises about 20%, 21%, 22%, 23%, 24%, 25%, 26%, 27%, 28%, 29%, or about 30% myrcene by weight.

In some embodiments, the Terpene Profile of the disclosed pharmaceutical comprises β-caryophyllene, myrcene, α-bisabolol, and pulegone, wherein the Terpene profile comprises about 15%-35% α-bisabolol by weight, about 15%-30% α-bisabolol by weight, about 15%-25% α-bisabolol by weight, about 15%-20% α-bisabolol by weight, about 20%-35% α-bisabolol by weight, about 25%-35% α-bisabolol by weight, or about 30%-35% α-bisabolol by weight. In some embodiments, the Terpene Profile of the disclosed pharmaceutical comprises β-caryophyllene, myrcene, α-bisabolol, and pulegone, wherein the Terpene profile comprises about 20%-30% α-bisabolol by weight, about 25%-30% α-bisabolol by weight, or about 20%-25% α-bisabolol by weight. In some embodiments, the Terpene Profile of the disclosed pharmaceutical comprises β-caryophyllene, myrcene, α-bisabolol, and pulegone, wherein the Terpene profile comprises about 20%, 21%, 22%, 23%, 24%, 25%, 26%, 27%, 28%, 29%, or about 30% α-bisabolol by weight.

In some embodiments, the Terpene Profile of the disclosed pharmaceutical comprises (3-caryophyllene, myrcene, α-bisabolol, and pulegone, wherein the Terpene profile comprises about 10%-30% pulegone by weight, about 10%-25% pulegone by weight, about 10%-20% pulegone by weight, about 10%-15% pulegone by weight, about 15%-30% pulegone by weight, about 20%-30% pulegone by weight, or about 25%-30% pulegone by weight. In some embodiments, the Terpene Profile of the disclosed pharmaceutical comprises β-caryophyllene, myrcene, α-bisabolol, and pulegone, wherein the Terpene profile comprises about 15%-25% pulegone by weight, about 15%-20% pulegone by weight, or about 20%-25% pulegone by weight. In some embodiments, the Terpene Profile of the disclosed pharmaceutical comprises β-caryophyllene, myrcene, α-bisabolol, and pulegone, wherein the Terpene profile comprises about 15%, 16%, 17%, 18%, 19%, 20%, 21%, 22%, 23%, 24%, or about 25% pulegone by weight.

In some embodiments, the Terpene Profile of the disclosed pharmaceutical comprises (3-caryophyllene, myrcene, α-bisabolol, and pulegone, wherein the Terpene profile comprises 35%-55% β-caryophyllene by weight, 10%-30% myrcene by weight, 10%-30% α-bisabolol by weight, and 5%-25% pulegone by weight. In some embodiments, the Terpene Profile of the disclosed pharmaceutical comprises β-caryophyllene, myrcene, α-bisabolol, and pulegone, wherein the Terpene profile comprises 40%-50% β-caryophyllene by weight, 15%-25% myrcene by weight, 15%-25% α-bisabolol by weight, and 10%-15% pulegone by weight. In some embodiments, the Terpene Profile of the disclosed pharmaceutical comprises β-caryophyllene, myrcene, α-bisabolol, and pulegone, wherein the Terpene profile comprises 15%-35% β-caryophyllene by weight, 15%-35% myrcene by weight, 15%-35% α-bisabolol by weight, and 10%-30% pulegone by weight. In some embodiments, the Terpene Profile of the disclosed pharmaceutical comprises β-caryophyllene, myrcene, α-bisabolol, and pulegone, wherein the Terpene profile comprises 20%-30% β-caryophyllene by weight, 20%-30% myrcene by weight, 20%-30% α-bisabolol by weight, and 15%-25% pulegone by weight. In such embodiments, the percentage of each of β-caryophyllene, myrcene, α-bisabolol, and pulegone can vary according to the prescribed ranges so long as the total of % β-caryophyllene+% myrcene+% α-bisabolol+% pulegone=100%.

In some embodiments, the Terpene Profile of the disclosed pharmaceutical comprises 3 terpenes selected from the group consisting of α-pinene, valencene, eucalyptol, β-caryophyllene, myrcene, α-bisabolol, and pulegone. In some embodiments, the Terpene Profile of the disclosed pharmaceutical comprises β-caryophyllene, myrcene, and α-bisabolol. In some embodiments, the Terpene Profile comprises in order of relative abundance (low to high):

(a) β-caryophyllene, myrcene, α-bisabolol;
(b) β-caryophyllene, α-bisabolol, myrcene;
(c) myrcene, β-caryophyllene, α-bisabolol;
(d) myrcene, α-bisabolol, β-caryophyllene;
(e) α-bisabolol, β-caryophyllene, myrcene; or
(f) α-bisabolol, myrcene, β-caryophyllene.

In some embodiments, the Terpene Profile of the disclosed pharmaceutical comprises (3-caryophyllene, myrcene, and α-bisabolol at a non-naturally occurring ratio. In some embodiments, the Terpene Profile of the disclosed pharmaceutical comprises β-caryophyllene, myrcene, and α-bisabolol, wherein β-caryophyllene and myrcene are present at a mass ratio of 5:1 to 1:5, 4:1 to 1:4, 3:1 to 1:3, 2:1 to 1:2, or 1:1. In some embodiments, the Terpene Profile comprises β-caryophyllene, myrcene, and α-bisabolol, wherein β-caryophyllene and α-bisabolol are present at a mass ratio of 5:1 to 1:5, 4:1 to 1:4, 3:1 to 1:3, 2:1 to 1:2, or 1:1. In some embodiments, the Terpene Profile comprises β-caryophyllene, myrcene, and α-bisabolol, wherein myrcene and α-bisabolol are present at a mass ratio of 5:1 to 1:5, 4:1 to 1:4, 3:1 to 1:3, 2:1 to 1:2, or 1:1.

In some embodiments, the Terpene Profile of the disclosed pharmaceutical comprises β-caryophyllene, myrcene, and α-bisabolol, wherein the Terpene profile comprises about 20%-40% β-caryophyllene by weight, about 20%-35% β-caryophyllene by weight, about 20%-30% β-caryophyllene by weight, about 20%-25% β-caryophyllene by weight, about 25%-40% β-caryophyllene by weight, about 30%-40% β-caryophyllene by weight, or about 35%-40% β-caryophyllene by weight. In some embodiments, the Terpene Profile of the disclosed pharmaceutical comprises β-caryophyllene, myrcene, and α-bisabolol, wherein the Terpene profile comprises about 30%-40% β-caryophyllene by weight, about 30%-35% β-caryophyllene by weight, or about 35%-40% β-caryophyllene by weight. In some embodiments, the Terpene Profile of the disclosed pharmaceutical comprises β-caryophyllene, myrcene, and α-bisabolol, wherein the Terpene profile comprises about 30%, 31%, 32%, 33%, 34%, 35%, 36%, 37%, 38%, 39% or about 40% β-caryophyllene by weight.

In some embodiments, the Terpene Profile of the disclosed pharmaceutical comprises β-caryophyllene, myrcene, and α-bisabolol, wherein the Terpene profile comprises about 20%-40% myrcene by weight, about 20%-35% myrcene by weight, about 20%-30% myrcene by weight, about 20%-25% myrcene by weight, about 25%-40% myrcene by weight, about 30%-40% myrcene by weight, or about 35%-40% myrcene by weight. In some embodiments, the Terpene Profile of the disclosed pharmaceutical comprises β-caryophyllene, myrcene, and α-bisabolol, wherein the Terpene profile comprises about 30%-40% myrcene by weight, about 30%-35% myrcene by weight, or about 35%-40% myrcene by weight. In some embodiments, the Terpene Profile of the disclosed pharmaceutical comprises β-caryophyllene, myrcene, and α-bisabolol, wherein the Terpene profile comprises about 30%, 31%, 32%, 33%, 34%, 35%, 36%, 37%, 38%, 39% or about 40% myrcene by weight.

In some embodiments, the Terpene Profile of the disclosed pharmaceutical comprises β-caryophyllene, myrcene, and α-bisabolol, wherein the Terpene profile comprises about 20%-40% α-bisabolol by weight, about 20%-35% α-bisabolol by weight, about 20%-30% α-bisabolol by weight, about 20%-25% α-bisabolol by weight, about 25%-40% α-bisabolol by weight, about 30%-40% α-bisabolol by weight, or about 35%-40% α-bisabolol by weight. In some embodiments, the Terpene Profile of the disclosed pharmaceutical comprises β-caryophyllene, myrcene, and α-bisabolol, wherein the Terpene profile comprises about 30%-40% α-bisabolol by weight, about 30%-35% α-bisabolol by weight, or about 35%-40% α-bisabolol by weight. In some embodiments, the Terpene Profile of the disclosed pharmaceutical comprises β-caryophyllene, myrcene, and α-bisabolol, wherein the Terpene profile comprises about 30%, 31%, 32%, 33%, 34%, 35%, 36%, 37%, 38%, 39% or about 40% α-bisabolol by weight.

In some embodiments, the Terpene Profile of the disclosed pharmaceutical comprises β-caryophyllene, myrcene, and α-bisabolol, wherein the Terpene profile comprises 20%-40% β-caryophyllene by weight, 20%-40% myrcene by weight, and 20%-40% α-bisabolol by weight. In some embodiments, the Terpene Profile of the disclosed pharmaceutical comprises β-caryophyllene, myrcene, and α-bisabolol, wherein the Terpene profile comprises 30%-40% β-caryophyllene by weight, 30%-40% myrcene by weight, and 30%-40% α-bisabolol by weight. In such embodiments, the percentage of each of β-caryophyllene, myrcene, and α-bisabolol can vary according to the prescribed ranges so long as the total of % β-caryophyllene+% myrcene+% α-bisabolol=100%.

Exemplary Compositions

In some embodiments, the active ingredient portion of the present disclosure comprises THC, CBD, α-pinene, valencene, and eucalyptol. In some embodiments, the active ingredient portion of the present disclosure consists of THC, CBD, α-pinene, valencene, and eucalyptol. Thus in some embodiments, the active ingredient portion consists of A % THC, B % CBD, C % α-pinene, D % valencene, E % eucalyptol, wherein A, B, C, D, and E can each be 0-100%, so long as A+B+C+D+E=100%. In some embodiments, the active ingredient portion of the present disclosure consists essentially of THC, CBD, α-pinene, valencene, and eucalyptol. In some embodiments, the ratio of total cannabinoids to total terpenes is 4:1, 5:1, 6:1, 7:1, 8:1, 9:1, or 10:1. In some embodiments, the pharmaceutical composition of the present disclosure comprises about 5 mg/mL THC, about 5 mg/mL CBD, about 0.43 mg/mL α-pinene, about 0.43 mg/mL valencene, and about 0.5 mg/mL eucalyptol.

In some embodiments, the active ingredient portion of the present disclosure comprises THC, CBD, β-caryophyllene, myrcene, α-bisabolol, and pulegone. In some embodiments, the active ingredient portion of the present disclosure consists of THC, CBD, β-caryophyllene, myrcene, α-bisabolol, and pulegone. Thus in some embodiments, the active ingredient portion consists of A % THC, B % CBD, C % β-caryophyllene, D % myrcene, E % α-bisabolol, and F % pulegone wherein A, B, C, D, E, and F can each be 0-100%, so long as A+B+C+D+E+F=100%. In some embodiments, the ratio of total cannabinoids to total terpenes is 1:1, 2:1, 3:1, or 4:1.

In some embodiments, the active ingredient portion of the present disclosure comprises THC, CBD, β-caryophyllene, myrcene, and α-bisabolol. In some embodiments, the active ingredient portion of the present disclosure consists of THC, CBD, β-caryophyllene, myrcene, and α-bisabolol. Thus in some embodiments, the active ingredient portion consists of A % THC, B % CBD, C % β-caryophyllene, D % myrcene, and E % α-bisabolol, wherein A, B, C, D, and E can each be 0-100%, so long as A+B+C+D+E=100%. In some embodiments, the ratio of total cannabinoids to total terpenes is 1:1, 2:1, 3:1, or 4:1. In some embodiments, the pharmaceutical composition of the present disclosure comprises about 8.33 mg/mL THC, about 1.66 mg/mL CBD, about 1.8 mg/mL β-caryophyllene, about 1.8 mg/mL myrcene, and about 1.8 mg/mL α-bisabolol.

VIII. Formulations

In some embodiments, additional components are optionally added to the compositions of the present disclosure to improve the taste and/or physical properties of the composition (such as stability, viscosity, appearance of smoke as it is inhaled, etc.). Such additional components include, but are not limited to, sweeteners, natural flavorants, artificial flavorants, colorants, antioxidants, preservatives, chelating agents, viscomodulators, tonicifiers, odorants, opacifiers, suspending agents, binders, thickeners, carriers and mixtures thereof, including, but not limited to, xanthum gum, carboxymethylcellulose, carboxyethylcellulose, hydroxypropylcellulose, methylcellulose, microcrystalline cellulose, starches, dextrins, maltodextrins, other polyols (including sugar alcohols, such as sorbitol, lactitol or mannitol), carbohydrates (e.g., lactose), propylene glycol alginate, gellan gum, guar, pectin, tragacanth gum, gum acacia, locust bean gum, gum arabic, mannitol, sucralose, silicon dioxide, stearic acid, hydroxypropyl methylcellulose, mono-, di- and triglycerides (acyl glycerols), ether and sugar acetates or other acid esters such as dimethyl acetate, ethyl acetate, isopropyl acetate, ethylhexyl acetate, butyl acetate, triethyl citrate, dimethyl butyrate and the like.

In some embodiments, the compositions of the present disclosure are formulated with one or more carriers. The term "carrier" as used herein encompasses carriers, excipients, and diluents, meaning a material, composition or vehicle, such as a liquid or solid filler, diluent, excipient, binder, disintegrant, lubricant, solvent or encapsulating material involved in carrying or transporting a pharmaceutical agent from one organ, or portion of the body, to another organ or portion of the body. The range of materials that are suitable for use as fillers, disintegrants, binders, lubricants, diluents, plasticizers, anti-caking agents, solubilizing agents, stabilizers, anti-oxidants, anti-adherents, preservatives, glidants, flavorants, sweeteners, and pigments will be well known to the person skilled in the art.

Suitable fillers include inert, relatively tasteless or pleasant tasting materials. A nonlimiting list of suitable fillers includes cellulose (e.g. microcrystalline cellulose), starch (e.g. corn starch), pregelatinized starch, modified starch, dibasic calcium phosphate dihydrate, calcium sulfate trihydrate, calcium sulfate dihydrate, calcium carbonate, dextrose, sucrose, lactose, mannitol, and sorbitol. Lactose monohydrate is used as filler in certain embodiments. In certain embodiments, the filler is at least one member selected from the group consisting of: lactose monohydrate, cellulose microcrystalline, corn starch, and combinations thereof.

A nonlimiting list of suitable disintegrants include cross-linked polymers such as crospovidone, croscarmellose sodium, etc., and modified starches such as sodium starch glycolate.

A nonlimiting list of suitable binders includes disaccharides such as sucrose and lactose, polysaccharides such as cellulose, starches, microcrystalline cellulose, modified celluloses such as hydroxypropyl cellulose, sugar alcohols such as xylitol, sorbitol, or maltitol, proteins such as gelatin, synthetic polymers such as polyvinyl pyrrolidone and polyethylene glycol, starches, such as potato starch, wheat starch, corn starch, and gums, such as gum tragacanth, acacia gum and gelatin.

A nonlimiting list of suitable lubricants includes magnesium stearate, stearic acid, sodium stearyl fumarate and the like.

Plasticizers utilized in some embodiments include, but are not limited to, citric and tartaric acid esters (acetyl-triethyl citrate, acetyl tributyl-, tributyl-, triethyl-citrate); glycerol and glycerol esters (glycerol diacetate, -triacetate, acetylated monoglycerides, castor oil); phthalic acid esters (dibutyl-, diamyl-, diethyl-, dimethyl-, dipropyl-phthalate), di-(2-methoxy- or 2-ethoxyethyl)-phthalate, ethylphthalyl glycolate, butylphthalylethyl glycolate and butylglycolate; alcohols (propylene glycol, polyethylene glycol of various chain lengths), adipates (diethyladipate, di-(2-methoxy- or 2-ethoxyethyl)-adipate; benzophenone; diethyl- and dibutylsebacate, dibutylsuccinate, dibutyltartrate; diethylene glycol dipropionate; ethyleneglycol diacetate, dibutyrate, -dipropionate; tributyl phosphate, tributyrin; polyethylene glycol sorbitan monooleate (polysorbates such as Polysorbar 50); sorbitan monooleate.

Exemplary pharmaceutical diluents include without limitation monosaccharides, disaccharides, polyhydric alcohols and mixtures thereof. In some embodiments, pharmaceutical diluents include, for example, starch, mannitol, lactose, dextrose, sucrose, microcrystalline cellulose, sorbitol, xylitol, fructose, and mixtures thereof. In some embodiments, the pharmaceutical diluent is water-soluble. Nonlimiting examples of water-soluble pharmaceutical diluents include lactose, dextrose, sucrose, or mixtures thereof.

Optionally, the formulations may also contain other ingredients such as wetting agents (e.g., polyethoxylated castor oil, polyethoxylated hydrogenated castor oil, polyethoxylated fatty acid from castor oil, polyethoxylated fatty acid from hydrogenated castor oil), flavors, coloring agents, buffering agents, and/or other conventional ingredients.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

Carrier Oil

In one embodiment, the compositions described herein are combined with a carrier oil (i.e., a substance facilitating the administration of the compositions disclosed herein). In one embodiment, the carrier oil is grapeseed oil. In one embodiment, the carrier oil is coconut oil. In one embodiment, the carrier oil is polyethylene glycol. In some embodiments, the carrier oil is olive oil.

In some embodiments, the carrier oil is MCT oil. MCT oil is comprised of medium chain triglycerides and can, in some embodiments, be sourced from coconut oil. MCTs are easily digested and processed in the body.

In a further embodiment, the carrier oil is then combined with a food product. In a further embodiment, the carrier oil is then combined with a beverage product. In a further embodiment, the carrier oil is then combined with a personal care product, e.g., topical cream, soap, shampoo, etc. In a further embodiment, the carrier oil is then combined with a drug. In a further embodiment, the carrier oil is then combined with a non-*Cannabis* plant extract. In a further embodiment, the carrier oil combined with the composition is used with a device, e.g., vaporizer, intravenous drug, etc.

The compositions of the present invention can employ various formulations for administration to subjects including formulation as tablets, capsules, pills, powders, granules, solutions, suspensions, emulsions, elixir, lotion, cream, gel, ointment, tincture, paste, foam, aerosol, irrigation, spray, suppository, or bandage. The form of the resulting formulation depends upon a number of factors, including the intended mode of administration (e.g. oral administration, enteral administration, parenteral administration, and topical application to the skin, scalp, eyes, and/or nasal, buccal or sublingual mucosa), selected carriers or vehicles, the solubility of the composition in the selected carrier or vehicle.

Oral

Oral pharmaceutical dosage forms can be either solid or liquid. The solid dosage forms can be tablets, capsules, granules, and bulk powders. Types of oral tablets include compressed, chewable lozenges and tablets which can be enteric-coated, sugar-coated, or film-coated. Capsules can be hard or soft gelatin capsules, while granules and powders can be provided in non-effervescent or effervescent form with the combination of other ingredients known to those skilled in the art. In other embodiments, the oral dosage form may be an osmotic-controlled release oral delivery system (OROS). In other embodiments, the oral dosage form may include matrix-embedded dosage forms or related devices. In some embodiments, the present oral dosage forms may include orally-disintegrating tablets. Pharmaceutically acceptable carriers utilized in tablets include binders, lubricants, diluents, disintegrating agents, coloring agents, flavoring agents, and wetting agents.

Liquid oral dosage forms include aqueous solutions, emulsions, suspensions, solutions, and/or suspensions reconstituted from non-effervescent granules and effervescent preparations reconstituted from effervescent granules. Aqueous solutions include, for example, elixirs and syrups. Elixirs are clear, sweetened, hydroalcoholic preparations. Pharmaceutically acceptable carriers used in elixirs include solvents. Syrups can be concentrated aqueous solutions of a sugar, for example, sucrose, and can contain a preservative. An emulsion is a two-phase system in which one liquid is dispersed in the form of small globules throughout another liquid, typically oil-in water or water-in-oil. Pharmaceutically acceptable carriers used in emulsions are non-aqueous liquids, emulsifying agents and preservatives. Suspensions can use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substance used in effervescent granules, to be reconstituted into a liquid oral dosage form, can include organic acids and a source of carbon dioxide. Coloring and flavoring agents can be used in all of the above dosage forms.

Enteral

Pharmaceutical dosage forms for rectal administration can be rectal suppositories, capsules and tablets for systemic effect. Rectal suppositories as used herein mean solid bodies for insertion into the rectum which melt or soften at body temperature releasing the pharmacologically and/or therapeutically active ingredients contained in the composition of this invention. Pharmaceutically acceptable substances utilized in rectal suppositories are bases or vehicles and agents to raise the melting point. Examples of bases include cocoa butter (theobroma oil), glycerin-gelatin, carbowax, polyoxyethylene glycol and mixtures of mono-, di- and triglycerides of fatty acids. Combinations of the various bases can be used. Agents to raise the melting point of suppositories include spermaceti and wax. Rectal suppositories can be prepared either by the compressed method or by molding. The typical weight of a rectal suppository is about 2 to 3 gm. Tablets and capsules for rectal administration can be manufactured using the same pharmaceutically acceptable substance and by the same methods as for formulations for oral administration.

Parenteral

Parenteral administration of the formulations of the present invention includes intravenous, subcutaneous, and intramuscular administrations of immediate, sustained, extended, and/or modified release formulations. Preparations for parenteral administration include sterile solutions ready for injection, sterile dry soluble products ready to be combined with a solvent just prior to use, including hypodermic tablets, sterile suspensions ready for injection, sterile dry insoluble products ready to be combined with a vehicle just prior to use and sterile emulsions. The solutions can be either aqueous or nonaqueous. Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents, and other pharmaceutically acceptable substances.

Sustained/Immediate Release

In some embodiments, the compositions described herein are formulated in a dosage form for immediate or sustained release. By "immediate release" formulation is meant a dosage form that is intended to release substantially the entire dose of active ingredient on administration with no enhanced, delayed, controlled, sustained, or extended release effect, generally over a short period of time (e.g., 30 minutes). "Sustained release" or "extended release" means that the active ingredient(s) of the composition is released from the formulation at a controlled rate so that therapeutically beneficial blood levels (but below toxic levels) of the active ingredient(s) are maintained over an extended period of time. Alternatively, "sustained release" or "extended release" means that the desired pharmacologic effect is maintained over an extended period of time.

Tinctures

In some embodiments, the compositions described herein are formulated as a tincture. In aspects, the tincture is formulated to have a chocolate flavor, or a mint flavor, or a mint chocolate flavor. In aspects, the tincture is formulated to have a peppermint flavor. In aspects, the tincture is formulated to have a citrus flavor, such as a grapefruit flavor, a lemon flavor, or an orange flavor. In aspects, the tincture is formulated to have a passionfruit flavor. In aspects, the tincture is formulated to have a vanilla flavor. In aspects, the tincture is formulated to have a ginger flavor. In some embodiments, the tincture is formulated to have a lemon, orange, and ginger flavor. In some embodiments, the tincture is formulated to have an orange and a vanilla flavor.

Sublingual delivery of tincture provides rapid onset of active medicine by delivering the drug very quickly to the bloodstream. Quick delivery to the blood disperses medicine through the body and to the brain. Oral mucosal (e.g. sub- or supralingual) administration of drugs is often the route of administration of choice when the drug shows a large first-pass effect after oral delivery. Systemic exposure of drugs after oral mucosal administration is often expected to be a route of administration with a fast onset of action. See, Bartlett et al., "Understanding the Oral Mucosal Absorption and Resulting Clinical Pharmacokinetics of Asenapine," AAPS PharmSciTech, 2012, Vol. 13(4), pgs. 1110-1115, incorporated by reference herein.

In embodiments, the tinctures of the disclosure are easy to dose. In some aspects, each ML of a tincture contains 5 mg of total cannabinoid. In some embodiments, the tinctures of the present disclosure are formulated with alcohol. In some embodiments, the tinctures of the present disclosure are formulated with an oil, for example olive oil.

Inhalation Delivery

In some embodiments, the compositions described herein are formulated as an inhaler. In some aspects, the compositions described herein are formulated as a nasal spray.

Topical Cream

In some embodiments, the compositions described herein are formulated as a topical cream.

Vaporizable Oil

In some embodiments, the compositions described herein are formulated as a vaporizable oil.

IX. Methods of Use

In some embodiments, the compositions described herein and formulations thereof are administered to a subject in order to treat a disease. In some embodiments, treating refers to the treatment of a disease in a mammal, e.g., in a human, including (a) inhibiting the disease, i.e., arresting disease development or preventing disease progression; (b) relieving the disease, i.e., causing regression of the disease state or relieving one or more symptoms of the disease; and (c) curing the disease, i.e., remission of one or more disease symptoms. In some embodiments, treatment may refer to a short-term (e.g., temporary and/or acute) and/or a long-term (e.g., sustained) reduction in one or more disease symptoms. In some embodiments, treatment results in an improvement or remediation of the symptoms of the disease. In some embodiments, the improvement is an observable or measurable improvement, or may be an improvement in the general feeling of well-being of the subject.

In some embodiments, the subject may be a neonate, a juvenile, or an adult. Of particular interest are mammalian subjects. Mammalian species that may be treated with the present methods include canines and felines; equines; bovines; ovines; etc. and primates, particularly humans. Animal models, particularly small mammals (e.g. mice, rats, guinea pigs, hamsters, rabbits, etc.) may be used for experimental investigations.

The compositions described herein and formulations thereof can be administered to a subject by injection, irrigation, inhalation, consumption, electro-osmosis, hemodialysis, iontophoresis, and other methods known in the art. In some embodiments, administration route is local or systemic. In some embodiments administration route is intraarterial, intracranial, intradermal, intraduodenal, intrammamary, intrameningeal, intraperitoneal, intrathecal, intratumoral, intravenous, intravitreal, ophthalmic, parenteral, spinal, subcutaneous, ureteral, urethral, vaginal, or intrauterine.

In some embodiments, the administration route is by infusion (e.g., continuous or bolus). Examples of methods for local administration, that is, delivery to the site of injury or disease, include through an Ommaya reservoir, e.g. for intrathecal delivery (See e.g., U.S. Pat. Nos. 5,222,982 and 5,385,582, incorporated herein by reference); by bolus injection, e.g. by a syringe, e.g. into a joint; by continuous infusion, e.g. by cannulation, such as with convection (See e.g., US Patent Application Publication No. 2007-0254842, incorporated herein by reference); or by implanting a device upon which the compositions have been reversibly affixed (see e.g. US Patent Application Publication Nos. 2008-0081064 and 2009-0196903, incorporated herein by reference). In some embodiments, the administration route is by topical administration or direct injection. In some embodiments, the compositions described herein may be provided to the subject alone or with a suitable substrate or matrix.

Indications

In some embodiments, the present disclosure provides methods of treating autism comprising administering an effective amount of a composition described herein to a subject in need thereof. In some embodiments, the subject suffers from autism spectrum disorder (ASD) or a pathological condition with one or more of the symptoms of ASD. Non-limiting examples of ASD include Autistic disorder (classic autism), Asperger's disorder (Asperger syndrome), Pervasive developmental disorder not otherwise specified (PDD-NOS), Rett's disorder (Rett syndrome), and Childhood disintegrative disorder (CDD). In some embodiments, the subject suffers from ASD. In some embodiments, the subject suffers from autism.

Autism spectrum disorders (ASDs) are complex neurodevelopmental disabilities characterized by stereotypic behaviors and deficits in communication and social interaction. The term "spectrum" refers to the wide range of symptoms, skills, and levels of impairment, or disability, that patients with ASD can have. ASD is generally diagnosed according to guidelines listed in the Diagnostic and Statistical Manual of Mental Disorders, Fourth Edition-Text Revision (DSM-IV-TR). The manual currently defines five disorders, sometimes called pervasive developmental disorders (PDDs), as ASD, including Autistic disorder (classic autism), Asperger's disorder (Asperger syndrome), Pervasive developmental disorder not otherwise specified (PDD-NOS), Rett's disorder (Rett syndrome), and Childhood disintegrative disorder (CDD). Some patients are mildly impaired by their symptoms, but others are severely disabled.

In some embodiments, the compositions described herein treat one or more symptoms of ASD. In some embodiments, the treatment of the one or more symptoms is assessed by behavioral performance of the subject including assessment of language ability, and adaptive function.

The behavioral test can include, but is not limited to, detecting the presence and/or extent of 1) preoccupation with one or more stereotyped and restricted patterns of interest that is abnormal in either intensity or focus, 2) inflexible adherence to specific, nonfunctional routines or rituals, c) stereotyped and repetitive motor mannerisms (such as hand flapping, finger flapping etc.), and/or d) persistent preoccupation with parts of objects. Non-limiting examples of behavior that can be included in a behavioral test and suggest a need for improving behavioral performance in the subject under the test include: a) sensory behaviors, including poor use of visual discrimination when learning, seems not to hear, so that a hearing loss is suspected, sometimes shows no "startle response" to loud noise", sometimes painful stimuli such as bruises, cuts, and injections evoke no reaction, often will not blink when bright light is directed toward eyes, covers ears at many sounds, squints, frowns, or covers eyes when in the presence of natural light, frequently has no visual reaction to a "new" person, stares into space for long periods of time; b) relating behaviors: frequently does not attend to social/environmental stimuli, has no social smile, does not reach out when reached for, non-responsive to other people's facial expressions/feelings, actively avoids eye contact, resists being touched or held, is flaccid when held in arms, is stiff and hard to held, does not imitate other children at play, has not developed any friendships, often frightened or very anxious, "looks through" people; c) body and object use behaviors: whirls self for long periods of time, does not use toys appropriately, insists on keeping certain objects with him/her, rocks self for long periods of time, does a lot of lunging and darting, flaps hands, walks on toes, hurts self by banging head, biting hand, etc. . . . , twirls, spins, and bangs objects a lot, will feel, smell, and/or taste objects in the environment, gets involved in complicated "rituals" such as lining things up, etc. . . . , is very destructive; and d) language behaviors: does not follow simple commands given once, has pronoun reversal, speech is atonal, does not respond to own name when called out among two others, seldom says "yes" or "I", does not follow simple commands involving prepositions, gets desired objects by gesturing, repeats phrases over and over, cannot point to more than five named objects, uses 0-5 spontaneous words per day to communicate wants and needs, repeats sounds or words over and over, echoes questions or statements made by others, uses at least 15 but less than 30 spontaneous phrases daily to communicate, learns a simple task but "forgets" quickly, strong reactions to changes in routine/environment, has "special abilities" in one area of development, which seems to rule out mental retardation, severe temper tantrums and/or frequent minor tantrums, hurts others by biting, hitting, kicking, etc. . . . , does not wait for needs to be met, difficulties with toileting, does not dress self without frequent help, frequently unaware of surroundings, and may be oblivious to dangerous situations, prefers to manipulate and be occupied with inanimate things. One of ordinary skill in the art would appreciate that the attending physician would know how to identify a subject in need of treatment disclosed herein.

In some embodiments, the behavioral performance of a subject is assessed using the Vineland Adaptive Behavior Scales (Vineland Adaptive Behavior Scales: Interview Edition, American Guidance Service, Circle Pines, Minnesota, 1984), the Child Behavior Checklist (Achenbach, Manual for the Child Behavior Checklist 14-18 University of Vermont Department of Psychiatry, 1981), the Autism Behavior Checklist (ABC), Autism diagnostic Interview-Revised (ADI-R), Childhood Autism Rating Scale (CARS) (Schopler et al, Journal of Autism and Developmental Disorders, 1980; 19:91-103), and/or Pre-Linguistic Autism Diagnostic Observation Schedule (PL-ADOS).

Treatment Regimens

Typically, a therapeutically effective amount of a pharmaceutical composition is administered. The effective amount of a particular pharmaceutical composition may be represented in a variety of ways based on the nature of the pharmaceutical composition, such as mass/volume or (mass of the composition)/(mass of a subject). The effective amount of a particular composition may also be expressed as the half-maximal effective concentration ($EC_{50}$), which refers to the concentration of the composition that results in a magnitude of a particular physiological response that is half-way between a reference level and a maximum response level. The therapeutically effective dose can be determined by a person having ordinary skill in the art upon perusal of the disclosure according to known considerations and appropriate measurements. For example, in some embodiments, the therapeutically effective dose is the dose or amount effective reduce one or more symptoms or characteristics of ASD.

In some embodiments, the therapeutically effective dose of the active ingredient portion of the presently disclosed pharmaceutical composition ranges from about 0.5 mg/kg to about 50 mg/kg, such as, for example, from about or from about 0.5 mg/kg to about 40 mg/kg, 0.5 mg/kg to about 30 mg/kg, 0.5 mg/kg to about 20 mg/kg, 0.5 mg/kg to about 10 mg/kg, from about 0.5 mg/kg to about 6 mg/kg, from about 0.5 mg/kg to about 4 mg/kg, from about 0.5 mg/kg to about 2 mg/kg, from about 0.5 mg/kg to about 1.8 mg/kg, from about 0.5 mg/kg to about 1.6 mg/kg, from about 0.5 mg/kg to about 1.4 mg/kg, from about 0.5 mg/kg to about 1.2 mg/kg, from about 0.5 mg/kg to about 1 mg/kg, from about 0.5 mg/kg to about 0.8 mg/kg, or from about 0.5 mg/kg to about 0.6 mg/kg. Each possibility is a separate embodiment of the invention.

Thus, in some embodiments, the present disclosure provides active ingredient portion doses of 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 31 mg/kg, 32 mg/kg, 33 mg/kg, 34 mg/kg, 35 mg/kg, 36 mg/kg, 37 mg/kg, 38 mg/kg, 39 mg/kg, 40 mg/kg, 41 mg/kg, 42 mg/kg, 43 mg/kg, 44 mg/kg, 45 mg/kg, 46 mg/kg, 47 mg/kg, 48 mg/kg, 49 mg/kg, 50 mg/kg, and any ranges and subranges there between.

In some embodiments, the average daily dose of the active ingredient portion of the present disclosure for a human subject (such as a human child, weighing between about 10 kg and about 40 kg or a human adult, weighing between about 40 kg and about 120 kg) can be about 5 mg, about 10 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 200 mg, about 300 mg, about 400 mg, about 500 mg about 600 mg, about 700 mg, about 800 mg, about 900 mg, about 1000 mg, about 1100 mg, about 1200 mg, about 1300 mg, or about 1400 mg. Each possibility is a different embodiment of the invention.

In some embodiments, a treatment regime may comprise administering typically between 2.5 mL to 5 mL of a composition described herein to a subject in need thereof. In aspects, as aforementioned, 1 mL of a tincture may contain 5 mg of total cannabinoid. This treatment regime can be administered on an "as needed" basis. In aspects, the appropriate treatment regime is adjusted as needed based on results of AUC studies in appropriate patient populations.

In some embodiments, treatment comprises delivering an effective amount of a composition described herein or formulation thereof to a subject in need thereof. The effective amount of a composition administered to a particular subject will depend on a variety of factors, several of which will differ from patient to patient including the disorder being treated and the severity of the disorder; activity of the specific agent(s) employed; the age, body weight, general health, sex and diet of the patient; the timing of administration, route of administration; the duration of the treatment; drugs used in combination; the judgment of the prescribing physician; and like factors known in the medical arts.

According to some embodiments of the present invention, administering of compositions described herein provides statistically significant therapeutic effect. In one embodiment, the statistically significant therapeutic effect is determined based on one or more standards or criteria provided by one or more regulatory agencies in the United States, e.g., FDA or other countries. In another embodiment, the statistically significant therapeutic effect is determined based on results obtained from regulatory agency approved clinical trial set up and/or procedure.

In some embodiments, the statistically significant therapeutic effect is determined by a randomized double blind clinical trial of patients treated with compositions described herein and optionally in combination with standard care. In some embodiment, the statistically significant therapeutic effect is determined by a randomized clinical trial and using Numerical Rating Scale (NRS) as primary efficacy parameter and optionally in combination with any other commonly accepted criteria for pruritus assessment.

In general, statistical analysis can include any suitable method permitted by a regulatory agency, e.g., FDA in the US or Europe or any other country. In some embodiments, statistical analysis includes non-stratified analysis, log-rank analysis, e.g., from Kaplan-Meier, Jacobson-Truax, Gulliken-Lord-Novick, Edwards-Nunnally, Hageman-Arrindel and Hierarchical Linear Modeling (HLM) and Cox regression analysis.

Pharmacokinetics

According to some embodiments of the present invention, the methods of the present invention provide therapeutically effective blood plasma levels of a composition described herein for treating autism. Herein, reference to detection and/or quantification of blood levels of a composition refers to the detection and/or quantification of total cannabinoids in a sample obtained from a subject (i.e., a blood sample). Blood plasma levels of compositions described herein may be expressed using pharmacokinetic parameters that are known to those skilled in the art, such as steady state plasma levels, AUC, Cmax and Cmin.

In some embodiments, the present methods provide steady state plasma levels of compositions described herein that correlate to one or more statistically significant therapeutic effects. In certain embodiments, the therapeutically effective steady state plasma levels of compositions described herein provided by the methods of the present invention range from about 1 ng/mL to about 200 ng/mL, including about 1 ng/ml, about 5 ng/mL, about 10 ng/mL, about 15 ng/mL, about 20 ng/mL, about 25 ng/mL, about 30 ng/mL, about 35 ng/mL, about 40 ng/mL, about 45 ng/mL, about 50 ng/mL, about 55 ng/mL, about 60 ng/mL, about 65 ng/mL, about 70 ng/mL, about 75 ng/mL about 80 ng/mL, about 85 ng/mL, about 90 ng/mL, about 95 ng/mL, about 100 ng/mL, about 105 ng/mL, about 110 ng/mL, about 115 ng/mL, about 120 ng/mL, about 125 ng/mL, about 130 ng/mL, about 135 ng/mL, about 140 ng/mL, about 145 ng/mL, about 150 ng/mL, about 155 ng/mL, about 160 ng/mL, about 165 ng/mL, about 170 ng/mL, about 175 ng/mL about 180 ng/mL, about 185 ng/mL, about 190 ng/mL, about 195 ng/mL, and 200 ng/ml, including all ranges there between.

In some embodiments, the blood plasma level of compositions described herein characterized by one or more peaks followed by a plateau region. The plateau region is characterized as having a relatively consistent blood plasma level of compositions described herein (e.g., the blood plasma level of compositions described herein does not consistently increase or decrease from time point to time point). In some embodiments, the plateau region is characterized as having a consistent average blood plasma level of compositions described herein. The plateau region is contrasted with the region following the plateau region, in which the blood plasma level of compositions described herein generally decreases from one time point to the next. In some embodiments, the plateau region has a duration of at least about 1 hour, about 2 hours, about 3 hours, about 4 hours, about 5 hours, about 6 hours, about 7 hours, about 8 hours, about 9 hours, about 10 hours, about 11 hours or about 12 hours. In some embodiments, the plateau region has a duration from about 1 hour to about 12 hours, from about 2 hours to about 10 hours, from about 2 hours to about 8 hours, from about 2 hours to about 7 hours or from about 4 hours to about 10 hours, from about 4 hours to about 8 hours, or from about 4 hours to about 6 hours. In some embodiments, the blood plasma level of compositions described herein at each time point in the plateau region ranges from about 75% to about 125% of the mean blood plasma level in the plateau region. In some embodiments, the blood plasma level of compositions described herein at each time point in the plateau region ranges from about 80% to about 120% of the mean blood plasma level in the plateau region. In some embodiments, the blood plasma level of compositions described herein at each time point in the plateau region ranges from about 85% to about 115% of the mean blood plasma level in the plateau region. In some embodiments, the blood plasma level of compositions described herein at each time point in the plateau region ranges from about 90% to about 110% of the mean blood plasma level in the plateau region.

In some embodiments, the present methods provide mean steady state AUC 0-24 h (expressed in terms of ng*hr/mL) levels of compositions described herein that correlate to one or more statistically significant therapeutic effects. In certain embodiments, the therapeutically effective mean steady state AUC 0-24 h levels of compositions described herein range from about 50 ng*hr/mL to about 2300 ng*hr/mL, including about 50 ng*hr/mL, 100 ng*hr/mL, 150 ng*hr/mL, 200 ng*hr/mL, 250 ng*hr/mL, 300 ng*hr/mL, about 400 ng*hr/mL, about 500 ng*hr/mL, about 600 ng*hr/mL, about 700 ng*hr/mL, about 800 ng*hr/mL, about 900 ng*hr/mL, about 1000 ng*hr/mL, about 1100 ng*hr/mL, about 1200 ng*hr/mL, about 1300 ng*hr/mL, about 1400 ng*hr/mL, about 1500 ng*hr/mL, about 1600 ng*hr/mL, about 1700 ng*hr/mL, about 1800 ng*hr/mL, about 1900 ng*hr/mL, about 2000 ng*hr/mL, about 2100 ng*hr/mL, about 2200 ng*hr/mL, about 2300 ng*hr/mL, including all ranges there between.

In some embodiments, the present methods provide steady state plasma Cmax levels of compositions described herein that correlate to one or more statistically significant therapeutic effects. In certain embodiments, the therapeutically effective steady state plasma Cmax levels of compositions described herein of the present invention range from about 5 ng/mL to about 500 ng/mL, including about 5 ng/mL, 10 ng/mL, 20 ng/mL, 30 ng/mL, 40 ng/mL, 50 ng/mL, 60 ng/mL, about 70 ng/mL, about 80 ng/mL, about 90 ng/mL, about 100 ng/mL, about 110 ng/mL, about 120 ng/mL, about 130 ng/mL, about 140 ng/mL, about 150 ng/mL, about 160 ng/mL, about 170 ng/mL about 180 ng/mL, about 190 ng/mL, about 200 ng/mL, about 210 ng/mL, about 220 ng/mL, about 230 ng/mL, about 240 ng/mL, about 250 ng/mL, about 260 ng/mL, about 270 ng/mL about 280 ng/mL, about 290 ng/mL, about 300 ng/mL, about 310 ng/mL, about 320 ng/mL, about 330 ng/mL, about 340 ng/mL, about 350 ng/mL, about 360 ng/mL, about 370 ng/mL about 380 ng/mL, about 390 ng/mL, about 400 ng/mL, about 410 ng/mL, about 420 ng/mL, about 430 ng/mL, about 440 ng/mL, about 150 ng/mL, about 460 ng/mL, about 470 ng/mL about 480 ng/mL, about 490 ng/mL, about 400 ng/mL, and about 500 ng/mL, including all ranges there between.

FURTHER NUMBERED EMBODIMENTS

Further numbered embodiments of the present disclosure are as follows:

Embodiment 1. A pharmaceutical composition for the treatment of autism, comprising: (a) a Cannabinoid Profile comprising two or more cannabinoids, wherein the two or more cannabinoids comprise Tetrahydrocannabinol (THC) and Cannabidiol (CBD); and (b) a Terpene Profile comprising two or more terpenes selected from α-Pinene, Valencene, Eucalyptol, β-Caryophyllene (BCP), Myrcene, α-Bisabolol, and Pulegone.

Embodiment 2. The pharmaceutical composition of Embodiment 1, wherein the ratio of THC:CBD is 1:1.

Embodiment 3. The pharmaceutical composition of Embodiment 1, wherein the ratio of THC:CBD is 5:1.

Embodiment 4. The pharmaceutical composition of any one of Embodiments 1-3, wherein the Terpene Profile comprises α-Pinene, Valencene, and Eucalyptol.

Embodiment 5. The pharmaceutical composition of Embodiment 4, wherein the Terpene Profile comprises, in order of relative abundance (from low to high): (a) α-Pinene, Valencene, and Eucalyptol; (b) α-Pinene, Eucalyptol, and Valencene; (c) Valencene, α-Pinene, and Eucalyptol; (d) Valencene, Eucalyptol, and α-Pinene; (e) Eucalyptol, α-Pinene, and Valencene; or (f) Eucalyptol, Valencene, and α-Pinene.

Embodiment 6. The pharmaceutical composition of Embodiment 4, wherein the Terpene Profile comprises 15%-35% α-Pinene, 15%-35% Valencene, and 40%-60% Eucalyptol, wherein the total of % α-Pinene+% Valencene+% Eucalyptol=100%.

Embodiment 7. The pharmaceutical composition of Embodiment 4, wherein the Terpene Profile comprises 20%-40% α-Pinene, 20%-40% Valencene, and 20%-40% Eucalyptol, wherein the total of % α-Pinene+% Valencene+% Eucalyptol=100%.

Embodiment 8. The pharmaceutical composition of Embodiment 4, wherein the Terpene Profile comprises 20%-40% α-Pinene, 20%-40% Valencene, and 30%-50% Eucalyptol, wherein the total of % α-Pinene+% Valencene+% Eucalyptol=100%.

Embodiment 9. The pharmaceutical composition of Embodiment 4, wherein the Terpene Profile comprises 25%-35% α-Pinene, 25%-35% Valencene, and 30%-40% Eucalyptol, wherein the total of % α-Pinene+% Valencene+% Eucalyptol=100%.

Embodiment 10. The pharmaceutical composition of any one of Embodiments 1-3, wherein the Terpene Profile comprises BCP, Myrcene, α-Bisabolol, and Pulegone.

Embodiment 11. The pharmaceutical composition of Embodiment 10, wherein the Terpene Profile comprises, in order of relative abundance (from low to high): (a) BCP, myrcene, α-bisabolol, and pulegone; (b) BCP, myrcene, pulegone, and α-bisabolol; (c) BCP, pulegone, myrcene, and α-bisabolol; (d) BCP, pulegone, α-bisabolol, and myrcene; (e) BCP, α-bisabolol, pulegone, and myrcene; (f) BCP, α-bisabolol, myrcene, and pulegone; (g) α-bisabolol, BCP, myrcene, and pulegone; (h) α-bisabolol, BCP, pulegone, and myrcene; (i) α-bisabolol, myrcene, BCP, and pulegone; (j) α-bisabolol, myrcene, pulegone, and BCP; (k) α-bisabolol, pulegone, myrcene, and BCP; (l) α-bisabolol, pulegone, BCP, and myrcene; (m) myrcene, α-bisabolol, BCP, and pulegone; (n) myrcene, α-bisabolol, pulegone, and BCP; (o) myrcene, BCP, α-bisabolol, and pulegone; (p) myrcene, BCP, pulegone, and α-bisabolol; (q) myrcene, pulegone, BCP, and α-bisabolol; (r) myrcene, pulegone, α-bisabolol, and BCP; (s) pulegone, myrcene, α-bisabolol, and BCP; (t) pulegone, myrcene, BCP, and α-bisabolol; (u) pulegone, α-bisabolol, myrcene, and BCP; (v) pulegone, α-bisabolol, BCP, and myrcene; (w) pulegone, BCP, α-bisabolol, and myrcene; or (x) pulegone, BCP, myrcene, and α-bisabolol.

Embodiment 12. The pharmaceutical composition of Embodiment 10, wherein the Terpene Profile comprises 35%-55% BCP, 10%-30% Myrcene, 10%-30% α-Bisabolol, and 5%-20% Pulegone, wherein the total of % BCP+% Myrcene+% α-Bisabolol+% Pulegone=100%.

Embodiment 13. The pharmaceutical composition of Embodiment 10, wherein the Terpene Profile comprises 15%-35% BCP, 15%-35% Myrcene, 15%-35% α-Bisabolol, and 10%-30% Pulegone, wherein the total of % BCP+% Myrcene+% α-Bisabolol+% Pulegone=100%.

Embodiment 14. The pharmaceutical composition of any one of Embodiments 1-3, wherein the Terpene Profile comprises BCP, Myrcene, and α-Bisabolol.

Embodiment 15. The pharmaceutical composition of Embodiment 14, wherein the Terpene Profile comprises, in order of relative abundance: (a) β-caryophyllene, myrcene, α-bisabolol; (b) β-caryophyllene, α-bisabolol, myrcene; (c) myrcene, β-caryophyllene, α-bisabolol; (d) myrcene, α-bisabolol, β-caryophyllene; (e) α-bisabolol, β-caryophyllene, myrcene; or (f) α-bisabolol, myrcene, β-caryophyllene Embodiment 16. The pharmaceutical composition of Embodiment 14, wherein the Terpene Profile comprises 20%-40% BCP, 20%-40% Myrcene, and 20%-40% α-Bisabolol, wherein the total of % BCP+% Myrcene+% α-Bisabolol=100%.

Embodiment 17. The pharmaceutical composition of Embodiment 14, wherein the Terpene Profile comprises 30%-40% BCP, 30%-40% Myrcene, and 30%-40% α-Bisabolo, wherein the total of % BCP+% Myrcene+% α-Bisabolol=100%.

Embodiment 18. A pharmaceutical composition for the treatment of autism, comprising: (a) a Cannabinoid Profile comprising Tetrahydrocannabinol (THC) and Cannabidiol (CBD) present at a 1:1 ratio; and (b) a Terpene Profile comprising α-Pinene, Valencene, and Eucalyptol.

Embodiment 19. The pharmaceutical composition of Embodiment 18, wherein the Terpene Profile comprises 15%-35% α-Pinene, 15%-35% Valencene, and 40%-60% Eucalyptol, wherein the total of % α-Pinene+% Valencene+% Eucalyptol=100%.

Embodiment 20. The pharmaceutical composition of Embodiment 18, wherein the Terpene Profile comprises 20%-40% α-Pinene, 20%-40% Valencene, and 20%-40% Eucalyptol, wherein the total of % α-Pinene+% Valencene+% Eucalyptol=100%.

Embodiment 21. The pharmaceutical composition of Embodiment 18, wherein the Terpene Profile comprises 20%-40% α-Pinene, 20%-40% Valencene, and 30%-50% Eucalyptol, wherein the total of % α-Pinene+% Valencene+% Eucalyptol=100%.

Embodiment 22. The pharmaceutical composition of Embodiment 18, wherein the Terpene Profile comprises 25%-35% α-Pinene, 25%-35% Valencene, and 30%-40% Eucalyptol, wherein the total of % α-Pinene+% Valencene+% Eucalyptol=100%.

Embodiment 23. The pharmaceutical composition of any one of Embodiments 18-22, wherein the ratio of total cannabinoids to total terpenes is between 10:1 and 5:1.

Embodiment 24. A pharmaceutical composition for the treatment of autism, comprising: (a) a Cannabinoid Profile comprising Tetrahydrocannabinol (THC) and Cannabidiol (CBD) present at a 5:1 ratio; and (b) a Terpene Profile comprising β-Caryophyllene (BCP), Myrcene, α-Bisabolol, and Pulegone.

Embodiment 25. The pharmaceutical composition of Embodiment 24, wherein the Terpene Profile comprises 35%-55% BCP, 10%-30% Myrcene, 10%-30% α-Bisabolol, and 5%-20% Pulegone, wherein the total of % BCP+% Myrcene+% α-Bisabolol+% Pulegone=100%.

Embodiment 26. The pharmaceutical composition of Embodiment 24, wherein the Terpene Profile comprises 15%-35% BCP, 15%-35% Myrcene, 15%-35% α-Bisabolol, and 10%-30% Pulegone, wherein the total of % BCP+% Myrcene+% α-Bisabolol+% Pulegone=100%.

Embodiment 27. A pharmaceutical composition for the treatment of autism, comprising: (a) a Cannabinoid Profile comprising Tetrahydrocannabinol (THC) and Cannabidiol (CBD) present at a 5:1 ratio; and (b) a Terpene Profile comprising (3-Caryophyllene (BCP), Myrcene, and α-Bisabolol.

Embodiment 28. The pharmaceutical composition of Embodiment 27, wherein the Terpene Profile comprises 20%-40% BCP, 20%-40% Myrcene, and 20%-40%

α-Bisabolol, wherein the total of % BCP+% Myrcene+% α-Bisabolol=100%.

Embodiment 29. The pharmaceutical composition of Embodiment 27, wherein the Terpene Profile comprises 30%-40% BCP, 30%-40% Myrcene, and 30%-40% α-Bisabolo, wherein the total of % BCP+% Myrcene+% α-Bisabolol=100%.

Embodiment 30. A pharmaceutical composition comprising: (a) a Cannabinoid Profile comprising Tetrahydrocannabinol (THC) and Cannabidiol (CBD) present at a 1:1 ratio; and (b) a Terpene Profile comprising α-Pinene, Valencene, and Eucalyptol, wherein the Terpene Profile comprises about 25% by weight α-Pinene, about 25% by weight Valencene, and about 50% by weight Eucalyptol.

Embodiment 31. A pharmaceutical composition comprising: (a) a Cannabinoid Profile comprising Tetrahydrocannabinol (THC) and Cannabidiol (CBD) present at a 1:1 ratio; and (b) a Terpene Profile comprising α-Pinene, Valencene, and Eucalyptol, wherein the Terpene Profile comprises about 31% by weight α-Pinene, about 31% by weight Valencene, and about 37.5% by weight Eucalyptol.

Embodiment 32. A pharmaceutical composition comprising: (a) a Cannabinoid Profile comprising about 5 mg/mL Tetrahydrocannabinol (THC) and about 5 mg/mL Cannabidiol (CBD); and (b) a Terpene Profile comprising α-Pinene, Valencene, and Eucalyptol, wherein the Terpene Profile comprises about 0.43 mg/mL α-Pinene, about 0.43 mg/mL Valencene, and about 0.5 mg/mL Eucalyptol.

Embodiment 33. A pharmaceutical composition comprising: (a) a Cannabinoid Profile comprising Tetrahydrocannabinol (THC) and Cannabidiol (CBD) present at a 5:1 ratio; and (b) a Terpene Profile comprising β-Caryophyllene (BCP), Myrcene, α-Bisabolol, and Pulegone, wherein the Terpene Profile comprises about 45% by weight BCP, about 21% by weight Myrcene, about 21% by weight α-Bisabolol, and about 12% by weight Pulegone.

Embodiment 34. A pharmaceutical composition comprising: (a) a Cannabinoid Profile comprising Tetrahydrocannabinol (THC) and Cannabidiol (CBD) present at a 5:1 ratio; and (b) a Terpene Profile comprising β-Caryophyllene (BCP), Myrcene, and α-Bisabolol, wherein the Terpene Profile comprises about 33% by weight BCP, about 34% by weight Myrcene, and about 33% by weight α-Bisabolol.

Embodiment 35. A pharmaceutical composition comprising: (a) a Cannabinoid Profile comprising 8.33 mg/mL Tetrahydrocannabinol (THC) and 1.67 mg/mL Cannabidiol (CBD); and (b) a Terpene Profile comprising β-Caryophyllene (BCP), Myrcene, and α-Bisabolol, wherein the Terpene Profile comprises about 1.8 mg/mL BCP, about 1.8 mg/mL Myrcene, and about 1.8 mg/mL α-Bisabolol.

Embodiment 36. The pharmaceutical composition of any one of Embodiments 1-35, wherein the ratio of total cannabinoids to total terpenes is between 1:1 and 3:1.

Embodiment 37. The pharmaceutical composition of any one of Embodiments 1-36, wherein the terpenes in the Terpene Profile are present at a non-naturally occurring ratio.

Embodiment 38. The pharmaceutical composition of any one of Embodiments 1-37, further comprising one or more non-*Cannabis* plant extracts.

Embodiment 39. The pharmaceutical composition of any one of Embodiments 1-37, wherein at least one of the active ingredients is an enriched active ingredient.

Embodiment 40. The pharmaceutical composition of any one of Embodiment 1-37, wherein each of the active ingredients is an enriched active ingredient.

Embodiment 41. The pharmaceutical composition of any one of Embodiments 1-37, wherein at least one of the active ingredients is a substantially pure active ingredient.

Embodiment 42. The pharmaceutical composition of any one of Embodiments 1-37, wherein each of the active ingredients is a substantially pure active ingredient.

Embodiment 43. The pharmaceutical composition of any one of Embodiments 1-42, further comprising one or more flavors.

Embodiment 44. The pharmaceutical composition of Embodiment 43, wherein the one or more flavors are selected from orange, ginger, vanilla, raspberry, blackberry, grapefruit, and mint chocolate.

Embodiment 45. The pharmaceutical composition of any one of Embodiments 1-44, wherein the composition is formulated for oral administration.

Embodiment 46. The pharmaceutical composition of Embodiment 45, wherein the composition is formulated as a liquid dose.

Embodiment 47. The pharmaceutical composition of Embodiment 46, wherein the composition is formulated as a tincture.

Embodiment 48. The pharmaceutical composition of any one of Embodiments 1-44, wherein the composition is formulated for parenteral administration.

Embodiment 49. The pharmaceutical composition of Embodiment 48, wherein the composition is formulated for buccal administration, as an oral mucosal absorption spray, as a transdermal patch, cream or ointment, or for intravenous administration.

Embodiment 50. A method of treating autism, comprising: administering an effective amount of the pharmaceutical composition of any one of Embodiments 1-49 to a subject in need thereof.

Embodiment 51. A method of improving self-stimulatory behavior in patients with autism spectrum disorder (ASD), said method comprising the steps of administering a pharmaceutical composition comprising (a) a Cannabinoid Profile comprising Tetrahydrocannabinol (THC) and Cannabidiol (CBD) present at a 5:1 ratio; and (b) a Terpene Profile comprising β-Caryophyllene (BCP), Myrcene, α-Bisabolol, and Pulegone, wherein the Terpene Profile comprises about 45% by weight BCP, about 21% by weight Myrcene, about 21% by weight α-Bisabolol, and about 12% by weight Pulegone.

Embodiment 52. A method of improving self-stimulatory behavior in patients with autism spectrum disorder (ASD), said method comprising the steps of administering the pharmaceutical composition of any one of Embodiments 1-49.

Embodiment 53. A method of improving communication behavior in patients with autism spectrum disorder (ASD), said method comprising the steps of administering the pharmaceutical composition of any one of Embodiments 1-49.

Embodiment 54. A method of improving communication behavior in patients with autism spectrum disorder (ASD), said method comprising the steps of administering the pharmaceutical composition of any one of Embodiments 1-49.

Embodiment 55. The method of any one of Embodiments 50-54, wherein the pharmaceutical composition is administered as a 2 mL, 2.5 mL, 3 mL, 3.5 mL, 4 mL, 4.5 mL, or 5 mL dose.

EXAMPLES

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 1—HOPE™ Formulations

The following tables represent exemplary formulations of the HOPE-1 and HOPE-2 therapeutics.

TABLE 1

HOPE-1 Tincture Formulation

|  | % Volume | % Mass |
|---|---|---|
| Cannabinoid Distillate (300 mg total, 1:1 THC:CBD) | 1.26%* | 1.310%* |
| RBD Olive Oil | 96.58%* | 96.756%* |
| α-Pinene | 0.05% | 0.045% |
| Valencene | 0.05% | 0.045% |
| Eucalyptol | 0.06% | 0.054% |
| Chocolate-Mint Flavor | 2.00% | 1.791% |
| Total Formula % | 100.00% | 100.00% |

TABLE 2

HOPE-2_v2 Tincture Formulation

|  | % Volume | % Mass |
|---|---|---|
| Cannabinoid Distillate (300 mg total, 5:1 THC:CBD) | 1.12% | 1.171% |
| RBD Olive Oil | 95.53% | 95.676% |
| β-Caryophyllene | 0.20% | 0.188% |
| Myrcene | 0.20% | 0.193% |
| α-Bisabolol | 0.20% | 0.188% |
| Grapefruit Flavor | 2.75% | 2.585% |
| Total Formula % | 100.00% | 100.00% |

Example 2—Evaluation of Pharmacokinetics and Self-Reported Therapeutic Effects of HOPE™ Formulations Studies are performed to evaluate the pharmacokinetics (PK) and self-reported therapeutic effects of HOPE-1 and HOPE-2.

Study Objectives and Summary

Study goals: The primary goal of this study is to quantitatively describe the PK profile of HOPE-1 and HOPE-2 medical marijuana products in patients who are taking these products based on recommendation of their health care providers. The secondary goal of this study is to describe the pharmacodynamic effects of medical marijuana initiated as an additional/alternative standard therapy in a variety of state-approved conditions via self-reported mechanisms.

Compliance: This study is conducted in full accordance with all applicable Children's Hospital of Philadelphia Research Policies and Procedures and all applicable Federal and state laws and regulations including 45 CFR 46, and the HIPAA Privacy Rule. The investigators will perform the study in accordance with this protocol, will obtain consent and assent (unless a waiver is granted), and will report unexpected problems in accordance with The Children's Hospital of Philadelphia IRB Policies and Procedures and all federal requirements. Collection, recording, and reporting of data will be accurate and will ensure the privacy, health, and welfare of research subjects during and after the study Summary: This is an observational study of medical marijuana manufactured by Ilera and given as standard treatment for a variety of approved serious medical conditions as defined by individual state law. Once the study team confirms eligibility, the study team will meet the subject face-to-face most likely at their dispensary (or other mutually agreeable location) and obtain informed consent, and assent when appropriate. Initial baseline demographic information, medical history, and medication inventory will be completed. The subjects or their LARs will be instructed on obtaining the blood samples. Blood draws will be completed in the subjects' home after one of their standard doses is taken. A schedule of study procedures is provided in Table 3 below. Pharmacodynamic parameters including patient reported overall effectiveness and adverse events of the medication in treating symptoms will be recorded.

TABLE 3

Schedule of Study Procedures

| Study Phase | Screening | Intake | PK visit (may be repeating per protocol) |
|---|---|---|---|
| Review Inclusion/Exclusion Criteria | X | X | X |
| Informed Consent/Assent | X |  | X |
| Demographics | X | X | X |
| Medical History/Medical Marijuana Utilization |  | X | X |
| Prior/Concomitant Medications |  | X | X |
| PK blood draws |  |  | X |

Investigational Plan:

This is a prospective PK/PD study that will include patients who are currently legally consuming one of HOPE-1 and HOPE-2 as part of their standard therapy for one of the state approved serious medical conditions.

Part 1 of the study consists of intake data of select subjects. Once consent is obtained, demographic information will be collected as well as a medical and medication history and several questions related specifically to the medical marijuana product and its perceived effectiveness. The data will be recorded in the REDCAP database.

Part 2 of the study consists of pharmacokinetic evaluation of select subjects. Parents/care providers/patients when appropriate will undergo education regarding PK sample acquisition. PK blood samples will be obtained and sent to CHOP for determination of CBD/THC/CBN concentrations. PK and PD analysis will occur.

Study Population

A total of 64 patients will be enrolled. There will be 4-12 patients enrolled into each of the 4 different age cohorts for each product.

(a) Inclusion criteria: Individuals who consume either HOPE-1 and HOPE-2 medical marijuana in a state which has legalized medical marijuana for state specified serious medical conditions, have provided written informed consent and assent (if applicable), and are older than 2 years of age.

(b) Exclusion Criteria: Individuals who consume marijuana products that are not obtained from a state licensed dispensary, non-English speaking individuals, and individuals who have consumed a CBD/THC containing product other than the product under study within the 7 days prior to the PK study.

Study Procedures

Part 1—Data Registry

All data will be extracted from subject interviews by a member of the study team (research assistant, research coordinator, or co-investigator). Interviews will happen with a trained member of the study team. Data will be entered directly into a single CHOP database (REDCap) or will be documented on a paper CRF and then entered into the database.

Screening: Eligibility of subjects is determined by the study team and consent/assent is obtained prior to any study procedures. If a subject is determined to be ineligible at any point, their participation in the study will end.

Initial Intake: Patient demographic information including past medical history, social history, care givers (if they are obtaining the medication for the patient), concurrent medications, care provider (only specialty and institution will be documented) and Medical marijuana data including product name, recommended indication for use, dose/route/frequency, dispensary, use history (start date, other marijuana use), and storage at home is collected.

Outcomes: Relief of primary indication (perceived therapeutic benefit of product through self-report (scale of 1-10)) and side effects Part 2—Pharmacokinetics PK Sample Timing: Subjects will undergo PK sampling for the determination of cannabinoid concentrations based on the formulation that is being consumed (e.g. If a subject is taking only CBD, THC concentrations will not be measured). A subject may provide blood samples more than once if they change products. All subjects will undergo a PK sampling at the approximate times: Prior to dose consumption, 1 hour after completion of dose, 2-3 hours after dose, 4-6 hours after dose, 8-12 hours or immediately prior to next dose PK Sample Approach: PK samples are obtained using a micro-sampling approach. The micro-sampling approach requires 10-30 microliters of blood on Mitra®tips that utilizes volumetric absorptive microsampling (VAMS™) technology. This approach requires a small pinprick to obtain a fixed volume (20 µL of blood) drop of blood that is then placed on each Mitra® tip. The tip is allowed to air dry and then is ready for processing and determination of drug quantification. Subjects will be educated regarding the technique, and provided with lidocaine cream to numb the sites and minimize discomfort.

PK Sample Location: Subjects can perform PK sampling at home. Training videos and worksheets will be provided to the patients and/or caregivers to perform the PK sampling. Subjects will either be given the PK kits at the time of consent or be shipped all necessary supplies, directions, packaging for return shipping and study team contact information for questions and additional support.

PK Sample Processing: All PK samples will be assayed for respective drug concentrations in the Bioanalytical Core Lab within the Center for Clinical Pharmacology at Children's Hospital of Philadelphia.

Subject Completion Withdrawal: Subjects may withdraw from the study at any time without prejudice to their care. They may also be discontinued from the study at the discretion of the Investigator for lack of adherence to schedules, or no longer taking medical marijuana products. The investigator may also withdraw subjects who violate the study plan, or to protect the subject for reasons of safety or for administrative reasons. If the subject is withdrawn from the study, it will be recorded in the source documents and on the CRF.

Measurements:

Relevant PK parameters including bioavailability, volume(s) of distribution, clearance(s), half-life, and therapeutic range are determined.

The primary evaluation is the assessment of marijuana pharmacokinetics. Data from all fully evaluable subjects is included in the analysis. The following pharmacokinetic parameters are estimated using the NONMEM statistical algorithm:

(a) Bioavailability
(b) Plasma clearance (CL)
(c) Volume of distributions (Vd)
(d) Terminal elimination half-life (t½)

The pharmacokinetic analysis is performed using both standard model dependent and model independent methods. A two-compartment open model with first-order elimination from the central compartment is fit to the concentration-time data from all evaluable subjects. Summary statistics for these parameters are tabulated. Geometric means and coefficients of variation are presented for AUC and end of infusion concentration. Mean, standard deviations, and ranges are presented for t½, Vd and Cl.

Clinical Adverse Events: Unanticipated problems involving risk to subjects or others will be monitored throughout the study.

Adverse Event Reporting: As the study procedures are not greater than minimal risk, SAEs are not expected. If any unanticipated problems related to the research involving risks to subjects or others happen during the course of this study (including SAEs) these will be reported to the IRB in accordance with CHOP IRB SOP 408: Unanticipated Problems Involving Risks to Subjects. AEs that are not serious but that are notable and could involve risks to subjects will be summarized in narrative or other format and submitted to the IRB at the time of continuing review.

Example 3—Evaluation of Subject Preference of HOPE™ Formulations

Experiments were performed to assess subject preference for select HOPE-1 and HOPE-2 formulations. Briefly, subjects were given 1 mL tinctures of HOPE-1 and HOPE-2 formulations comprising Terpene Profiles and one or more flavoring additives. These formulations did not include Cannabinoid Profiles. After sampling the different formulations, subjects were asked to rate each of the samples on a scale of 1 to 5 for i) color/appearance; ii) flavor/taste quality; iii) aroma/odor; and iv) texture/mouthfeel, where 1=lowest/ least preferred, 5=highest/most preferred, and NA=not applicable to a particular sample. The three groups of subjects tested were autistic children ("Autistic", n=4), non-autistic caregivers ("Network Control", n=5), and non-autistic non-caregiver controls ("Non-autistic control", n=9).

Five formulations of HOPE-1 and four formulations of HOPE-2 were tested. Table 4 below summarizes the Terpene Profile and flavor profile for each formulation.

TABLE 4

Summary of HOPE ™ Formulations

|  | Formulation ID | Terpene Profile | Flavor Profile |
|---|---|---|---|
| HOPE-1 | HOPE-1a* | α-Pinene, Valencene, Eucalyptol | Peppermint-High |
|  | HOPE-1a | α-Pinene, Valencene, Eucalyptol | Peppermint-Low |
|  | HOPE-2a | α-Pinene, Valencene, Eucalyptol | Vanilla |
|  | HOPE-3a | α-Pinene, Valencene, Eucalyptol | Lemon, Orange, Ginger |
|  | HOPE-4a | α-Pinene, Valencene, Eucalyptol | Passionfruit |
| HOPE-2_v1 | HOPE-1b | β-caryophyllene, Myrcene, α-Biabolol, Pulegone | Peppermint |
|  | HOPE-2b | β-caryophyllene, Myrcene, α-Biabolol, Pulegone | Vanilla |
|  | HOPE-3b | β-caryophyllene, Myrcene, α-Biabolol, Pulegone | Lemon, Orange, Ginger |
|  | HOPE-4b | β-caryophyllene, Myrcene, α-Biabolol, Pulegone | Orange, Vanilla |
| HOPE-2_v2 |  | β-caryophyllene, Myrcene, α-Biabolol | Grapefruit |

Table 5 below provides the results from this experiment. For each formulation, the response values were aggregated such that a given formulation has a maximum value of 20 (i.e., received a "5" in each of the four categories).

TABLE 5

Results of HOPE ™ Formulation Preference Study

|  | 1a* | 1a | 2a | 3a | 4a | 1b | 2b | 3b | 4b |
|---|---|---|---|---|---|---|---|---|---|
| Autistic | 14 | 14 | 18 | 15 | 12 | 14 | 12 | 14 | 16 |
| Autistic | 14 | 12 | 10 | 14 |  | 13 | 9 | 17 | 11 |
| Autistic | 17 | 16 | 18 | 18 | 8 | 11 | 15 | 19 | 19 |
| Autistic | 11 | 12 | na |  |  | 11 | 9 | 17 | 6 |
| Average | 14 | 13.5 | 15.3 | 15.67 | 10 | 12.25 | 11.25 | 16.75 | 13 |
| Network Control | 13 | 9 | 12 | 12 | 12 | 12 | 12 | 12 | 12 |
| Network Control | 9 | 12 | 15 | 9 | 9 | 9 | 9 | 12 | 9 |
| Network Control | 7 | 7 | 12 | 11 | 11 | 7 | 10 | 13 | 9 |
| Network Control | 9 | 10 | 12 | 13 | 14 | 12 | 7 | 10 | 9 |
| Network Control | 14 | 14 | 15 | 12 | 18 | 12 | 15 | 15 | 13 |
| Average | 10.4 | 10.4 | 13.2 | 11.4 | 12.8 | 10.4 | 10.6 | 12.4 | 10.4 |
| Non-autistic control | 17 | 17 | 20 | 20 | 19 | 13 | 15 | 16 | 10 |
| Non-autistic control | 14 | 9 | 15 | 11 | 11 | 12 | 14 | 16 | 17 |
| Non-autistic control | 14 | 12 | 16 | 16 | 14 | 7 | 12 | 17 | 11 |
| Non-autistic control | 15 | 15 | 15 | 19 | 15 | 11 | 10 | 19 | 15 |
| Non-autistic control | 13 | 12 | 12 | 19 | 16 | 13 | 11 | 15 | 13 |
| Non-autistic control | 16 | 15 | 12 | 16 | 16 | 18 | 16 | 17 | 14 |
| Non-autistic control | 19 | 15 | 11 | 6 | 5 | 14 | 11 | 11 | 16 |
| Non-autistic control | 20 | 14 |  | 20 | 15 |  | 12 | 7 |  |
| Non-autistic control | 14 | 12 | 16 | 13 | 11 | 15 | 15 | 13 | 10 |
| Average | 15.78 | 13.4 | 14.63 | 15.56 | 13.56 | 12.88 | 12.89 | 14.56 | 13.25 |

The data shown above suggest that autism patients may have a preference for certain taste profile. In some aspects, the autistic subjects preferred formulations with peppermint taste profiles.

Example 4—Feedback Survey of HOPE-1 and HOPE-2 Users with ASD

The survey was conducted through the HOPE GROWS online community of over 700 families and patient advocacy groups for use of *Cannabis*-based solutions in Pennsylvania. Patients eligible to participate in the survey met the following criteria: (i) received a Commonwealth of Pennsylvania approved recommendations for medical *Cannabis*; and (ii) purchased one or both of the HOPE tincture products from an approved PA dispensary.

The purpose of the survey was to obtain early information on the self-reported efficacy of the HOPE products since it was approved for used by the Pennsylvania Department of Health under the Medical Marijuana Program. Responses for the first 51 participants in the survey were analyzed and presented in this report. The range of autism diagnoses are shown in Table 6 and Table 7.

TABLE 6

Aggregate Autism Diagnoses

| Diagnosis | Number of Respondents |
| --- | --- |
| High-functioning | 6 (11%) |
| Mild | 2 (3.9%) |
| Moderate | 13 (25%) |
| Severe | 19 (37%) |
| Other-non-autistic | 11 (22%) |

TABLE 7

Autism Diagnoses by Respondent

| Respondent ID | Diagnosis |
| --- | --- |
| 10851106117 | High Functioning |
| 10829184646 | High Functioning |
| 10822204795 | High Functioning |
| 10788786575 | High Functioning |
| 10788519306 | High Functioning |
| 10776855365 | High Functioning |
| 10826208510 | Mild |
| 10817495561 | Mild |
| 10825515762 | Moderate |
| 10822398076 | Moderate |
| 10814575232 | Moderate |
| 10807666173 | Moderate |
| 10801066482 | Moderate |
| 10793988068 | Moderate |
| 10788106271 | Moderate |
| 10779042448 | Moderate |
| 10773960005 | Moderate |
| 10773094960 | Moderate |
| 10772321917 | Moderate |
| 10771971313 | Moderate |
| 10771894838 | Moderate |
| 10830136536 | Other- Not Autism |
| 10827335246 | Other- Not Autism |
| 10827257244 | Other- Not Autism |
| 10822947935 | Other- Not Autism |
| 10822630399 | Other- Not Autism |
| 10822564175 | Other- Not Autism |
| 10822464684 | Other- Not Autism |
| 10822446884 | Other- Not Autism |
| 10822434643 | Other- Not Autism |
| 10822410399 | Other- Not Autism |
| 10772818740 | Other- Not Autism |
| 10851519475 | Severe |
| 10825432095 | Severe |
| 10825341898 | Severe |
| 10803351239 | Severe |
| 10794101213 | Severe |
| 10793580188 | Severe |
| 10793421202 | Severe |
| 10788699953 | Severe |
| 10788193676 | Severe |
| 10776831268 | Severe |
| 10776563927 | Severe |
| 10773714755 | Severe |
| 10772498533 | Severe |
| 10772442051 | Severe |
| 10772343271 | Severe |
| 10772305396 | Severe |
| 10772265471 | Severe |
| 10771899854 | Severe |
| 10771895798 | Severe |

Participants began using one or both of the formulated HOPE tinctures between April 2019 and Jun. 30, 2019. Respondents' use of the HOPE tinctures is provided in Table 8 and Table 9 below. Approximately 16 (31%) of respondents used another cannabinoid product (e.g., THC oil in fractionated coconut oil, Liberty Blueberry from Liberty Cannabis, Standard Farms products, or Lazarus Naturals CBD oil) in addition to the HOPE-1 or HOPE-2 products. The symptoms that participants were looking to treat include irritability, anxiety, focus and attention, meltdowns, insomnia, communication, hyperactivity, self-stimulatory behaviors, self-injurious behaviors, and obsessive compulsiveness.

TABLE 8

Aggregate Formulation usage

| Diagnosis | Number of Respondents |
| --- | --- |
| HOPE-1 | 9 |
| HOPE-2 | 28 |
| HOPE-1 and HOPE-2 | 12 |

TABLE 9

Formulation usage by respondent

| Respondent ID | HOPE-1 | HOPE-2 | HOPE-1 and -2 | THC and/or Other |
| --- | --- | --- | --- | --- |
| 10851106117 | | | X | |
| 10829184646 | | X | | |
| 10822204795 | | X | | |
| 10788786575 | | X | | |
| 10788519306 | X | | | |
| 10776855365 | | X | | X |
| 10826208510 | | | X | X |
| 10817495561 | | | X | |
| 10825515762 | | X | | |
| 10822398076 | X | | | |
| 10814575232 | X | | | |
| 10807666173 | | X | | |
| 10801066482 | | X | | X |
| 10793988068 | | X | | |
| 10788106271 | | X | | X |
| 10779042448 | | X | | |
| 10773960005 | X | | | |
| 10773094960 | | X | | |

TABLE 9-continued

Formulation usage by respondent

| Respondent ID | HOPE-1 | HOPE-2 | HOPE-1 and -2 | THC and/or Other |
|---|---|---|---|---|
| 10772321917 | | | X | |
| 10771971313 | | X | | |
| 10771894838 | | X | | |
| 10830136536 | | X | | X |
| 10827335246 | | | X | |
| 10827257244 | X | | | |
| 10822947935 | | X | | |
| 10822630399 | | | | X |
| 10822564175 | | X | | |
| 10822464684 | X | | | X |
| 10822446884 | X | | | X |
| 10822434643 | | | X | |
| 10822410399 | | X | | |
| 10772818740 | | | | X |
| 10851519475 | | | X | |
| 10825432095 | | X | | X |
| 10825341898 | X | | | |
| 10803351239 | | X | | |
| 10794101213 | | X | | |
| 10793580188 | | X | | |
| 10793421202 | | X | | |
| 10788699953 | X | | | X |
| 10788193676 | | X | | |
| 10776831268 | | X | | X |
| 10776563927 | | X | | |
| 10773714755 | | X | | |
| 10772498533 | | X | | |
| 10772442051 | | | X | |
| 10772343271 | | X | | X |
| 10772305396 | | X | | X |
| 10772265471 | | X | | X |
| 10771899854 | | X | | |
| 10771895798 | | X | | X |

The effects of the HOPE-1 and HOPE-2 tinctures on the symptoms for all respondents to be treated are provided in Tables 10-12 below. Additionally, feedback on improvements in overall quality of life for both the treated individual and the family of the individual are shown for all respondents in Table 13.

TABLE 10

Effects of HOPE Formulations on Symptoms by Respondents

| Respondent ID | Diagnosis | Aggression | Irritability | Meltdowns | Anxiety | Obsessive Compulsiveness |
|---|---|---|---|---|---|---|
| 10851106117 | High Functioning | Improved | NA | Improved | NA | Improved |
| 10829184646 | High Functioning | Improved | Improved | Improved | Improved | No Change |
| 10822204795 | High Functioning | Improved | Improved | Improved | No Change | NA |
| 10788786575 | High Functioning | Improved | Improved | Improved | Worsened | No Change |
| 10788519306 | High Functioning | No Change | Worsened | No Change | Worsened | No Change |
| 10776855365 | High Functioning | No Change | No Change | No Change | Improved | No Change |
| 10826208510 | Mild | No Change | Improved | No Change | Improved | Improved |
| 10817495561 | Mild | Improved | Improved | Improved | Improved | Improved |
| 10825515762 | Moderate | Worsened | Worsened | Worsened | Worsened | Worsened |
| 10822398076 | Moderate | No Change | No Change | Improved | Improved | No Change |
| 10814575232 | Moderate | Improved | Improved | No Change | Improved | NA |
| 10807666173 | Moderate | No Change | No Change | No Change | No Change | No Change |
| 10801066482 | Moderate | Worsened | Worsened | Worsened | No Change | Worsened |
| 10793988068 | Moderate | No Change | Improved | No Change | Improved | No Change |
| 10788106271 | Moderate | Improved | Improved | Improved | Improved | Improved |
| 10779042448 | Moderate | Improved | Improved | Improved | No Change | No Change |
| 10773960005 | Moderate | Improved | Improved | Improved | NA | No Change |
| 10773094960 | Moderate | Improved | Improved | Improved | NA | NA |
| 10772321917 | Moderate | NA | Improved | Improved | No Change | Improved |
| 10771971313 | Moderate | No Change | No Change | NA | No Change | No Change |
| 10771894838 | Moderate | Improved | Improved | Improved | NA | NA |
| 10830136536 | Other- Not Autism | NA | NA | NA | Improved | NA |
| 10827335246 | Other- Not Autism | NA | NA | NA | NA | NA |
| 10827257244 | Other- Not Autism | Improved | Improved | Improved | Improved | Improved |
| 10822947935 | Other- Not Autism | No Change | Improved | NA | Improved | NA |
| 10822630399 | Other- Not Autism | Improved | Improved | Improved | Improved | Improved |
| 10822564175 | Other- Not Autism | NA | NA | NA | Improved | NA |
| 10822464684 | Other- Not Autism | Improved | Improved | Improved | Improved | Improved |
| 10822446884 | Other- Not Autism | NA | Improved | NA | Improved | Improved |

TABLE 10-continued

Effects of HOPE Formulations on Symptoms by Respondents

| Respondent ID | Diagnosis | Aggression | Irritability | Meltdowns | Anxiety | Obsessive Compulsiveness |
|---|---|---|---|---|---|---|
| 10822434643 | Other- Not Autism | NA | NA | NA | NA | NA |
| 10822410399 | Other- Not Autism | Improved | Improved | No Change | Improved | No Change |
| 10772818740 | Other- Not Autism | No Change | No Change | No Change | Worsened | Improved |
| 10851519475 | Severe | Worsened | Improved | No Change | Improved | No Change |
| 10825432095 | Severe | Improved | Improved | Improved | Improved | No Change |
| 10825341898 | Severe | Worsened | Worsened | Worsened | NA | NA |
| 10803351239 | Severe | NA | NA | NA | NA | NA |
| 10794101213 | Severe | Improved | Improved | Improved | Improved | Improved |
| 10793580188 | Severe | No Change | No Change | No Change | No Change | No Change |
| 10793421202 | Severe | Improved | No Change | Improved | No Change | No Change |
| 10788699953 | Severe | Improved | Improved | Improved | No Change | No Change |
| 10788193676 | Severe | Improved | Improved | Improved | Improved | Improved |
| 10776831268 | Severe | No Change | Worsened | No Change | Worsened | No Change |
| 10776563927 | Severe | Worsened | Worsened | NA | Worsened | Worsened |
| 10773714755 | Severe | NA | Improved | Improved | No Change | Worsened |
| 10772498533 | Severe | Worsened | Worsened | Improved | No Change | Worsened |
| 10772442051 | Severe | Improved | Improved | Improved | Improved | No Change |
| 10772343271 | Severe | Improved | Improved | Worsened | No Change | No Change |
| 10772305396 | Severe | NA | Improved | NA | No Change | No Change |
| 10772265471 | Severe | Improved | Improved | Improved | Improved | Improved |
| 10771899854 | Severe | Worsened | Improved | Improved | No Change | Worsened |
| 10771895798 | Severe | Improved | Improved | Improved | Improved | No Change |

TABLE 11

Effects of HOPE Formulations on Symptoms by Respondents

| Respondent ID | Diagnosis | Focus - ADD/ADHD symptoms | Seizures | Communication | GI Issues | Insomnia |
|---|---|---|---|---|---|---|
| 10851106117 | High Functioning | Improved | NA | Improved | NA | NA |
| 10829184646 | High Functioning | No Change | NA | Improved | No Change | Improved |
| 10822204795 | High Functioning | NA | NA | NA | Improved | Improved |
| 10788786575 | High Functioning | Worsened | NA | Improved | Improved | NA |
| 10788519306 | High Functioning | No Change | NA | No Change | NA | Worsened |
| 10776855365 | High Functioning | No Change | NA | NA | NA | NA |
| 10826208510 | Mild | Improved | No Change | Improved | No Change | Improved |
| 10817495561 | Mild | Worsened | NA | No Change | Improved | Improved |
| 10825515762 | Moderate | Worsened | Worsened | Worsened | Worsened | Worsened |
| 10822398076 | Moderate | No Change | NA | No Change | Worsened | No Change |
| 10814575232 | Moderate | No Change | NA | No Change | Improved | No Change |
| 10807666173 | Moderate | NA | No Change | No Change | NA | No Change |
| 10801066482 | Moderate | No Change | No Change | No Change | No Change | Worsened |
| 10793988068 | Moderate | No Change | No Change | No Change | No Change | No Change |
| 10788106271 | Moderate | Improved | Improved | Improved | Improved | Improved |
| 10779042448 | Moderate | Improved | NA | Improved | NA | Worsened |
| 10773960005 | Moderate | No Change | NA | No Change | No Change | NA |
| 10773094960 | Moderate | NA | NA | NA | NA | NA |
| 10772321917 | Moderate | No Change | NA | Improved | No Change | NA |
| 10771971313 | Moderate | No Change | NA | No Change | NA | No Change |
| 10771894838 | Moderate | Improved | NA | Improved | Improved | NA |
| 10830136536 | Other- Not Autism | NA | NA | NA | NA | NA |
| 10827335246 | Other- Not Autism | NA | NA | NA | No Change | NA |
| 10827257244 | Other- Not Autism | Improved | NA | Improved | NA | Improved |
| 10822947935 | Other- Not Autism | NA | NA | NA | NA | NA |
| 10822630399 | Other- Not Autism | Improved | Improved | Improved | Improved | Improved |

TABLE 11-continued

Effects of HOPE Formulations on Symptoms by Respondents

| | | | | | | |
|---|---|---|---|---|---|---|
| 10822564175 | Other- Not Autism | NA | NA | NA | NA | No Change |
| 10822464684 | Other- Not Autism | Improved | No Change | Improved | No Change | Improved |
| 10822446884 | Other- Not Autism | NA | NA | NA | Improved | Improved |
| 10822434643 | Other- Not Autism | NA | NA | NA | NA | NA |
| 10822410399 | Other- Not Autism | No Change | No Change | No Change | Improved | Improved |
| 10772818740 | Other- Not Autism | Improved | NA | Improved | Improved | Worsened |
| 10851519475 | Severe | Improved | NA | Improved | No Change | No Change |
| 10825432095 | Severe | No Change | No Change | No Change | No Change | Worsened |
| 10825341898 | Severe | NA | NA | No Change | NA | Worsened |
| 10803351239 | Severe | NA | NA | Improved | NA | NA |
| 10794101213 | Severe | Improved | No Change | Improved | Improved | Improved |
| 10793580188 | Severe | No Change | NA | No Change | NA | NA |
| 10793421202 | Severe | No Change | No Change | No Change | No Change | Improved |
| 10788699953 | Severe | Improved | No Change | No Change | No Change | No Change |
| 10788193676 | Severe | Improved | No Change | Improved | No Change | No Change |
| 10776831268 | Severe | Worsened | NA | No Change | Worsened | Worsened |
| 10776563927 | Severe | Worsened | NA | No Change | No Change | No Change |
| 10773714755 | Severe | NA | NA | No Change | NA | NA |
| 10772498533 | Severe | Improved | NA | Improved | No Change | Worsened |
| 10772442051 | Severe | Improved | NA | Improved | No Change | No Change |
| 10772343271 | Severe | Improved | NA | No Change | No Change | NA |
| 10772305396 | Severe | NA | NA | Improved | No Change | Improved |
| 10772265471 | Severe | No Change | NA | Improved | NA | Worsened |
| 10771899854 | Severe | No Change | NA | Improved | No Change | Worsened |
| 10771895798 | Severe | No Change | NA | No Change | No Change | No Change |

| Respondent ID | Diagnosis | Self-Stimulatory Behavior and Nonfunctional Vocalizations | Hyperactivity | Pain | Appetite |
|---|---|---|---|---|---|
| 10851106117 | High Functioning | NA | Worsened | NA | No Change |
| 10829184646 | High Functioning | Worsened | Worsened | NA | Improved |
| 10822204795 | High Functioning | NA | NA | NA | NA |
| 10788786575 | High Functioning | Improved | Worsened | NA | NA |
| 10788519306 | High Functioning | NA | NA | NA | Worsened |
| 10776855365 | High Functioning | NA | Improved | NA | NA |
| 10826208510 | Mild | Improved | Improved | Improved | No Change |
| 10817495561 | Mild | Worsened | Worsened | | Worsened |
| 10825515762 | Moderate | Worsened | Worsened | Worsened | Worsened |
| 10822398076 | Moderate | NA | NA | NA | NA |
| 10814575232 | Moderate | NA | Improved | NA | NA |
| 10807666173 | Moderate | No Change | No Change | NA | NA |
| 10801066482 | Moderate | Worsened | Worsened | No Change | Worsened |
| 10793988068 | Moderate | No Change | No Change | No Change | No Change |
| 10788106271 | Moderate | Improved | Improved | Improved | Improved |
| 10779042448 | Moderate | No Change | No Change | NA | NA |
| 10773960005 | Moderate | NA | No Change | NA | No Change |
| 10773094960 | Moderate | NA | NA | NA | No Change |
| 10772321917 | Moderate | Worsened | Improved | NA | Improved |
| 10771971313 | Moderate | No Change | No Change | NA | No Change |
| 10771894838 | Moderate | Improved | Improved | NA | No Change |
| 10830136536 | Other- Not Autism | NA | NA | Improved | NA |
| 10827335246 | Other- Not Autism | NA | NA | No Change | NA |
| 10827257244 | Other- Not Autism | NA | NA | NA | NA |
| 10822947935 | Other- Not Autism | NA | NA | Improved | NA |
| 10822630399 | Other- Not Autism | Improved | Improved | Improved | Improved |
| 10822564175 | Other- Not Autism | NA | NA | NA | NA |
| 10822464684 | Other- Not Autism | Improved | Improved | Improved | Improved |
| 10822446884 | Other- Not Autism | NA | Improved | Improved | NA |
| 10822434643 | Other- Not Autism | NA | NA | Improved | No Change |

TABLE 11-continued

Effects of HOPE Formulations on Symptoms by Respondents

| | | | | | |
|---|---|---|---|---|---|
| 10822410399 | Other- Not Autism | No Change | No Change | Improved | Improved |
| 10772818740 | Other- Not Autism | Worsened | Worsened | Improved | No Change |
| 10851519475 | Severe | No Change | NA | NA | No Change |
| 10825432095 | Severe | No Change | No Change | No Change | No Change |
| 10825341898 | Severe | Worsened | Worsened | NA | NA |
| 10803351239 | Severe | NA | NA | NA | NA |
| 10794101213 | Severe | Improved | Improved | No Change | Improved |
| 10793580188 | Severe | No Change | NA | No Change | No Change |
| 10793421202 | Severe | Improved | Improved | No Change | No Change |
| 10788699953 | Severe | No Change | No Change | No Change | No Change |
| 10788193676 | Severe | Improved | Improved | No Change | Improved |
| 10776831268 | Severe | Improved | Improved | NA | Worsened |
| 10776563927 | Severe | Worsened | Worsened | NA | No Change |
| 10773714755 | Severe | Worsened | NA | NA | No Change |
| 10772498533 | Severe | Worsened | Worsened | NA | No Change |
| 10772442051 | Severe | Improved | Improved | NA | NA |
| 10772343271 | Severe | No Change | No Change | NA | NA |
| 10772305396 | Severe | Improved | NA | NA | NA |
| 10772265471 | Severe | No Change | No Change | NA | No Change |
| 10771899854 | Severe | No Change | No Change | NA | No Change |
| 10771895798 | Severe | No Change | No Change | No Change | Improved |

TABLE 12

Effects of HOPE Formulations on Symptoms by Respondents

| Respondent ID | Diagnosis | Rage | Agitation | Self-Injurious Behaviors |
|---|---|---|---|---|
| 10851106117 | High Functioning | Improved | Improved | NA |
| 10829184646 | High Functioning | No Change | No Change | NA |
| 10822204795 | High Functioning | Improved | Improved | Improved |
| 10788786575 | High Functioning | Improved | Improved | Improved |
| 10788519306 | High Functioning | NA | NA | NA |
| 10776855365 | High Functioning | NA | NA | NA |
| 10826208510 | Mild | No Change | Improved | No Change |
| 10817495561 | Mild | Improved | Improved | NA |
| 10825515762 | Moderate | Worsened | Worsened | Worsened |
| 10822398076 | Moderate | NA | NA | NA |
| 10814575232 | Moderate | NA | NA | Improved |
| 10807666173 | Moderate | No Change | No Change | NA |
| 10801066482 | Moderate | No Change | Worsened | No Change |
| 10793988068 | Moderate | No Change | Improved | No Change |
| 10788106271 | Moderate | Improved | Improved | Improved |
| 10779042448 | Moderate | NA | NA | NA |
| 10773960005 | Moderate | NA | Improved | NA |
| 10773094960 | Moderate | Improved | Improved | Improved |
| 10772321917 | Moderate | NA | Worsened | Improved |
| 10771971313 | Moderate | NA | No Change | NA |
| 10771894838 | Moderate | NA | Improved | Improved |
| 10830136536 | Other- Not Autism | NA | NA | NA |
| 10827335246 | Other- Not Autism | NA | NA | NA |
| 10827257244 | Other- Not Autism | NA | NA | NA |
| 10822947935 | Other- Not Autism | NA | NA | NA |
| 10822630399 | Other- Not Autism | Improved | Improved | Improved |
| 10822564175 | Other- Not Autism | NA | NA | NA |
| 10822464684 | Other- Not Autism | Improved | Improved | Improved |
| 10822446884 | Other- Not Autism | NA | NA | NA |
| 10822434643 | Other- Not Autism | NA | NA | NA |
| 10822410399 | Other- Not Autism | No Change | No Change | No Change |
| 10772818740 | Other- Not Autism | Worsened | Worsened | NA |
| 10851519475 | Severe | No Change | No Change | Improved |
| 10825432095 | Severe | Improved | Improved | Improved |
| 10825341898 | Severe | Worsened | Worsened | Worsened |
| 10803351239 | Severe | NA | NA | NA |
| 10794101213 | Severe | Improved | Improved | Improved |
| 10793580188 | Severe | No Change | No Change | No Change |
| 10793421202 | Severe | No Change | No Change | No Change |
| 10788699953 | Severe | Improved | Improved | Improved |
| 10788193676 | Severe | Improved | Improved | Improved |
| 10776831268 | Severe | No Change | Improved | Improved |
| 10776563927 | Severe | NA | Worsened | NA |
| 10773714755 | Severe | NA | Worsened | NA |
| 10772498533 | Severe | Worsened | No Change | Worsened |
| 10772442051 | Severe | Improved | Improved | Improved |
| 10772343271 | Severe | NA | Worsened | NA |
| 10772305396 | Severe | NA | Improved | NA |
| 10772265471 | Severe | No Change | No Change | Improved |
| 10771899854 | Severe | Improved | No Change | Worsened |
| 10771895798 | Severe | Improved | Improved | Improved |

TABLE 13

Quality of life for individuals and families

| Respondent ID | Diagnosis | Overall quality of life for the Individual | Overall quality of life for the entire Family |
|---|---|---|---|
| 10851106117 | High Functioning | Improvement of quality of life | Improvement of quality of life |
| 10829184646 | High Functioning | Improvement of quality of life | Improvement of quality of life |
| 10822204795 | High Functioning | Improvement of quality of life | Improvement of quality of life |
| 10788786575 | High Functioning | Improvement of quality of life | Improvement of quality of life |
| 10788519306 | High Functioning | | |
| 10776855365 | High Functioning | Improvement of quality of life | Improvement of quality of life |
| 10826208510 | Mild | Improvement of quality of life | Improvement of quality of life |
| 10817495561 | Mild | Improvement of quality of life | Improvement of quality of life |
| 10825515762 | Moderate | Decrease in quality of life | Decrease in quality of life |
| 10822398076 | Moderate | Improvement of quality of life | About the same quality of life |
| 10814575232 | Moderate | Improvement of quality of life | Improvement of quality of life |
| 10807666173 | Moderate | About the same quality of life | About the same quality of life |
| 10801066482 | Moderate | Decrease in quality of life | Decrease in quality of life |
| 10793988068 | Moderate | Improvement of quality of life | |
| 10788106271 | Moderate | Improvement of quality of life | Improvement of quality of life |
| 10779042448 | Moderate | Improvement of quality of life | Improvement of quality of life |
| 10773960005 | Moderate | About the same quality of life | About the same quality of life |
| 10773094960 | Moderate | Improvement of quality of life | Improvement of quality of life |
| 10772321917 | Moderate | About the same quality of life | About the same quality of life |
| 10771971313 | Moderate | About the same quality of life | About the same quality of life |
| 10771894838 | Moderate | Improvement of quality of life | Improvement of quality of life |
| 10830136536 | Other-Not Autism | Improvement of quality of life | Improvement of quality of life |
| 10827335246 | Other-Not Autism | About the same quality of life | About the same quality of life |
| 10827257244 | Other-Not Autism | | |
| 10822947935 | Other-Not Autism | Improvement of quality of life | |
| 10822630399 | Other-Not Autism | Improvement of quality of life | Improvement of quality of life |
| 10822564175 | Other-Not Autism | About the same quality of life | About the same quality of life |
| 10822464684 | Other-Not Autism | Improvement of quality of life | Improvement of quality of life |
| 10822446884 | Other-Not Autism | Improvement of quality of life | Improvement of quality of life |
| 10822434643 | Other-Not Autism | Improvement of quality of life | |
| 10822410399 | Other-Not Autism | Improvement of quality of life | About the same quality of life |
| 10772818740 | Other-Not Autism | Improvement of quality of life | About the same quality of life |
| 10851519475 | Severe | Improvement of quality of life | Improvement of quality of life |
| 10825432095 | Severe | Improvement of quality of life | Improvement of quality of life |
| 10825341898 | Severe | Decrease in quality of life | Decrease in quality of life |
| 10803351239 | Severe | Improvement of quality of life | Improvement of quality of life |
| 10794101213 | Severe | Improvement of quality of life | Improvement of quality of life |
| 10793580188 | Severe | About the same quality of life | About the same quality of life |
| 10793421202 | Severe | Improvement of quality of life | Improvement of quality of life |
| 10788699953 | Severe | Improvement of quality of life | Improvement of quality of life |
| 10788193676 | Severe | Improvement of quality of life | Improvement of quality of life |
| 10776831268 | Severe | Improvement of quality of life | Improvement of quality of life |
| 10776563927 | Severe | Decrease in quality of life | Decrease in quality of life |
| 10773714755 | Severe | About the same quality of life | About the same quality of life |
| 10772498533 | Severe | About the same quality of life | About the same quality of life |
| 10772442051 | Severe | Improvement of quality of life | About the same quality of life |
| 10772343271 | Severe | About the same quality of life | About the same quality of life |
| 10772305396 | Severe | Improvement of quality of life | Improvement of quality of life |
| 10772265471 | Severe | Improvement of quality of life | Improvement of quality of life |
| 10771899854 | Severe | About the same quality of life | About the same quality of life |
| 10771895798 | Severe | Improvement of quality of life | Improvement of quality of life |

Table 14 below provides the survey results of the effects of the HOPE-1 and HOPE-2 tinctures on the indicated symptoms for respondents with an autism diagnosis. Further, HOPE-1 and HOPE-2 compositions will be tested and compared to other cannabinoid/terpene formulations for their relative effect on the autism symptoms described in Table 14. Such comparisons are expected to show superior results after treatment with either HOPE-1 or HOPE-2 compared to other formulations.

TABLE 14

HOPE-1 and HOPE-2 Effects in Autistic Survey Respondents

| Symptom | Score | HOPE-1 (n = 6) | HOPE-2 (n = 24) | Both (n = 10) |
|---|---|---|---|---|
| Aggression | Improved | 3/6 (50%) | 11/21 (52.3%) | 6/9 (66.7%) |
| | No change | 2/6 (33%) | 5/21 (23.8%) | 2/9 (22.2%) |
| | Worsened | 1/6 (16.7%) | 5/21 (23.8%) | 1/9 (11.1%) |
| Irritability | Improved | 3/6 (50%) | 13/23 (56.5%) | 9/9 (100%) |
| | No change | 1/6 (16.7%) | 5/23 (21.7%) | 0/9 (0%) |
| | Worsened | 2/6 (33%) | 5/23 (21.7%) | 0/9 (0%) |
| Meltdowns | Improved | 3/6 (50%) | 13/20 (65%) | 7/10 (70%) |
| | No change | 2/6 (33%) | 4/20 (20%) | 3/10 (30%) |
| | Worsened | 1/6 (16.7%) | 3/20 (15%) | 0/10 (0%) |
| Anxiety | Improved | 2/4 (50%) | 6/21 (28.6%) | 7/9 (77.8%) |
| | No change | 1/4 (25%) | 11/21 (52.3%) | 2/9 (22.2%) |
| | Worsened | 1/4 (25%) | 4/21 (19%) | 0/9 (0%) |
| Obsessive Compulsiveness | Improved | 0/4 (0%) | 2/20 (10%) | 6/10 (60%) |
| | No change | 4/4 (100%) | 12/20 (60%) | 4/10 (40%) |
| | Worsened | 0/4 (0%) | 6/20 (30%) | 0/10 (0%) |
| Focus | Improved | 1/5 (20%) | 4/18 (22.2%) | 7/10 (70%) |
| | No change | 4/5 (80%) | 10/18 (55.5%) | 2/10 (20%) |
| | Worsened | 0/5 (0%) | 4/18 (22.2%) | 1/10 (10%) |
| Seizures | Improved | 0/1 (0%) | 0/6 (0%) | 1/4 (25%) |
| | No change | 1/1 (100%) | 5/6 (83.3%) | 3/4 (75%) |
| | Worsened | 0/1 (0%) | 1/6 (16.7%) | 0/4 (0%) |
| Communication | Improved | 0/6 (0%) | 9/21 (42.9%) | 8/10 (80%) |
| | No change | 6/6 (100%) | 11/21 (52.3%) | 2/10 (20%) |
| | Worsened | 0/6 (0%) | 1/21 (4.8%) | 0/10 (0%) |

TABLE 14-continued

HOPE-1 and HOPE-2 Effects in Autistic Survey Respondents

| Symptom | Score | HOPE-1 (n = 6) | HOPE-2 (n = 24) | Both (n = 10) |
|---|---|---|---|---|
| GI Issues | Improved | 1/4 (25%) | 4/16 (25%) | 2/8 (25%) |
| | No change | 2/4 (50%) | 10/16 (62.5%) | 6/8 (75%) |
| | Worsened | 1/4 (25%) | 2/16 (12.5) | 0/8 (0%) |
| Insomnia | Improved | 0/5 (0%) | 5/16 (31.2%) | 3/8 (37.5%) |
| | No change | 3/5 (60%) | 4/16 (25%) | 4/8 (50%) |
| | Worsened | 2/5 (40%) | 7/16 (43.8%) | 1/8 (12.5%) |
| Self-Stimulatory Behavior | Improved | 0/2 (0%) | 6/20 (30%) | 4/9 (44.4%) |
| | No change | 1/2 (50%) | 8/20 (40%) | 3/9 (33.3%) |
| | Worsened | 1/2 (50%) | 6/20 (30%) | 2/9 (22.2%) |
| Hyperactivity | Improved | 1/4 (25%) | 5/18 (27.8%) | 5/9 (55.6%) |
| | No change | 2/4 (50%) | 7/18 (38.9%) | 2/9 (22.2%) |
| | Worsened | 1/4 (25%) | 6/18 (33.3%) | 2/9 (22.2%) |
| Pain | Improved | 0/1 (0%) | 0/7 (0%) | 2/4 (50%) |
| | No change | 1/1 (100%) | 6/7 (85.7%) | 2/4 (50%) |
| | Worsened | 0/1 (0%) | 1/7 (14.3%) | 0/4 (0%) |
| Appetite | Improved | 0/3 (0%) | 3/17 (17.6%) | 3/8 (37.5%) |
| | No change | 2/3 (66%) | 11/17 (64.7%) | 4/8 (50%) |
| | Worsened | 1/3 (33%) | 3/17 (17.6%) | 1/8 (12.5%) |
| Rage | Improved | 1/2 (50%) | 7/16 (43.8%) | 5/8 (62.5%) |
| | No change | 0/2 (50%) | 7/16 (43.8%) | 3/8 (37.5%) |
| | Worsened | 1/2 (50%) | 2/16 (12.5%) | 0/8 (0%) |
| Agitation | Improved | 2/3 (66%) | 9/22 (40.9%) | 7/9 (77.8%) |
| | No change | 0/3 (0%) | 8/22 (36.4%) | 1/9 (11.1%) |
| | Worsened | 1/3 (33%) | 5/22 (22.7%) | 1/9 (11.1%) |
| Self-Injurious Behaviors | Improved | 2/3 (66%) | 9/15 (60%) | 5/7 (71.4%) |
| | No change | 0/3 (0%) | 3/15 (20%) | 2/7 (28.5%) |
| | Worsened | 1/3 (33%) | 3/15 (20%) | 0/7 (0%) |

Overall, this survey adds to real life empirical experience data that cannabinoid-based formulations are well tolerated for the relief of symptoms associated with autism spectrum disorders. This survey appears to be the first report for a specific formulation of cannabinoid-based product or products associated with autism spectrum disorders. Several other available reports are based on anecdotal use of many different *Cannabis* products (CBD only or CBD rich) for the relief of symptoms associated with ASD.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world.

The invention claimed is:

1. A method of reducing agitation in a patient with autism spectrum disorder (ASD), said method comprising administering a pharmaceutical composition to the patient, wherein the pharmaceutical composition comprises:
   (a) a Cannabinoid Profile comprising Tetrahydrocannabinol (THC) and Cannabidiol (CBD) at a THC: CBD ratio of 1:1 by weight; and
   (b) a Terpene Profile comprising a-Pinene, Valencene, and Eucalyptol.

2. The method of claim 1, wherein the Terpene Profile comprises 25%-35% α-Pinene by weight, 25%-35% Valencene by weight, and 30%-40% Eucalyptol by weight, wherein the total of % α-Pinene+ % Valencene+ % Eucalyptol=100%.

3. The method of claim 1, wherein the pharmaceutical composition comprises about 31% α-Pinene by weight, about 31% Valencene by weight, and about 37.5% Eucalyptol by weight.

4. The method of claim 1, wherein the ratio of the Cannabinoid Profile to Terpene Profile is between 10:1 and 5:1 by weight.

5. The method of claim 1, wherein the pharmaceutical composition is peppermint flavored.

6. The method of claim 1, wherein the pharmaceutical composition is vanilla flavored.

7. The method of claim 1, wherein the pharmaceutical composition is lemon flavored.

8. The method of claim 1, wherein the pharmaceutical composition is orange flavored.

9. The method of claim 1, wherein the pharmaceutical composition is ginger flavored.

10. The method of claim 1, wherein the pharmaceutical composition is passionfruit flavored.

11. The method of claim 1, wherein the pharmaceutical composition further comprises olive oil.

12. The method of claim 1, wherein the pharmaceutical composition is formulated for oral administration.

13. The method of claim 1, wherein the pharmaceutical composition is formulated as a liquid dose.

14. The method of claim 13, wherein the liquid dose is about 2.5 mL.

15. The method of claim 13, wherein the liquid dose is about 5 mL.

16. The method of claim 1, wherein the total amount of CBD and THC in the pharmaceutical composition is 300 mg.

17. The method of claim 1, wherein the pharmaceutical composition comprises from 125 mg to 175 mg of CBD.

18. The method of claim 1, wherein the pharmaceutical composition comprises from 125 mg to 175 mg of THC.

19. The method of claim 1, wherein the pharmaceutical composition comprises about 5 mg/mL THC, about 5 mg/mL CBD, about 0.43 mg/mL a-pinene, about 0.43 mg/mL valencene, and about 0.5 mg/mL eucalyptol.

* * * * *